US009605059B2

(12) United States Patent
Nitsch et al.

(10) Patent No.: US 9,605,059 B2
(45) Date of Patent: Mar. 28, 2017

(54) HUMAN ANTI-TAU ANTIBODIES

(71) Applicants: Biogen International Neuroscience GmbH, Zug (CH); University of Zürich, Zürich (CH)

(72) Inventors: Roger Nitsch, Zumikon (CH); Feng Chen, Zurich (CH); Jan Grimm, Duebendorf (CH); Jean-Luc Baeriswyl, Zurich (CH); Christoph Hock, Erlenbach (CH)

(73) Assignees: Biogen International Neuroscience GmbH, Zug (CH); University of Zürich, Zürich (CH)

( * ) Notice: Subject to any disclaimer, the term of this patent is extended or adjusted under 35 U.S.C. 154(b) by 0 days.

(21) Appl. No.: 14/532,531

(22) Filed: Nov. 4, 2014

(65) Prior Publication Data

US 2015/0252102 A1 Sep. 10, 2015

Related U.S. Application Data

(62) Division of application No. 13/271,118, filed on Oct. 11, 2011, now Pat. No. 8,940,272.

(60) Provisional application No. 61/391,751, filed on Oct. 11, 2010.

(30) Foreign Application Priority Data

Oct. 11, 2010 (EP) .................................... 10013494

(51) Int. Cl.
| | |
|---|---|
| *C07K 14/47* | (2006.01) |
| *C07K 16/18* | (2006.01) |
| *G01N 33/68* | (2006.01) |
| *A61K 39/395* | (2006.01) |
| *A61K 39/00* | (2006.01) |

(52) U.S. Cl.
CPC .......... *C07K 16/18* (2013.01); *A61K 39/3955* (2013.01); *C07K 14/47* (2013.01); *C07K 14/4711* (2013.01); *G01N 33/6896* (2013.01); *A61K 2039/505* (2013.01); *C07K 2317/10* (2013.01); *C07K 2317/21* (2013.01); *C07K 2317/24* (2013.01); *C07K 2317/34* (2013.01); *C07K 2317/41* (2013.01); *C07K 2317/52* (2013.01); *C07K 2317/56* (2013.01); *C07K 2317/565* (2013.01); *C07K 2317/90* (2013.01); *C07K 2317/92* (2013.01); *G01N 2333/47* (2013.01); *G01N 2800/56* (2013.01)

(58) Field of Classification Search
CPC  C07K 16/18; C07K 2317/24; C07K 14/4711; C07K 2317/34; C07K 2317/565; C07K 2317/76; C07K 2317/55; C07K 2317/56; C07K 2317/567; C07K 2317/54; C07K 14/47; C07K 16/461; C07K 2317/622; A61K 2039/505; A61K 39/0005; A61K 2039/507; A61K 47/48561; A61K 47/48538; A61K 49/16; G01N 33/6896; G01N 2333/4709; G01N 2800/2814; G01N 2800/2821; Y10S 424/80; C07H 21/04; C12Y 207/11026; G06F 19/22; Y10T 436/143333

See application file for complete search history.

(56) References Cited

U.S. PATENT DOCUMENTS

| | | | |
|---|---|---|---|
| 7,442,516 B2 | 10/2008 | Ohno et al. | |
| 8,940,272 B2 | 1/2015 | Nitsch et al. | |
| 2004/0110938 A1 | 6/2004 | Parekh et al. | |
| 2006/0122122 A1 | 6/2006 | Kobayashi et al. | |
| 2008/0050383 A1 | 2/2008 | Sigurdsson et al. | |
| 2010/0316564 A1* | 12/2010 | Sigurdsson ........ | A61K 39/0005 424/1.49 |
| 2012/0087861 A1 | 4/2012 | Nitsch et al. | |
| 2012/0323214 A1 | 12/2012 | Shantha | |
| 2013/0295021 A1 | 11/2013 | Nitsch et al. | |
| 2015/0344553 A1 | 12/2015 | Weinreb et al. | |

FOREIGN PATENT DOCUMENTS

| | | |
|---|---|---|
| WO | WO 93/08302 A1 | 4/1993 |
| WO | WO 94/13795 A1 | 6/1994 |
| WO | WO 95/17429 A1 | 6/1995 |
| WO | WO 96/04309 A1 | 2/1996 |
| WO | WO 98/22120 A1 | 5/1998 |
| WO | WO 02/062851 A1 | 8/2002 |
| WO | WO 03/014960 A2 | 2/2003 |
| WO | WO 03/017918 A2 | 3/2003 |
| WO | WO 2004/016655 A1 | 2/2004 |
| WO | WO 2005/080986 A1 | 9/2005 |

(Continued)

OTHER PUBLICATIONS

Abou-Doniaa et al. "Autoantibodies against cytoskeletal neuronal proteins in sera of arsenic-exposed subjects correlate with neurological symptoms," Toxicological & Environmental Chemistry 95(5):823-836, Jun. 18, 2013, Abstract only, 3 pages.

(Continued)

*Primary Examiner* — Gregory S Emch
(74) *Attorney, Agent, or Firm* — Fish & Richardson P.C.

(57) ABSTRACT

Provided are novel human tau-specific antibodies as well as fragments, derivatives and variants thereof as well as methods related thereto. Assays, kits, and solid supports related to antibodies specific for tau are also disclosed. The antibody, immunoglobulin chain(s), as well as binding fragments, derivatives and variants thereof can be used in pharmaceutical and diagnostic compositions for tau targeted immunotherapy and diagnosis, respectively.

70 Claims, 18 Drawing Sheets

(56) References Cited

FOREIGN PATENT DOCUMENTS

| | | |
|---|---|---|
| WO | WO 2006/122122 | 6/2006 |
| WO | WO 2007/068105 A1 | 6/2007 |
| WO | WO 2008/081008 A1 | 7/2008 |
| WO | WO 2010/142423 | 12/2010 |
| WO | WO 2010/144711 A2 | 12/2010 |
| WO | WO 2011/053565 | 5/2011 |
| WO | WO 2012/045882 | 4/2012 |
| WO | WO 2012/049570 | 4/2012 |
| WO | WO 2012/106363 | 8/2012 |
| WO | WO 2012/149365 | 11/2012 |

OTHER PUBLICATIONS

Boutajangout et at., "Passive immunization targeting pathological phospo-tau protein in a mouse model reduces functional decline and clears tau aggregates from the brain," Journal of Neurochemistry, 118(4): 658-667 (2011), 16 pages.

International Preliminary Report on Patentability in International Application No. PCT/US2013/076952, dated Jun. 23, 2015, 13 pages.

International Search Report and Written Opinion in International Application No. PCT/US2013/076952, dated Sep. 7, 2014, 22 pages.

Aluise, C.D., et al, "Peptides and Proteins in Plasma and Cerebrospinal Fluid as f Biomarkers for the Prediction, Diagnosis, and Monitoring of Therapeutic Efficacy of Alzheimer's Disease," *Biochim Biophys Acta.* 1782(10):549-558, Elsevier Pub. Co., Netherlands (2008).

Asuni, A.A., et al., "Immunotherapy Targeting Pathological Tau Conformers in a Tangle Mouse Model Reduces Brain Pathology with Associated Functional Improvements," *The Journal of Neuroscience* 27(34):9115-9129, Society for Neuroscience, United States (2007).

Augustinack et al., "Specific tau phosphoiylation sites correlate with severity of neuronal cytopathology in Alzheimer's disease," *Acta Neuropathol* 103:26-35, Springer-Verlag, Germany (2002), published online Oct. 26, 2001.

Boche, D., et al., "Reduction of aggregated Tau in neuronal processes but not in the cell bodies after Aβ42 immunisation in Alzheimer's disease," *Acta Neuropathol* 120:13-20, Springer-Verlag, Germany (2010).

Boimel, M., et al., "Efficacy and safety of immunization with phosphorylated tau against neurofibrillary tangles in mice," *Exp. Neurol.* 224:472-485, Elsevier Inc., United States (2010).

Cairns, N.J., et al., "TDP-43 in Familial and Sporadic Frontotemporal Lobar Degeneration with Ubiquitin Inclusions," *The American Journal of Pathology* 171(1):227-240, American Society for Investigative Pathology, United States (2007).

Fisher, N., and Leger, O., "Bispecific Antibodies: Moldcules That Enable Novel Therapeutic Strategies," *Pathobiology* 74:3-14, S. Karger AG, Switzerland (2007).

Frost, B., et al., "Propagation of Tau Misfolding from the Outside to the Inside of a Cell," *The Journal of Biological Chemistry* 284(19): 12845-12852, The American Society for Biochemistry and Molecular Biology, Inc., United States (2009).

Gallyas, F., "A Principle for Silver Staining of Tissue Elements by Physical Development," *Acta Morphologica Acad. Sci. Hung.* 19(1):57-71, Akademiai Kiado, Hungary (1971).

Gallyas, F., "Silver Staining of Alzheimer's Neurofibrillary Changes by Means of Physical Development," *Acta Morphologica Acad. Sci. Hung.* 19(1):1-8, Akademiai Kiado, Hungary (1971).

Gendron, T.F., and Petrucelli, L., "The role of tau in neurodegeneration," *Molecular Neurodegeneration* 4(13):19 pages, BioMed Central Ltd., England (2009).

Goedert, M, and Jakes, R., "Expression of separate isoforms of human tau protein: correlation with the tau pattern in brain and effects on tubulin polymerization," *The EMBO Journal* 9(15):4225-4230, Oxford University Press, England (1990).

Goedert, M., et al., "Cloning and sequencing of the cDNA encoding a core protein of the paired helical filament of Alzheimer disease: Identification as the microtubule-associated protein tau," *Proc. Natl. Acad. Sci. USA* 55:4051-4055, National Academy of Sciences, United States (1988).

Goedert, M., et al., "Cloning and sequencing of the cDNA encoding an isoform of microtubule-associated protein tau containing four tandem repeats: differential expression of tau protein mRNAs in human brain," *The EMBO Journal* 8(2):393-399, IRL Press, England (1989).

Goedert, M., et al., "Tau Proteins of Alzheimer Paired Helical Filaments: Abnormal Phosphorylation of All Six Brain isoforms," *Neuron* 8:159-168, Cell Press, United States (1992).

Gotz, J., "Tau and transgenic animal models," *Brain Research Reviews* 35:266-286, Elsevier Science B.V., Netherlands (2001).

Gotz, J., et al., "Formation of Neurofibrillary Tangles in P301L Tau Transgen ic Mice Induced by Aβ42 Fibrils," *Science* 293:1491-1495, American Association for the Advancement of Science, United States (2001).

Gotz, J., et al, "Tau Filament Formation in Transgenic Mice Expressing P301L Tau," *The Journal of Biological Chemistry* 276(1):529-534, The American Society for Biochemistry and Molecular Biology, Inc., United States (2001).

Hoffmann, R., et al., "Unique Alzheimer's Disease Paired Helical Filament Specific Epitopes Involve Double Phosphorylation at Specific Sites." *Biochemistry* 36:8114-8124, American Chemical Society, United States (1997).

Holmes, C., et al., "Long-term effects of $A\beta_{42}$ immunisation in Alzheimer's disease: follow-up of a randomised, placebo-controlled phase I trial," *Lancet* 372:216-223, Elsevier Ltd., England (2008).

Khlistunova, I., et al., "Inducible Expression of Tau Repeat Domain in Cell Models of Tauopathy: Aggregation is Toxic to Cells But Can be Reversed by Inhibitor Drugs," *The Journal of Biological Chemistry* 281 (2):1205-1214, The American Society for Biochemistry and Molecular Biology. Inc., United States (2006).

Lee, V.M-Y., et al., "Neurodegenerative Tauopathies," *Annu. Rev. Neurosci.* 24:1121-1159, Annual Reviews, United States (2001).

Miller, T.W., and Messer, A., "Intrabody Applications in Neurological Disorders: Progress and Future Prospects," *Molecular Therapy* 12(3):394-401, The American Society of Gene Therapy, United States (2005).

Van de Nes, J.A.P., et al., "β-Protein/A4 deposits are not associated with hyperphosphorylated tau in somatostatin neurons in the hypothalamus of Alzheimer's disease patients," *Acta Neuropathol* 111:126-138, Springer-Verlag, Germany (2006).

Pennanen, L., et al., "Accelerated Extinction of conditioned taste aversion in P301L tau transgenic mice," *Neurobiology Disease* 15:500-509, Elsevier Inc., United States (2004).

Pennanen, L., et al., "Impaired spatial reference memory and increased exploratory behavior in P301L tau transgenic mice," *Genes, Brain and Behavior* 5:369-379, Blackwell Munksgaard, England (2005).

Robert, R., et al., "Engineered antibody intervention strategies for Alzheimer's disease and related dementias by targeting amyloid and toxic oligomers," *Protein Engineering, Design & Selection* 22(3): 199-208, Oxford University Press, England (2008).

Rosenmann, H., et al., "Taupathy-like Abnormalities and Neurologic Deficits in Mice Immunized With Neuronal Tau Protein," *Arch Neurol.* 63:1459-1467, American Medical Association, United States (2006).

Sergeant, N., et al., "Tau protein as a differential biomarker of tauopathies," *Biochimica et Biophysica Acta* 1739:179-197, Elsevier B.V., England (2004).

Sigurdsson, E.M., "Immunotherapy Targeting Pathological Tau Protein in Alzheimer's Disease and Related Taupathies," *J Alzheimers Dis.* 15(2): 157-168, IOS Press, Netherlands (2008).

Talan, J., "Advances Reported in Targeting Tau Pathology in Alzheimer Disease," *Neurology Today* 10(16):17-19, American Academy ofNeurology, United States (2010).

Zheng, G-Q., etal., "Tau as a Potential Novel Therapeutic Target in Ischemic Stroke," *Journal Cellular Biochemistry* 109:26-29, Wiley-Liss, Inc., United States (2010), published online Nov. 13, 2009.

(56) References Cited

OTHER PUBLICATIONS

European Search Report for EP Application No. 10013494.9, European Patent Office, Netherlands, mailed on Mar. 28, 2011.
International Search Report and Written Opinion for International Application No. PCT/IB2011/002786, European Patent Office, Netherlands, mailed on Mar. 7, 2012.
"Four New Research Studies Describe Experimental Imunotherapies for for Alzheimer's," p. 2, section "Tau Antibodies Reduce Brain Tangles in Alzheimer-Model Mice," Alzheimer's Association International Conference on Alzheimer's Disease, accessed at http://www.alz.org/icad/2010_release_four_071310_1230pm.asp, accessed on Feb. 28, 2011.
Chen "Enhancement and destruction of antibody function by somatic mutation: Unequal occurrence is controlled by V gene combinatorial associations," EMBO 14(12):2784-2794 (1995).
Colombian Office Action in International Application No. 15-168.271, dated Oct. 14, 2016, 29 pages.
European Examination Report in International Application No. 13818637.4, dated Oct. 10, 2016, 15 pages.
Goedert et al., "Epitope mapping of monoclonal antibodies to the paired helical filaments of Alzheimer's disease: identification of phosphorylation sites in tau protein," Biochemical Journal, 301(3):871-877 (Aug. 1994).
Karu et al., "Recombinant Antibody Technology," ILAR Journal, 37(3):132-41 (Jan. 1995).
Kussie, "A single engineered amino acid substitution changes antibody fine specificity," J Immunol., 152(1):146-52 (1994).
Otvos et al., "Monoclonal Antibody PHF4 Recognizes Tau Protein Phosphorylated at Serine Residues 396 and 404," Journal of Neuroscience Research, 39:669-673 (Jan. 1994).
Hagemeyer et al., "Single-chain antibodies as new antithrombic drugs," Seminar Thromb Hemo. 33(2):185-195 (2007).
Mapiedi et al., "Single-chain antibody fragments: purification methodologies," Process Biochem. 48:1241-1251 (2013).

* cited by examiner

A NI-105.4E4-VH (variable heavy chain sequence VH; SEQ ID NO: 9)
```
FR1-----------------------------CDR1-FR2-----------CDR2---------
EVQLVESGGGLVQPGGSLKLSCAASGFNFNISAIHWVRQASGKGLEWVGRIRSKSHNYATLY ------FR3-------------------------------CDR3------FR4---------
AASLKGRFTLSRDDSRNTAYLQMSSLQTEDMAVYYCTVLSANYDTFDYWGQGTLVTVSS
```

NI-105.4E4-VL (variable light chain sequence VL; SEQ ID NO: 11)
```
FR1-------------------CDR1-------FR2------------CDR2---FR3----
SYELTQPPSVSVSPGQTARISCFGDTLPKQYTYWYQQKPGQAPVLVIYKDTERPSGIPERFS
LPV
-------------------------CDR3------FR4-------
GSSSGTTVTLTISGVQAEDEADYYCLSADNSATWVFGGGTKVTVL
```

B NI-105.24B2-VH (variable heavy chain sequence VH; SEQ ID NO: 13)
```
FR1----------------------------CDR1-FR2-----------CDR2---------
QVQLVQSGAEVKKPGASVKVSCKASGYTFVNYIIHWVRQAPGQGLEWMGIINPNGGNTSYAE
E
----FR3-------------------------CDR3--FR4--------
KFQARVTLTSDTSTSTVYMDLSSLTSEDTAVYYCAVLSPSNPWGQGTTVTVSS
```

NI-105.24B2-VL (variable light chain sequence VL; SEQ ID NO: 15)
```
FR1---------------------CDR1---------FR2---------------CDR2---FR3----
SYELTQPPSVSVSPGQTAGITCSGDALPKQFVYWYQKKPGQAPVLLIYKDTERPSRIPERFS
   V
---------------------------CDR3-------FR4-------
GSTSGTTVALTINGVQAEDEADYYCQSADRSGALWVFGGGTKLTVL
```

C NI-105.4A3-VH (variable heavy chain sequence VH; SEQ ID NO: 17)
```
FR1-----------------------------CDR1-FR2-----------CDR2---------
QVQLVESGGGAVQPGGSLRLSCAASGFTFSDYAMHWVRQAPGKGLQWVAVISYEGTYKYYAD
E     T
----FR3---------------------------CDR3-------------FR4------
SVKGRFTISRDNSKNTLNLQMSSLRVEDTAVYFCVKARAFASGQRSTSTVPDYWGQGTLVTV
SS
```

NI-105.4A3-VL (variable light chain sequence VL; SEQ ID NO: 19)
```
FR1------------------CDR1-------FR2-------------CDR2---FR3----
SYELTQPPSVSVSPGQTARITCSGDALPKKYAYWYQQKSGQAPVLVIYEDNKRPSGIPERFS ---------------------------CDR3-------FR4-------
GSSSGTVATLTISGAQVDDEADYYCYSTDISGDLRVFGGGTKLTVL
```

FIG. 1

Alanine mutagenesis table 4E4 epitope ${}_{335}$GQVEVK SEKLDFKDR${}_{349}$

| | | | | | | | | | | | | | | | | |
|---|---|---|---|---|---|---|---|---|---|---|---|---|---|---|---|---|
| 35 | G | Q | V | E | V | K | S | E | K | L | D | F | K | D | R | SEQ ID NO: 43 |
| 36 | A | Q | V | E | V | K | S | E | K | L | D | F | K | D | R | SEQ ID NO: 44 |
| 37 | G | A | V | E | V | K | S | E | K | L | D | F | K | D | R | SEQ ID NO: 45 |
| 38 | G | Q | A | E | V | K | S | E | K | L | D | F | K | D | R | SEQ ID NO: 46 |
| 39 | G | Q | V | A | V | K | S | E | K | L | D | F | K | D | R | SEQ ID NO: 47 |
| 40 | G | Q | V | E | A | K | S | E | K | L | D | F | K | D | R | SEQ ID NO: 48 |
| 41 | G | Q | V | E | V | A | S | E | K | L | D | F | K | D | R | SEQ ID NO: 49 |
| 42 | G | Q | V | E | V | K | A | E | K | L | D | F | K | D | R | SEQ ID NO: 50 |
| 43 | G | Q | V | E | V | K | S | A | K | L | D | F | K | D | R | SEQ ID NO: 51 |
| 44 | G | Q | V | E | V | K | S | E | A | L | D | F | K | D | R | SEQ ID NO: 52 |
| 45 | G | Q | V | E | V | K | S | E | K | A | D | F | K | D | R | SEQ ID NO: 53 |
| 46 | G | Q | V | E | V | K | S | E | K | L | A | F | K | D | R | SEQ ID NO: 54 |
| 47 | G | Q | V | E | V | K | S | E | K | L | D | A | K | D | R | SEQ ID NO: 55 |
| 48 | G | Q | V | E | V | K | S | E | K | L | D | F | A | D | R | SEQ ID NO: 56 |
| 49 | G | Q | V | E | V | K | S | E | K | L | D | F | K | A | R | SEQ ID NO: 57 |
| 50 | G | Q | V | E | V | K | S | E | K | L | D | F | K | D | A | SEQ ID NO: 58 |

FIG. 4E
Alanine mutagenesis table 4E4 epitope
383 KAKTDHGA EIVYKSP 397

| | | | | | | | | | | | | | | | | |
|---|---|---|---|---|---|---|---|---|---|---|---|---|---|---|---|---|
| 51 | K | A | K | T | D | H | G | A | E | I | V | Y | K | S | P | SEQ ID NO: 59 |
| 52 | A | A | K | T | D | H | G | A | E | I | V | Y | K | S | P | SEQ ID NO: 60 |
| 53 | K | G | K | T | D | H | G | A | E | I | V | Y | K | S | P | SEQ ID NO: 61 |
| 54 | K | P | K | T | D | H | G | A | E | I | V | Y | K | S | P | SEQ ID NO: 62 |
| 55 | K | A | A | T | D | H | G | A | E | I | V | Y | K | S | P | SEQ ID NO: 63 |
| 56 | K | A | K | A | D | H | G | A | E | I | V | Y | K | S | P | SEQ ID NO: 64 |
| 57 | K | A | K | T | A | H | G | A | E | I | V | Y | K | S | P | SEQ ID NO: 65 |
| 58 | K | A | K | T | D | A | G | A | E | I | V | Y | K | S | P | SEQ ID NO: 66 |
| 59 | K | A | K | T | D | H | A | A | E | I | V | Y | K | S | P | SEQ ID NO: 67 |
| 60 | K | A | K | T | D | H | G | G | E | I | V | Y | K | S | P | SEQ ID NO: 68 |
| 61 | K | A | K | T | D | H | G | P | E | I | V | Y | K | S | P | SEQ ID NO: 69 |
| 62 | K | A | K | T | D | H | G | A | A | I | V | Y | K | S | P | SEQ ID NO: 70 |
| 63 | K | A | K | T | D | H | G | A | E | A | V | Y | K | S | P | SEQ ID NO: 71 |
| 64 | K | A | K | T | D | H | G | A | E | I | A | Y | K | S | P | SEQ ID NO: 72 |
| 65 | K | A | K | T | D | H | G | A | E | I | V | A | K | S | P | SEQ ID NO: 73 |
| 66 | K | A | K | T | D | H | G | A | E | I | V | Y | A | S | P | SEQ ID NO: 74 |
| 67 | K | A | K | T | D | H | G | A | E | I | V | Y | K | A | P | SEQ ID NO: 75 |
| 68 | K | A | K | T | D | H | G | A | E | I | V | Y | K | S | A | SEQ ID NO: 76 |

A
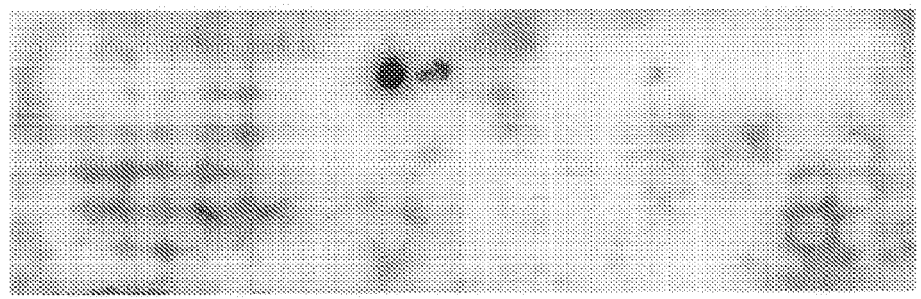

B
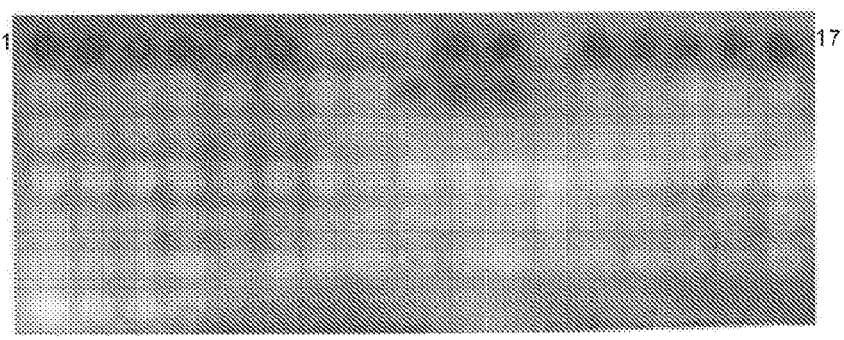

C
Alanine Mutagenesis Table

| | | | | | | | | | | | | | | | |
|---|---|---|---|---|---|---|---|---|---|---|---|---|---|---|---|
| 1 | Q | E | G | D | T | D | A | G | L | K | E | S | P | L | Q | SEE ID NO: 42 |
| 2 | A | E | G | D | T | D | A | G | L | K | E | S | P | L | Q | SEE ID NO: 77 |
| 3 | Q | A | G | D | T | D | A | G | L | K | E | S | P | L | Q | SEE ID NO: 78 |
| 4 | Q | E | A | D | T | D | A | G | L | K | E | S | P | L | Q | SEE ID NO: 79 |
| 5 | Q | E | G | A | T | D | A | G | L | K | E | S | P | L | Q | SEE ID NO: 80 |
| 6 | Q | E | G | D | A | D | A | G | L | K | E | S | P | L | Q | SEE ID NO: 81 |
| 7 | Q | E | G | D | T | A | A | G | L | K | E | S | P | L | Q | SEE ID NO: 82 |
| 8 | Q | E | G | D | T | D | G | G | L | K | E | S | P | L | Q | SEE ID NO: 83 |
| 9 | Q | E | G | D | T | D | P | G | L | K | E | S | P | L | Q | SEE ID NO: 84 |
| 10 | Q | E | G | D | T | D | A | A | L | K | E | S | P | L | Q | SEE ID NO: 85 |
| 11 | Q | E | G | D | T | D | A | G | A | K | E | S | P | L | Q | SEE ID NO: 86 |
| 12 | Q | E | G | D | T | D | A | G | L | A | E | S | P | L | Q | SEE ID NO: 87 |
| 13 | Q | E | G | D | T | D | A | G | L | K | A | S | P | L | Q | SEE ID NO: 88 |
| 14 | Q | E | G | D | T | D | A | G | L | K | E | A | P | L | Q | SEE ID NO: 89 |
| 15 | Q | E | G | D | T | D | A | G | L | K | E | S | A | L | Q | SEE ID NO: 90 |
| 16 | Q | E | G | D | T | D | A | G | L | K | E | S | P | A | Q | SEE ID NO: 91 |
| 17 | Q | E | G | D | T | D | A | G | L | K | E | S | P | L | A | SEE ID NO: 92 |

FIG. 14

SEQUENCE LISTING

```
<160> NUMBER OF SEQ ID NOS: 93

<210> SEQ ID NO 1
<211> LENGTH: 352
<212> TYPE: PRT
<213> ORGANISM: Homo sapiens
<220> FEATURE:
<221> NAME/KEY: PEPTIDE
<222> LOCATION: (1)..(352)
<223> OTHER INFORMATION: Isoform Fetal-Tau
<300> PUBLICATION INFORMATION:
<301> AUTHORS: Goedert M., Wischik C., Crowther R., Walker J., Klug A.
<302> TITLE: Cloning and sequencing of the cDNA encoding a core protein
       of the paired helical filament of Alzheimer disease:
       identification as the microtubule-associated protein tau.
<303> JOURNAL: Proc. Natl. Acad. Sci. U.S.A.
<304> VOLUME: 85
<306> PAGES: 4051-4055
<307> DATE: 1988-06-01
<300> PUBLICATION INFORMATION:
<308> DATABASE ACCESSION NUMBER: P10636-2
<309> DATABASE ENTRY DATE: 2010-10-05
<313> RELEVANT RESIDUES IN SEQ ID NO: (1)..(352)

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
```

```
                  20                  25                  30

Gln Asp Gln Glu Gly Asp Thr Asp Ala Gly Leu Lys Ala Glu Glu Ala
                     35                  40                  45

Gly Ile Gly Asp Thr Pro Ser Leu Glu Asp Glu Ala Ala Gly His Val
                     50                  55                  60

Thr Gln Ala Arg Met Val Ser Lys Ser Lys Asp Gly Thr Gly Ser Asp
         65                  70                  75                  80

Asp Lys Lys Ala Lys Gly Ala Asp Gly Lys Thr Lys Ile Ala Thr Pro
                         85                  90                  95

Arg Gly Ala Ala Pro Pro Gly Gln Lys Gly Gln Ala Asn Ala Thr Arg
                    100                 105                 110

Ile Pro Ala Lys Thr Pro Pro Ala Pro Lys Thr Pro Pro Ser Ser Gly
                    115                 120                 125

Glu Pro Pro Lys Ser Gly Asp Arg Ser Gly Tyr Ser Ser Pro Gly Ser
                    130                 135                 140

Pro Gly Thr Pro Gly Ser Arg Ser Arg Thr Pro Ser Leu Pro Thr Pro
        145                 150                 155                 160

Pro Thr Arg Glu Pro Lys Lys Val Ala Val Val Arg Thr Pro Pro Lys
                        165                 170                 175

Ser Pro Ser Ser Ala Lys Ser Arg Leu Gln Thr Ala Pro Val Pro Met
                    180                 185                 190

Pro Asp Leu Lys Asn Val Lys Ser Lys Ile Gly Ser Thr Glu Asn Leu
                    195                 200                 205

Lys His Gln Pro Gly Gly Gly Lys Val Gln Ile Val Tyr Lys Pro Val
                210                 215                 220

Asp Leu Ser Lys Val Thr Ser Lys Cys Gly Ser Leu Gly Asn Ile His
        225                 230                 235                 240

His Lys Pro Gly Gly Gly Gln Val Glu Val Lys Ser Glu Lys Leu Asp
                        245                 250                 255

Phe Lys Asp Arg Val Gln Ser Lys Ile Gly Ser Leu Asp Asn Ile Thr
                    260                 265                 270

His Val Pro Gly Gly Gly Asn Lys Lys Ile Glu Thr His Lys Leu Thr
                    275                 280                 285

Phe Arg Glu Asn Ala Lys Ala Lys Thr Asp His Gly Ala Glu Ile Val
                290                 295                 300

Tyr Lys Ser Pro Val Val Ser Gly Asp Thr Ser Pro Arg His Leu Ser
        305                 310                 315                 320

Asn Val Ser Ser Thr Gly Ser Ile Asp Met Val Asp Ser Pro Gln Leu
                        325                 330                 335

Ala Thr Leu Ala Asp Glu Val Ser Ala Ser Leu Ala Lys Gln Gly Leu
                    340                 345                 350

<210> SEQ ID NO 2
<211> LENGTH: 381
<212> TYPE: PRT
<213> ORGANISM: Homo sapiens
<220> FEATURE:
<221> NAME/KEY: PEPTIDE
<222> LOCATION: (1)..(381)
<223> OTHER INFORMATION: Isoform Tau-B
<300> PUBLICATION INFORMATION:
<301> AUTHORS: Goedert M., Spillantini M.G., Jakes R., Rutherford D.,
       Crowther R.A.
<302> TITLE: Multiple isoforms of human microtubule-associated protein
       tau: sequences and localization in neurofibrillary tangles of
       Alzheimer's disease.
<303> JOURNAL: Neuron
<304> VOLUME: 3
```

<306> PAGES: 519-526
<307> DATE: 1989-10-01
<300> PUBLICATION INFORMATION:
<308> DATABASE ACCESSION NUMBER: P10636-4
<309> DATABASE ENTRY DATE: 2010-10-05
<313> RELEVANT RESIDUES IN SEQ ID NO: (1)..(381)

<400> SEQUENCE: 2

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
```

```
              370                 375                 380

<210> SEQ ID NO 3
<211> LENGTH: 410
<212> TYPE: PRT
<213> ORGANISM: Homo sapiens
<220> FEATURE:
<221> NAME/KEY: PEPTIDE
<222> LOCATION: (1)..(410)
<223> OTHER INFORMATION: Isoform Tau-C
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-5
<309> DATABASE ENTRY DATE: 2010-10-05
<313> RELEVANT RESIDUES IN SEQ ID NO: (1)..(410)

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
        290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 4
<211> LENGTH: 383
<212> TYPE: PRT
<213> ORGANISM: Homo sapiens
<220> FEATURE:
<221> NAME/KEY: PEPTIDE
<222> LOCATION: (1)..(383)
<223> OTHER INFORMATION: Isoform Tau-D
<300> PUBLICATION INFORMATION:
<301> AUTHORS: Goedert M., Spillantini M.G., Potier M.-C., Ulrich J.,
      Crowther R.A.
<302> TITLE: Cloning and sequencing of the cDNA encoding an isoform of
      microtubule-associated protein tau containing four tandem
      repeats: differential expression of tau protein mRNAs in human
      brain.
<303> JOURNAL: EMBO J.
<304> VOLUME: 8
<306> PAGES: 393-399
<307> DATE: 1989-02-01
<300> PUBLICATION INFORMATION:
<308> DATABASE ACCESSION NUMBER: P10636-6
<309> DATABASE ENTRY DATE: 2010-10-05
<313> RELEVANT RESIDUES IN SEQ ID NO: (1)..(383)

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser

```
                    130                 135                 140
Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
            195                 200                 205

Lys His Gln Pro Gly Gly Gly Lys Val Gln Ile Ile Asn Lys Lys Leu
        210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
                260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
        370                 375                 380

<210> SEQ ID NO 5
<211> LENGTH: 412
<212> TYPE: PRT
<213> ORGANISM: Homo sapiens
<220> FEATURE:
<221> NAME/KEY: PEPTIDE
<222> LOCATION: (1)..(412)
<223> OTHER INFORMATION: Isoform Tau-E
<300> PUBLICATION INFORMATION:
<301> AUTHORS: Goedert M., Spillantini M.G., Jakes R., Rutherford D.,
      Crowther R.A.
<302> TITLE: Multiple isoforms of human microtubule-associated protein
      tau: sequences and localization in neurofibrillary tangles of
      Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-7
<309> DATABASE ENTRY DATE: 2010-10-05
<313> RELEVANT RESIDUES IN SEQ ID NO: (1)..(412)

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

Gln Asp Gln Glu Gly Asp Thr Asp Ala Gly Leu Lys Glu Ser Pro Leu
 35                  40                  45

Gln Thr Pro Thr Glu Asp Gly Ser Glu Pro Gly Ser Glu Thr Ser
 50                  55                  60

Asp Ala Lys Ser Thr Pro Thr Ala Glu Ala Glu Glu Ala Gly Ile Gly
 65                  70                  75                  80

Asp Thr Pro Ser Leu Glu Asp Glu Ala Ala Gly His Val Thr Gln Ala
                 85                  90                  95

Arg Met Val Ser Lys Ser Lys Asp Gly Thr Gly Ser Asp Asp Lys Lys
             100                 105                 110

Ala Lys Gly Ala Asp Gly Lys Thr Lys Ile Ala Thr Pro Arg Gly Ala
         115                 120                 125

Ala Pro Pro Gly Gln Lys Gly Gln Ala Asn Ala Thr Arg Ile Pro Ala
     130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 6
<211> LENGTH: 441
<212> TYPE: PRT
<213> ORGANISM: Homo sapiens
<220> FEATURE:
<221> NAME/KEY: PEPTIDE

```
<222> LOCATION: (1)..(441)
<223> OTHER INFORMATION: Isoform Tau-F
<300> PUBLICATION INFORMATION:
<301> AUTHORS: Goedert M., Spillantini M.G., Jakes R., Rutherford D.,
       Crowther R.A.
<302> TITLE: Multiple isoforms of human microtubule-associated protein
       tau: sequences and localization in neurofibrillary tangles of
       Alzheimer's disease.
<303> JOURNAL: Neuron
<304> VOLUME: 3
<306> PAGES: 519-526
<307> DATE: 1989-10-01
<300> PUBLICATION INFORMATION:
<308> DATABASE ACCESSION NUMBER: P10636-8
<309> DATABASE ENTRY DATE: 2010-10-05
<313> RELEVANT RESIDUES IN SEQ ID NO: (1)..(441)

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320
```

-continued

```
Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

```
<210> SEQ ID NO 7
<211> LENGTH: 7
<212> TYPE: PRT
<213> ORGANISM: artificial sequence
<220> FEATURE:
<223> OTHER INFORMATION: Epitope recognized by NI-105.4E4 antibody
<220> FEATURE:
<221> NAME/KEY: PEPTIDE
<222> LOCATION: (1)..(7)
<223> OTHER INFORMATION: Epitope NI-105.4E4

<400> SEQUENCE: 7

Val Glu Val Lys Ser Glu Lys
1               5
```

```
<210> SEQ ID NO 8
<211> LENGTH: 363
<212> TYPE: DNA
<213> ORGANISM: Homo sapiens
<220> FEATURE:
<221> NAME/KEY: CDS
<222> LOCATION: (1)..(363)
<223> OTHER INFORMATION: NI-105.4E4-VH variable heavy chain (VH) sequence
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(204)
<223> OTHER INFORMATION: complementarity determining region (CDR)
      VH-CDR2
<220> FEATURE:
<221> NAME/KEY: V_region
<222> LOCATION: (301)..(330)
<223> OTHER INFORMATION: complementarity determining region (CDR)
      VH-CDR3
```

<400> SEQUENCE: 8

```
gag gtg cag ctg gtg gag tct ggg gga ggc ttg gtc cag cct ggg gga     48
Glu Val Gln Leu Val Glu Ser Gly Gly Gly Leu Val Gln Pro Gly Gly
1               5                   10                  15 tcc ctg aaa ctc tcc tgt gca gcc tct ggg ttc aat ttc aac atc tct     96
Ser Leu Lys Leu Ser Cys Ala Ala Ser Gly Phe Asn Phe Asn Ile Ser
            20                  25                  30 gct ata cac tgg gtc cgc cag gct tcc ggg aaa ggg ctg gag tgg gtt    144
Ala Ile His Trp Val Arg Gln Ala Ser Gly Lys Gly Leu Glu Trp Val
        35                  40                  45
```

```
ggc cga ata aga agt aaa tct cac aat tac gcg act tta tat gct gcg       192
Gly Arg Ile Arg Ser Lys Ser His Asn Tyr Ala Thr Leu Tyr Ala Ala
 50                  55                  60 tcc ctg aaa ggc cgg ttc acc ctc tcc aga gat gat tca agg aac acg       240
Ser Leu Lys Gly Arg Phe Thr Leu Ser Arg Asp Asp Ser Arg Asn Thr
 65                  70                  75                  80 gcg tat ctg caa atg agc agc ctg caa acc gag gat atg gcc gtc tat       288
Ala Tyr Leu Gln Met Ser Ser Leu Gln Thr Glu Asp Met Ala Val Tyr
                 85                  90                  95 tac tgt act gtt ctg agt gcg aat tac gac acc ttt gac tac tgg ggc       336
Tyr Cys Thr Val Leu Ser Ala Asn Tyr Asp Thr Phe Asp Tyr Trp Gly
            100                 105                 110 cag gga acc ctg gtc acc gtc tcc tcg                                    363
Gln Gly Thr Leu Val Thr Val Ser Ser
        115                 120
```

<210> SEQ ID NO 9
<211> LENGTH: 121
<212> TYPE: PRT
<213> ORGANISM: Homo sapiens

<400> SEQUENCE: 9

```
Glu Val Gln Leu Val Glu Ser Gly Gly Gly Leu Val Gln Pro Gly Gly
  1               5                  10                  15

Ser Leu Lys Leu Ser Cys Ala Ala Ser Gly Phe Asn Phe Asn Ile Ser
             20                  25                  30

Ala Ile His Trp Val Arg Gln Ala Ser Gly Lys Gly Leu Glu Trp Val
         35                  40                  45

Gly Arg Ile Arg Ser Lys Ser His Asn Tyr Ala Thr Leu Tyr Ala Ala
 50                  55                  60

Ser Leu Lys Gly Arg Phe Thr Leu Ser Arg Asp Asp Ser Arg Asn Thr
 65                  70                  75                  80

Ala Tyr Leu Gln Met Ser Ser Leu Gln Thr Glu Asp Met Ala Val Tyr
                 85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser
        115                 120
```

<210> SEQ ID NO 10
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION: NI-105.4E4-VL variable light chain (VL)
    sequence wherein amino acid sequence Ser-Tyr-Glu at positions 1-3
    may also be Leu-Pro-Val
<220> FEATURE:
<221> NAME/KEY: V_region
<222> LOCATION: (67)..(99)
<223> OTHER INFORMATION: complementarity determining region (CDR)
    VL-CDR1
<220> FEATURE:
<221> NAME/KEY: V_region
<222> LOCATION: (145)..(165)
<223> OTHER INFORMATION: complementarity determining region (CDR)
    VL-CDR2
<220> FEATURE:
<221> NAME/KEY: V_region
<222> LOCATION: (262)..(291)
<223> OTHER INFORMATION: complementarity determining region (CDR)
    VL-CDR3

-continued

```
<400> SEQUENCE: 10 tcc tat gag ctg act cag cca ccc tcg gtg tca gtg tcc cca gga cag      48
Ser Tyr Glu Leu Thr Gln Pro Pro Ser Val Ser Val Ser Pro Gly Gln
1               5                   10                  15 acg gcc agg atc tcc tgc ttt gga gat aca ttg cca aag caa tat act      96
Thr Ala Arg Ile Ser Cys Phe Gly Asp Thr Leu Pro Lys Gln Tyr Thr
            20                  25                  30 tat tgg tat cag cag aag cct ggc cag gcc cct gtg tta gtg att tat     144
Tyr Trp Tyr Gln Gln Lys Pro Gly Gln Ala Pro Val Leu Val Ile Tyr
        35                  40                  45 aaa gac act gag agg ccc tca ggg atc ccc gag cga ttc tct ggc tcc     192
Lys Asp Thr Glu Arg Pro Ser Gly Ile Pro Glu Arg Phe Ser Gly Ser
    50                  55                  60 agc tca ggg aca aca gtc acc ttg acc atc agt gga gtc cag gca gaa     240
Ser Ser Gly Thr Thr Val Thr Leu Thr Ile Ser Gly Val Gln Ala Glu
65                  70                  75                  80 gac gag gct gac tat tac tgt cta tca gct gac aac agt gct act tgg     288
Asp Glu Ala Asp Tyr Tyr Cys Leu Ser Ala Asp Asn Ser Ala Thr Trp
                85                  90                  95 gtg ttc ggc gga ggg acc aag gtg acc gtc cta                         321
Val Phe Gly Gly Gly Thr Lys Val Thr Val Leu
            100                 105

<210> SEQ ID NO 11
<211> LENGTH: 107
<212> TYPE: PRT
<213> ORGANISM: Homo sapiens

<400> SEQUENCE: 11

Ser Tyr Glu Leu Thr Gln Pro Pro Ser Val Ser Val Ser Pro Gly Gln
1               5                   10                  15

Thr Ala Arg Ile Ser Cys Phe Gly Asp Thr Leu Pro Lys Gln Tyr Thr
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Leu Ser Ala Asp Asn Ser Ala Thr Trp
                85                  90                  95

Val Phe Gly Gly Gly Thr Lys Val Thr Val Leu
            100                 105

<210> SEQ ID NO 12
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION: NI-105.24B2-VH variable heavy chain (VH)
      sequence wherein Gln at position 1 of the sequence may also be Glu
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
```

```
       VH-CDR2
<220> FEATURE:
<221> NAME/KEY: V_region
<222> LOCATION: (295)..(312)
<223> OTHER INFORMATION: complementarity determining region (CDR)
      VH-CDR3

<400> SEQUENCE: 12 cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tcg gtg aag gtt tcc tgt aag gca tct gga tac acc ttc gtc aat tac        96
Ser Val Lys Val Ser Cys Lys Ala Ser Gly Tyr Thr Phe Val Asn Tyr
            20                  25                  30 att ata cac tgg gtg cga cag gcc cct gga caa ggg ctt gag tgg atg       144
Ile Ile His Trp Val Arg Gln Ala Pro Gly Gln Gly Leu Glu Trp Met
        35                  40                  45 gga atc atc aat cct aat ggc gga aac aca agt tat gca gag aaa ttc       192
Gly Ile Ile Asn Pro Asn Gly Gly Asn Thr Ser Tyr Ala Glu Lys Phe
50                  55                  60 cag gcc cga gtc acc ttg acc agc gac acg tct acg agt acg gtg tac       240
Gln Ala Arg Val Thr Leu Thr Ser Asp Thr Ser Thr Ser Thr Val Tyr
65                  70                  75                  80 atg gac ctg agc agc ctg aca tct gag gac acg gcc gtc tat tac tgt       288
Met Asp Leu Ser Ser Leu Thr Ser Glu Asp Thr Ala Val Tyr Tyr Cys
                85                  90                  95 gcc gtc ctt tcc cct tcg aat ccc tgg ggc cag ggg acc acg gtc acc       336
Ala Val Leu Ser Pro Ser Asn Pro Trp Gly Gln Gly Thr Thr Val Thr
            100                 105                 110 gtc tcc tcg                                                           345
Val Ser Ser
        115

<210> SEQ ID NO 13
<211> LENGTH: 115
<212> TYPE: PRT
<213> ORGANISM: Homo sapiens

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Asn Tyr
            20                  25                  30

Ile Ile His Trp Val Arg Gln Ala Pro Gly Gln Gly Leu Glu Trp Met
        35                  40                  45

Gly Ile Ile Asn Pro Asn Gly Gly Asn Thr Ser Tyr Ala Glu Lys Phe
50                  55                  60

Gln Ala Arg Val Thr Leu Thr Ser Asp Thr Ser Thr Ser Thr Val Tyr
65                  70                  75                  80

Met Asp Leu Ser Ser Leu Thr Ser Glu Asp Thr Ala Val Tyr Tyr Cys
                85                  90                  95

Ala Val Leu Ser Pro Ser Asn Pro Trp Gly Gln Gly Thr Thr Val Thr
            100                 105                 110

Val Ser Ser
        115

<210> SEQ ID NO 14
<211> LENGTH: 324
<212> TYPE: DNA
<213> ORGANISM: Homo sapiens
<220> FEATURE:
```

-continued

```
<221> NAME/KEY: CDS
<222> LOCATION: (1)..(324)
<223> OTHER INFORMATION: NI-105.24B2-VL variable light chain (VL)
      sequence wherein Glu at position 3 in the sequence may also be Val
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 14 tcc tat gag ctg act cag cca ccc tcg gtg tca gtg tcc cca gga cag        48
Ser Tyr Glu Leu Thr Gln Pro Pro Ser Val Ser Val Ser Pro Gly Gln
1               5                   10                  15 acg gcc ggg atc acc tgc tct gga gat gct ttg cca aag caa ttt gtt        96
Thr Ala Gly Ile Thr Cys Ser Gly Asp Ala Leu Pro Lys Gln Phe Val
            20                  25                  30 tat tgg tac cag aag aag cca ggc cag gcc cct gtg tta ttg ata tat       144
Tyr Trp Tyr Gln Lys Lys Pro Gly Gln Ala Pro Val Leu Leu Ile Tyr
        35                  40                  45 aaa gac act gag agg ccc tca cga atc cct gag cgc ttc tct ggc tcc       192
Lys Asp Thr Glu Arg Pro Ser Arg Ile Pro Glu Arg Phe Ser Gly Ser
50                  55                  60 acc tca ggg aca aca gtc gcg ttg acc atc aat ggg gtc cag gca gag       240
Thr Ser Gly Thr Thr Val Ala Leu Thr Ile Asn Gly Val Gln Ala Glu
65                  70                  75                  80 gac gag gct gac tat tac tgt caa tca gcc gac cgc agt ggt gct ctt       288
Asp Glu Ala Asp Tyr Tyr Cys Gln Ser Ala Asp Arg Ser Gly Ala Leu
                85                  90                  95 tgg gtg ttc ggc gga ggg acc aag ctg acc gtc cta                       324
Trp Val Phe Gly Gly Gly Thr Lys Leu Thr Val Leu
            100                 105

<210> SEQ ID NO 15
<211> LENGTH: 108
<212> TYPE: PRT
<213> ORGANISM: Homo sapiens

<400> SEQUENCE: 15

Ser Tyr Glu Leu Thr Gln Pro Pro Ser Val Ser Val Ser Pro Gly Gln
1               5                   10                  15

Thr Ala Gly Ile Thr Cys Ser Gly Asp Ala Leu Pro Lys Gln Phe Val
            20                  25                  30

Tyr Trp Tyr Gln Lys Lys Pro Gly Gln Ala Pro Val Leu Leu Ile Tyr
        35                  40                  45

Lys Asp Thr Glu Arg Pro Ser Arg Ile Pro Glu Arg Phe Ser Gly Ser
    50                  55                  60

Thr Ser Gly Thr Thr Val Ala Leu Thr Ile Asn Gly Val Gln Ala Glu
65                  70                  75                  80

Asp Glu Ala Asp Tyr Tyr Cys Gln Ser Ala Asp Arg Ser Gly Ala Leu
                85                  90                  95

Trp Val Phe Gly Gly Gly Thr Lys Leu Thr Val Leu
            100                 105
```

<210> SEQ ID NO 16
<211> LENGTH: 378
<212> TYPE: DNA
<213> ORGANISM: Homo sapiens
<220> FEATURE:
<221> NAME/KEY: CDS
<222> LOCATION: (1)..(378)
<223> OTHER INFORMATION: NI-105.4A3-VH variable heavy chain (VH)
      sequence wherein Gln at positon 1 of the sequence may also be
      Glu and Ser at position 7 of the sequence may also be Thr
<220> FEATURE:
<221> NAME/KEY: V_region
<222> LOCATION: (91)..(105)
<223> OTHER INFORMATION: complementarity determining region (CDR)
      VH-CDR1
<220> FEATURE:
<221> NAME/KEY: V_region
<222> LOCATION: (148)..(198)
<223> OTHER INFORMATION: complementarity determining region (CDR)
      VH-CDR2
<220> FEATURE:
<221> NAME/KEY: V_region
<222> LOCATION: (295)..(345)
<223> OTHER INFORMATION: complementarity determining region (CDR)
      VH-CDR3

<400> SEQUENCE: 16

```
cag gtg cag ctg gtg gag tct ggg gga ggc gcg gtc cag cct ggg ggg      48
Gln Val Gln Leu Val Glu Ser Gly Gly Gly Ala Val Gln Pro Gly Gly
1               5                   10                  15 tcc ctg aga ctc tcc tgt gca gcc tct gga ttc acc ttc agt gac tat      96
Ser Leu Arg Leu Ser Cys Ala Ala Ser Gly Phe Thr Phe Ser Asp Tyr
            20                  25                  30 gcc atg cac tgg gtc cgc cag gct cca ggc aag ggg ctg cag tgg gtg     144
Ala Met His Trp Val Arg Gln Ala Pro Gly Lys Gly Leu Gln Trp Val
        35                  40                  45 gca gtt ata tcg tat gag gga act tat aaa tac tat gca gac tcc gtg     192
Ala Val Ile Ser Tyr Glu Gly Thr Tyr Lys Tyr Tyr Ala Asp Ser Val
    50                  55                  60 aag ggc cga ttc acc atc tcc aga gac aat tcc aag aac acg ctg aac     240
Lys Gly Arg Phe Thr Ile Ser Arg Asp Asn Ser Lys Asn Thr Leu Asn
65                  70                  75                  80 ttg cag atg agc agc ctg aga gtt gaa gac acg gct gtg tat ttc tgt     288
Leu Gln Met Ser Ser Leu Arg Val Glu Asp Thr Ala Val Tyr Phe Cys
                85                  90                  95 gtg aaa gct cga gcc ttt gcc tcc gga cag cga agc acc tcc acc gta     336
Val Lys Ala Arg Ala Phe Ala Ser Gly Gln Arg Ser Thr Ser Thr Val
            100                 105                 110 cct gac tac tgg ggc cag gga acc ctg gtc acc gtc tcc tcg             378
Pro Asp Tyr Trp Gly Gln Gly Thr Leu Val Thr Val Ser Ser
        115                 120                 125
```

<210> SEQ ID NO 17
<211> LENGTH: 126
<212> TYPE: PRT
<213> ORGANISM: Homo sapiens

<400> SEQUENCE: 17

```
Gln Val Gln Leu Val Glu Ser Gly Gly Gly Ala Val Gln Pro Gly Gly
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Gln Trp Val
        35                  40                  45

Ala Val Ile Ser Tyr Glu Gly Thr Tyr Lys Tyr Tyr Ala Asp Ser Val
```

```
                50                  55                  60
Lys Gly Arg Phe Thr Ile Ser Arg Asp Asn Ser Lys Asn Thr Leu Asn
 65                  70                  75                  80

Leu Gln Met Ser Ser Leu Arg Val Glu Asp Thr Ala Val Tyr Phe Cys
                 85                  90                  95

Val Lys Ala Arg Ala Phe Ala Ser Gly Gln Arg Ser Thr Ser Thr Val
                100                 105                 110

Pro Asp Tyr Trp Gly Gln Gly Thr Leu Val Thr Val Ser Ser
                115                 120                 125

<210> SEQ ID NO 18
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION: NI-105.4A3-VL variable light chain (VL)
      sequence
<220> FEATURE:
<221> NAME/KEY: V_region
<222> LOCATION: (67)..(99)
<223> OTHER INFORMATION: complementarity determining region (CDR)
      VL-CDR1
<220> FEATURE:
<221> NAME/KEY: V_region
<222> LOCATION: (145)..(165)
<223> OTHER INFORMATION: complementarity determining region (CDR)
      VL-CDR2
<220> FEATURE:
<221> NAME/KEY: V_region
<222> LOCATION: (262)..(294)
<223> OTHER INFORMATION: complementarity determining region (CDR)
      VL-CDR3

<400> SEQUENCE: 18 tcc tat gag ctg act cag cca ccc tcg gtg tca gtg tcc cca gga caa      48
Ser Tyr Glu Leu Thr Gln Pro Pro Ser Val Ser Val Ser Pro Gly Gln
 1               5                  10                  15 acg gcc agg atc acc tgc tct gga gat gca ttg cca aaa aaa tat gct      96
Thr Ala Arg Ile Thr Cys Ser Gly Asp Ala Leu Pro Lys Lys Tyr Ala
             20                  25                  30 tat tgg tac cag cag aag tca ggc cag gcc cct gtg ttg gtc atc tat     144
Tyr Trp Tyr Gln Gln Lys Ser Gly Gln Ala Pro Val Leu Val Ile Tyr
         35                  40                  45 gag gac aac aaa cga ccc tcc ggg atc cct gag aga ttc tct ggc tcc     192
Glu Asp Asn Lys Arg Pro Ser Gly Ile Pro Glu Arg Phe Ser Gly Ser
     50                  55                  60 agc tca ggg aca gtg gcc acc ttg act atc agt ggg gcc cag gtg gac     240
Ser Ser Gly Thr Val Ala Thr Leu Thr Ile Ser Gly Ala Gln Val Asp
 65                  70                  75                  80 gat gaa gct gac tac tac tgc tac tcg aca gac atc agt ggt gac ctt     288
Asp Glu Ala Asp Tyr Tyr Cys Tyr Ser Thr Asp Ile Ser Gly Asp Leu
                 85                  90                  95 cgg gtg ttc ggc gga ggg acc aag ctg acc gtc ctc                     324
Arg Val Phe Gly Gly Gly Thr Lys Leu Thr Val Leu
                100                 105

<210> SEQ ID NO 19
<211> LENGTH: 108
<212> TYPE: PRT
<213> ORGANISM: Homo sapiens

<400> SEQUENCE: 19

Ser Tyr Glu Leu Thr Gln Pro Pro Ser Val Ser Val Ser Pro Gly Gln
```

```
              1               5                  10                 15
              Thr Ala Arg Ile Thr Cys Ser Gly Asp Ala Leu Pro Lys Lys Tyr Ala
                              20                 25                 30

Tyr Trp Tyr Gln Gln Lys Ser Gly Gln Ala Pro Val Leu Val Ile Tyr
                              35                 40                 45

Glu Asp Asn Lys Arg Pro Ser Gly Ile Pro Glu Arg Phe Ser Gly Ser
                              50                 55                 60

Ser Gly Thr Val Ala Thr Leu Thr Ile Ser Gly Ala Gln Val Asp
              65                  70                 75                 80

Asp Glu Ala Asp Tyr Tyr Cys Tyr Ser Thr Asp Ile Ser Gly Asp Leu
                              85                 90                 95

Arg Val Phe Gly Gly Gly Thr Lys Leu Thr Val Leu
                              100                105

<210> SEQ ID NO 20
<211> LENGTH: 451
<212> TYPE: PRT
<213> ORGANISM: Artificial sequence
<220> FEATURE:
<223> OTHER INFORMATION: mature ch4E4 heavy chain (mouse IgG2a)

<400> SEQUENCE: 20

Glu Val Gln Leu Val Glu Ser Gly Gly Gly Leu Val Gln Pro Gly Gly
1               5                  10                 15

Ser Leu Lys Leu Ser Cys Ala Ala Ser Gly Phe Asn Phe Asn Ile Ser
                20                 25                 30

Ala Ile His Trp Val Arg Gln Ala Ser Gly Lys Gly Leu Glu Trp Val
                35                 40                 45

Gly Arg Ile Arg Ser Lys Ser His Asn Tyr Ala Thr Leu Tyr Ala Ala
                50                 55                 60

Ser Leu Lys Gly Arg Phe Thr Leu Ser Arg Asp Asp Ser Arg Asn Thr
65                  70                 75                 80

Ala Tyr Leu Gln Met Ser Ser Leu Gln Thr Glu Asp Met Ala Val Tyr
                85                 90                 95

Tyr Cys Thr Val Leu Ser Ala Asn Tyr Asp Thr Phe Asp Tyr Trp Gly
                100                105                110

Gln Gly Thr Leu Val Thr Val Ser Ser Ala Lys Thr Thr Ala Pro Ser
                115                120                125

Val Tyr Pro Leu Ala Pro Val Cys Gly Asp Thr Thr Gly Ser Ser Val
                130                135                140

Thr Leu Gly Cys Leu Val Lys Gly Tyr Phe Pro Glu Pro Val Thr Leu
145                 150                155                160

Thr Trp Asn Ser Gly Ser Leu Ser Ser Gly Val His Thr Phe Pro Ala
                165                170                175

Val Leu Gln Ser Asp Leu Tyr Thr Leu Ser Ser Ser Val Thr Val Thr
                180                185                190

Ser Ser Thr Trp Pro Ser Gln Ser Ile Thr Cys Asn Val Ala His Pro
                195                200                205

Ala Ser Ser Thr Lys Val Asp Lys Lys Ile Glu Pro Arg Gly Pro Thr
                210                215                220

Ile Lys Pro Cys Pro Pro Cys Lys Cys Pro Ala Pro Asn Leu Leu Gly
225                 230                235                240

Gly Pro Ser Val Phe Ile Phe Pro Pro Lys Ile Lys Asp Val Leu Met
                245                250                255

Ile Ser Leu Ser Pro Ile Val Thr Cys Val Val Val Asp Val Ser Glu
```

```
            260                 265                 270
Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
                340                 345                 350

Tyr Val Leu Pro Pro Glu Glu Met Thr Lys Lys Gln Val Thr
                355                 360                 365

Leu Thr Cys Met Val Thr Asp Phe Met Pro Glu Asp Ile Tyr Val Glu
                370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
                420                 425                 430

His Glu Gly Leu His Asn His His Thr Thr Lys Ser Phe Ser Arg Thr
                435                 440                 445

Pro Gly Lys
        450

<210> SEQ ID NO 21
<211> LENGTH: 213
<212> TYPE: PRT
<213> ORGANISM: Artificial sequence
<220> FEATURE:
<223> OTHER INFORMATION: mature ch4E4 light chain (mouse lambda)

<400> SEQUENCE: 21

Ser Tyr Glu Leu Thr Gln Pro Pro Ser Val Ser Val Ser Pro Gly Gln
1               5                   10                  15

Thr Ala Arg Ile Ser Cys Phe Gly Asp Thr Leu Pro Lys Gln Tyr Thr
                20                  25                  30

Tyr Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Leu Ser Ala Asp Asn Ser Ala Thr Trp
                85                  90                  95

Val Phe Gly Gly Gly Thr Lys Val Thr Val Leu Gly Gln Pro Lys Ser
            100                 105                 110

Ser Pro Ser Val Thr Leu Phe Pro Pro Ser Ser Glu Glu Leu Glu Thr
            115                 120                 125

Asn Lys Ala Thr Leu Val Cys Thr Ile Thr Asp Phe Tyr Pro Gly Val
            130                 135                 140

Val Thr Val Asp Trp Lys Val Asp Gly Thr Pro Val Thr Gln Gly Met
145                 150                 155                 160

Glu Thr Thr Gln Pro Ser Lys Gln Ser Asn Asn Lys Tyr Met Ala Ser
```

```
                    165                 170                 175

Ser Tyr Leu Thr Leu Thr Ala Arg Ala Trp Glu Arg His Ser Ser Tyr
            180                 185                 190

Ser Cys Gln Val Thr His Glu Gly His Thr Val Glu Lys Ser Leu Ser
        195                 200                 205

Arg Ala Asp Cys Ser
    210

<210> SEQ ID NO 22
<211> LENGTH: 451
<212> TYPE: PRT
<213> ORGANISM: Artificial sequence
<220> FEATURE:
<223> OTHER INFORMATION: mature ch4E4(N30Q) heavy chain (mouse IgG2a)

<400> SEQUENCE: 22

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Gln Ile Ser
            20                  25                  30

Ala Ile His Trp Val Arg Gln Ala Ser Gly Lys Gly Leu Glu Trp Val
        35                  40                  45

Gly Arg Ile Arg Ser Lys Ser His Asn Tyr Ala Thr Leu Tyr Ala Ala
    50                  55                  60

Ser Leu Lys Gly Arg Phe Thr Leu Ser Arg Asp Ser Arg Asn Thr
65                  70                  75                  80

Ala Tyr Leu Gln Met Ser Ser Leu Gln Thr Glu Asp Met Ala Val Tyr
                85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
```

```
                305                 310                 315                 320
        Lys Glu Phe Lys Cys Lys Val Asn Asn Lys Asp Leu Pro Ala Pro Ile
                        325                 330                 335

Glu Arg Thr Ile Ser Lys Pro Lys Gly Ser Val Arg Ala Pro Gln Val
                        340                 345                 350

Tyr Val Leu Pro Pro Glu Glu Met Thr Lys Lys Gln Val Thr
                        355                 360                 365

Leu Thr Cys Met Val Thr Asp Phe Met Pro Glu Asp Ile Tyr Val Glu
                        370                 375                 380

Trp Thr Asn Asn Gly Lys Thr Glu Leu Asn Tyr Lys Asn Thr Glu Pro
        385                 390                 395                 400

Val Leu Asp Ser Asp Gly Ser Tyr Phe Met Tyr Ser Lys Leu Arg Val
                        405                 410                 415

Glu Lys Lys Asn Trp Val Glu Arg Asn Ser Tyr Ser Cys Ser Val Val
                        420                 425                 430

His Glu Gly Leu His Asn His His Thr Thr Lys Ser Phe Ser Arg Thr
                        435                 440                 445

Pro Gly Lys
                450

<210> SEQ ID NO 23
<211> LENGTH: 5
<212> TYPE: PRT
<213> ORGANISM: Artificial sequence
<220> FEATURE:
<223> OTHER INFORMATION: NI-105.4E4-VH (variable heavy chain sequence
      VH) CDR1

<400> SEQUENCE: 23

Ile Ser Ala Ile His
1               5

<210> SEQ ID NO 24
<211> LENGTH: 19
<212> TYPE: PRT
<213> ORGANISM: Artificial sequence
<220> FEATURE:
<223> OTHER INFORMATION: NI-105.4E4-VH (variable heavy chain sequence
      VH) CDR2

<400> SEQUENCE: 24

Arg Ile Arg Ser Lys Ser His Asn Tyr Ala Thr Leu Tyr Ala Ala Ser
1               5                   10                  15

Leu Lys Gly

<210> SEQ ID NO 25
<211> LENGTH: 10
<212> TYPE: PRT
<213> ORGANISM: Artificial sequence
<220> FEATURE:
<223> OTHER INFORMATION: NI-105.4E4-VH (variable heavy chain sequence
      VH) CDR3

<400> SEQUENCE: 25

Leu Ser Ala Asn Tyr Asp Thr Phe Asp Tyr
1               5                   10

<210> SEQ ID NO 26
<211> LENGTH: 11
<212> TYPE: PRT
<213> ORGANISM: Artificial sequence
<220> FEATURE:
```

<223> OTHER INFORMATION: NI-105.4E4-VL (variable light chain sequence
      VL) CDR1

<400> SEQUENCE: 26

Phe Gly Asp Thr Leu Pro Lys Gln Tyr Thr Tyr
1               5                   10

<210> SEQ ID NO 27
<211> LENGTH: 7
<212> TYPE: PRT
<213> ORGANISM: Artificial sequence
<220> FEATURE:
<223> OTHER INFORMATION: NI-105.4E4-VL (variable light chain sequence
      VL) CDR2

<400> SEQUENCE: 27

Lys Asp Thr Glu Arg Pro Ser
1               5

<210> SEQ ID NO 28
<211> LENGTH: 10
<212> TYPE: PRT
<213> ORGANISM: Artificial sequence
<220> FEATURE:
<223> OTHER INFORMATION: NI-105.4E4-VL (variable light chain sequence
      VL) CD3

<400> SEQUENCE: 28

Leu Ser Ala Asp Asn Ser Ala Thr Trp Val
1               5                   10

<210> SEQ ID NO 29
<211> LENGTH: 5
<212> TYPE: PRT
<213> ORGANISM: Artificial sequence
<220> FEATURE:
<223> OTHER INFORMATION: NI-105.24B2-VH (variable heavy chain sequence
      VH) CDR1

<400> SEQUENCE: 29

Asn Tyr Ile Ile His
1               5

<210> SEQ ID NO 30
<211> LENGTH: 17
<212> TYPE: PRT
<213> ORGANISM: Artificial sequence
<220> FEATURE:
<223> OTHER INFORMATION: NI-105.24B2-VH (variable heavy chain sequence
      VH) CD2

<400> SEQUENCE: 30

Ile Ile Asn Pro Asn Gly Gly Asn Thr Ser Tyr Ala Glu Lys Phe Gln
1               5                   10                  15

Ala

<210> SEQ ID NO 31
<211> LENGTH: 6
<212> TYPE: PRT
<213> ORGANISM: Artificial sequence
<220> FEATURE:
<223> OTHER INFORMATION: NI-105.24B2-VH (variable heavy chain sequence
      VH) CDR3

<400> SEQUENCE: 31

Leu Ser Pro Ser Asn Pro
1               5

<210> SEQ ID NO 32
<211> LENGTH: 11
<212> TYPE: PRT
<213> ORGANISM: Artificial sequence
<220> FEATURE:
<223> OTHER INFORMATION: NI-105.24B2-VL (variable light chain sequence
      VL) CDR1

<400> SEQUENCE: 32

Ser Gly Asp Ala Leu Pro Lys Gln Phe Val Tyr
1               5                   10

<210> SEQ ID NO 33
<211> LENGTH: 7
<212> TYPE: PRT
<213> ORGANISM: Artificial sequence
<220> FEATURE:
<223> OTHER INFORMATION: NI-105.24B2-VL (variable light chain sequence
      VL) CDR2

<400> SEQUENCE: 33

Lys Asp Thr Glu Arg Pro Ser
1               5

<210> SEQ ID NO 34
<211> LENGTH: 11
<212> TYPE: PRT
<213> ORGANISM: Artificial sequence
<220> FEATURE:
<223> OTHER INFORMATION: NI-105.24B2-VL (variable light chain sequence
      VL) CDR3

<400> SEQUENCE: 34

Gln Ser Ala Asp Arg Ser Gly Ala Leu Trp Val
1               5                   10

<210> SEQ ID NO 35
<211> LENGTH: 5
<212> TYPE: PRT
<213> ORGANISM: Artificial sequence
<220> FEATURE:
<223> OTHER INFORMATION: NI-105.4A3-VH (variable heavy chain sequence
      VH) CDR1

<400> SEQUENCE: 35

Asp Tyr Ala Met His
1               5

<210> SEQ ID NO 36
<211> LENGTH: 17
<212> TYPE: PRT
<213> ORGANISM: Artificial sequence
<220> FEATURE:
<223> OTHER INFORMATION: NI-105.4A3-VH (variable heavy chain sequence
      VH) CDR2

<400> SEQUENCE: 36

Val Ile Ser Tyr Glu Gly Thr Tyr Lys Tyr Tyr Ala Asp Ser Val Lys
1               5                   10                  15

Gly

<210> SEQ ID NO 37
<211> LENGTH: 17
<212> TYPE: PRT
<213> ORGANISM: Artificial sequence
<220> FEATURE:

```
<223> OTHER INFORMATION: NI-105.4A3-VH (variable heavy chain sequence
      VH) CDR3

<400> SEQUENCE: 37

Ala Arg Ala Phe Ala Ser Gly Gln Arg Ser Thr Ser Thr Val Pro Asp
1               5                   10                  15

Tyr

<210> SEQ ID NO 38
<211> LENGTH: 11
<212> TYPE: PRT
<213> ORGANISM: Artificial sequence
<220> FEATURE:
<223> OTHER INFORMATION: NI-105.4A3-VL (variable light chain sequence
      VL) CDR1

<400> SEQUENCE: 38

Ser Gly Asp Ala Leu Pro Lys Lys Tyr Ala Tyr
1               5                   10

<210> SEQ ID NO 39
<211> LENGTH: 7
<212> TYPE: PRT
<213> ORGANISM: Artificial sequence
<220> FEATURE:
<223> OTHER INFORMATION: NI-105.4A3-VL (variable light chain sequence
      VL) CDR2

<400> SEQUENCE: 39

Glu Asp Asn Lys Arg Pro Ser
1               5

<210> SEQ ID NO 40
<211> LENGTH: 11
<212> TYPE: PRT
<213> ORGANISM: Artificial sequence
<220> FEATURE:
<223> OTHER INFORMATION: NI-105.4A3-VL (variable light chain sequence
      VL) CDR3

<400> SEQUENCE: 40

Tyr Ser Thr Asp Ile Ser Gly Asp Leu Arg Val
1               5                   10

<210> SEQ ID NO 41
<211> LENGTH: 11
<212> TYPE: PRT
<213> ORGANISM: Artificial sequence
<220> FEATURE:
<223> OTHER INFORMATION: Peptide

<400> SEQUENCE: 41

Asp His Gly Ala Glu Ile Val Tyr Lys Ser Pro
1               5                   10

<210> SEQ ID NO 42
<211> LENGTH: 15
<212> TYPE: PRT
<213> ORGANISM: Artificial sequence
<220> FEATURE:
<223> OTHER INFORMATION: Peptide

<400> SEQUENCE: 42

Gln Glu Gly Asp Thr Asp Ala Gly Leu Lys Glu Ser Pro Leu Gln
1               5                   10                  15
```

-continued

```
<210> SEQ ID NO 43
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 43

Gly Gln Val Glu Val Lys Ser Glu Lys Leu Asp Phe Lys Asp Arg
1               5                   10                  15

<210> SEQ ID NO 44
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 44

Ala Gln Val Glu Val Lys Ser Glu Lys Leu Asp Phe Lys Asp Arg
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 45

Gly Ala Val Glu Val Lys Ser Glu Lys Leu Asp Phe Lys Asp Arg
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 46

Gly Gln Ala Glu Val Lys Ser Glu Lys Leu Asp Phe Lys Asp Arg
1               5                   10                  15

<210> SEQ ID NO 47
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 47

Gly Gln Val Ala Val Lys Ser Glu Lys Leu Asp Phe Lys Asp Arg
1               5                   10                  15

<210> SEQ ID NO 48
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 48

Gly Gln Val Glu Ala Lys Ser Glu Lys Leu Asp Phe Lys Asp Arg
1               5                   10                  15

<210> SEQ ID NO 49
```

<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 49

Gly Gln Val Glu Val Ala Ser Glu Lys Leu Asp Phe Lys Asp Arg
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 50

Gly Gln Val Glu Val Lys Ala Glu Lys Leu Asp Phe Lys Asp Arg
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 51

Gly Gln Val Glu Val Lys Ser Ala Lys Leu Asp Phe Lys Asp Arg
1               5                   10                  15

<210> SEQ ID NO 52
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 52

Gly Gln Val Glu Val Lys Ser Glu Ala Leu Asp Phe Lys Asp Arg
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 53

Gly Gln Val Glu Val Lys Ser Glu Lys Ala Asp Phe Lys Asp Arg
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 54

Gly Gln Val Glu Val Lys Ser Glu Lys Leu Ala Phe Lys Asp Arg
1               5                   10                  15

<210> SEQ ID NO 55
<211> LENGTH: 15

-continued

<212> TYPE: PRT
<213> ORGANISM: Artificial sequence
<220> FEATURE:
<223> OTHER INFORMATION: Alanine mutagenesis 4E4 epitope

<400> SEQUENCE: 55

Gly Gln Val Glu Val Lys Ser Glu Lys Leu Asp Ala Lys Asp Arg
1 5 10 15

<210> SEQ ID NO 56
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 56

Gly Gln Val Glu Val Lys Ser Glu Lys Leu Asp Phe Ala Asp Arg
1 5 10 15

<210> SEQ ID NO 57
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 57

Gly Gln Val Glu Val Lys Ser Glu Lys Leu Asp Phe Lys Ala Arg
1 5 10 15

<210> SEQ ID NO 58
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 58

Gly Gln Val Glu Val Lys Ser Glu Lys Leu Asp Phe Lys Asp Ala
1 5 10 15

<210> SEQ ID NO 59
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 59

Lys Ala Lys Thr Asp His Gly Ala Glu Ile Val Tyr Lys Ser Pro
1 5 10 15

<210> SEQ ID NO 60
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 60

Ala Ala Lys Thr Asp His Gly Ala Glu Ile Val Tyr Lys Ser Pro
1 5 10 15

<210> SEQ ID NO 61
<211> LENGTH: 15
<212> TYPE: PRT

```
<213> ORGANISM: Artificial sequence
<220> FEATURE:
<223> OTHER INFORMATION: Alanine mutagenesis 4E4 epitope

<400> SEQUENCE: 61

Lys Gly Lys Thr Asp His Gly Ala Glu Ile Val Tyr Lys Ser Pro
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 62

Lys Pro Lys Thr Asp His Gly Ala Glu Ile Val Tyr Lys Ser Pro
1               5                   10                  15

<210> SEQ ID NO 63
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 63

Lys Ala Ala Thr Asp His Gly Ala Glu Ile Val Tyr Lys Ser Pro
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 64

Lys Ala Lys Ala Asp His Gly Ala Glu Ile Val Tyr Lys Ser Pro
1               5                   10                  15

<210> SEQ ID NO 65
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 65

Lys Ala Lys Thr Ala His Gly Ala Glu Ile Val Tyr Lys Ser Pro
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 66

Lys Ala Lys Thr Asp Ala Gly Ala Glu Ile Val Tyr Lys Ser Pro
1               5                   10                  15

<210> SEQ ID NO 67
<211> LENGTH: 15
<212> TYPE: PRT
<213> ORGANISM: Artificial sequence
```

```
<220> FEATURE:
<223> OTHER INFORMATION: Alanine mutagenesis 4E4 epitope

<400> SEQUENCE: 67

Lys Ala Lys Thr Asp His Ala Ala Glu Ile Val Tyr Lys Ser Pro
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 68

Lys Ala Lys Thr Asp His Gly Gly Glu Ile Val Tyr Lys Ser Pro
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 69

Lys Ala Lys Thr Asp His Gly Pro Glu Ile Val Tyr Lys Ser Pro
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 70

Lys Ala Lys Thr Asp His Gly Ala Ala Ile Val Tyr Lys Ser Pro
1               5                   10                  15

<210> SEQ ID NO 71
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 71

Lys Ala Lys Thr Asp His Gly Ala Glu Ala Val Tyr Lys Ser Pro
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 72

Lys Ala Lys Thr Asp His Gly Ala Glu Ile Ala Tyr Lys Ser Pro
1               5                   10                  15

<210> SEQ ID NO 73
<211> LENGTH: 15
<212> TYPE: PRT
<213> ORGANISM: Artificial sequence
<220> FEATURE:
```

<223> OTHER INFORMATION: Alanine mutagenesis 4E4 epitope

<400> SEQUENCE: 73

Lys Ala Lys Thr Asp His Gly Ala Glu Ile Val Ala Lys Ser Pro
1 5 10 15

<210> SEQ ID NO 74
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 74

Lys Ala Lys Thr Asp His Gly Ala Glu Ile Val Tyr Ala Ser Pro
1 5 10 15

<210> SEQ ID NO 75
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 75

Lys Ala Lys Thr Asp His Gly Ala Glu Ile Val Tyr Lys Ala Pro
1 5 10 15

<210> SEQ ID NO 76
<211> LENGTH: 15
<212> TYPE: PRT
<213> ORGANISM: Artificial sequence
<220> FEATURE:
<223> OTHER INFORMATION: Alanine mutagenesis 4E4 epitope

<400> SEQUENCE: 76

Lys Ala Lys Thr Asp His Gly Ala Glu Ile Val Tyr Lys Ser Ala
1 5 10 15

<210> SEQ ID NO 77
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 77

Ala Glu Gly Asp Thr Asp Ala Gly Leu Lys Glu Ser Pro Leu Gln
1 5 10 15

<210> SEQ ID NO 78
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 78

Gln Ala Gly Asp Thr Asp Ala Gly Leu Lys Glu Ser Pro Leu Gln
1 5 10 15

<210> SEQ ID NO 79
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 79

Gln Glu Ala Asp Thr Asp Ala Gly Leu Lys Glu Ser Pro Leu Gln
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 80

Gln Glu Gly Ala Thr Asp Ala Gly Leu Lys Glu Ser Pro Leu Gln
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 81

Gln Glu Gly Asp Ala Asp Ala Gly Leu Lys Glu Ser Pro Leu Gln
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 82

Gln Glu Gly Asp Thr Ala Ala Gly Leu Lys Glu Ser Pro Leu Gln
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 83

Gln Glu Gly Asp Thr Asp Gly Gly Leu Lys Glu Ser Pro Leu Gln
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 84

Gln Glu Gly Asp Thr Asp Pro Gly Leu Lys Glu Ser Pro Leu Gln
1               5                   10                  15

<210> SEQ ID NO 85
<211> LENGTH: 15
<212> TYPE: PRT
<213> ORGANISM: Artificial sequence
<220> FEATURE:
<223> OTHER INFORMATION: Alanine Mutagenesis -continued

<400> SEQUENCE: 85

Gln Glu Gly Asp Thr Asp Ala Ala Leu Lys Glu Ser Pro Leu Gln
1               5                   10                  15

<210> SEQ ID NO 86
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 86

Gln Glu Gly Asp Thr Asp Ala Gly Ala Lys Glu Ser Pro Leu Gln
1               5                   10                  15

<210> SEQ ID NO 87
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 87

Gln Glu Gly Asp Thr Asp Ala Gly Leu Ala Glu Ser Pro Leu Gln
1               5                   10                  15

<210> SEQ ID NO 88
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 88

Gln Glu Gly Asp Thr Asp Ala Gly Leu Lys Ala Ser Pro Leu Gln
1               5                   10                  15

<210> SEQ ID NO 89
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 89

Gln Glu Gly Asp Thr Asp Ala Gly Leu Lys Glu Ala Pro Leu Gln
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 90

Gln Glu Gly Asp Thr Asp Ala Gly Leu Lys Glu Ser Ala Leu Gln
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 91

-continued

```
Gln Glu Gly Asp Thr Asp Ala Gly Leu Lys Glu Ser Pro Ala Gln
1               5                   10                  15

<210> SEQ ID NO 92
<211> LENGTH: 15
<212> TYPE: PRT
<213> ORGANISM: Artificial sequence
<220> FEATURE:
<223> OTHER INFORMATION: Alanine Mutagenesis

<400> SEQUENCE: 92

Gln Glu Gly Asp Thr Asp Ala Gly Leu Lys Glu Ser Pro Leu Ala
1               5                   10                  15

<210> SEQ ID NO 93
<211> LENGTH: 121
<212> TYPE: PRT
<213> ORGANISM: Artificial sequence
<220> FEATURE:
<223> OTHER INFORMATION: VH antibody

<400> SEQUENCE: 93

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asn Phe Gln Ile Ser
                20                  25                  30

Ala Ile His Trp Val Arg Gln Ala Ser Gly Lys Gly Leu Glu Trp Val
            35                  40                  45

Gly Arg Ile Arg Ser Lys Ser His Asn Tyr Ala Thr Leu Tyr Ala Ala
        50                  55                  60

Ser Leu Lys Gly Arg Phe Thr Leu Ser Arg Asp Asp Ser Arg Asn Thr
65                  70                  75                  80

Ala Tyr Leu Gln Met Ser Ser Leu Gln Thr Glu Asp Met Ala Val Tyr
                85                  90                  95

Tyr Cys Thr Val Leu Ser Ala Asn Tyr Asp Thr Phe Asp Tyr Trp Gly
            100                 105                 110

Gln Gly Thr Leu Val Thr Val Ser Ser
        115                 120
```

HUMAN ANTI-TAU ANTIBODIES

CROSS REFERENCE TO RELATED APPLICATIONS

This application claims the benefit of U.S. Provisional Application No. 61/391,751, filed Oct. 11, 2010, and EP Application No. 10013494.9, filed Oct. 11, 2010, each of which is herein incorporated by reference.

REFERENCE TO A SEQUENCE LISTING SUBMITTED ELECTRONICALLY VIA EFS-WEB

The content of the electronically submitted sequence listing (Name: sequencelisting_ascii.txt, Size: 71 kilobytes; and Date of Creation: Oct. 11, 2011) is herein incorporated by reference in its entirety.

BACKGROUND OF THE INVENTION

Field of the Invention

The present invention generally relates to novel tau-specific binding molecules, particularly human antibodies as well as fragments, derivatives and variants thereof that recognize the tau protein, including pathologically phosphorylated tau and aggregated forms of tau. In addition, the present invention relates to pharmaceutical and diagnostic compositions comprising such binding molecules, antibodies and mimics thereof valuable both as a diagnostic tool to identify tau and toxic tau species in plasma and CSF and also in passive vaccination strategies for treating neurodegenerative tauopathies such as Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, corticobasal degeneration (CBD), Creutzfeldt-Jakob disease (CJD), dementia pugilistica, diffuse neurofibrillary tangles with calcification, Down's syndrome, frontotemporal dementia, frontotemporal dementia with parkinsonism linked to chromosome 17 (FTDP-17), frontotemporal lobar degeneration, Gerstmann-Sträussler-Scheinker disease, Hallervorden-Spatz disease, inclusion body myositis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia, multi-infarct dementia and ischemic stroke.

Background Art

Protein accumulation, modifications and aggregation are pathological aspects of numerous neurodegenerative diseases. Pathologically modified and aggregated tau including hyperphosphorylated tau conformers are an invariant hallmark of tauopathies and correlate with disease severity.

Tau is a microtubule-associated protein expressed in the central nervous system with a primary function to stabilize microtubules. There are six major isoforms of tau expressed in the adult human brain, which are derived from a single gene by alternative splicing. Under pathological conditions, the tau protein becomes hyperphosphorylated, resulting in a loss of tubulin binding and destabilization of microtubules followed by the aggregation and deposition of tau in pathogenic neurofibrillary tangles. Disorders related to tau—collectively referred to as neurodegenerative tauopathies—are part of a group of protein misfolding disorders including Alzheimer's disease (AD), progressive supranuclear palsy, Pick's disease, corticabasal degeneration, FTDP-17 among others. More than 40 mutations in tau gene have been reported to be associated with hereditary frontotemporal dementia demonstrating that tau gene mutations are sufficient to trigger neurodegeneration (Cairns et al., Am. J. Pathol. 171 (2007), 227-40). Studies in transgenic mice and cell culture indicate that in AD, tau pathology may be caused by a pathological cascade in which Aβ lies upstream of tau (Götz et al., Science 293 (2001), 1491-1495). Other finding however point to a dual-pathway model where both cascades function independently of each other (van de Nes et al., Acta Neuropathol. 111 (2006), 126-138) Immunotherapies targeting the beta-amyloid peptide in AD have produced encouraging results in animal models and shown promise in clinical trials. More recent autopsy data from a small number of subjects suggests that clearance of beta-amyloid plaques in patients with progressed AD may not be sufficient to halt cognitive deterioration, emphasizing the need for additional therapeutic strategies for AD (Holmes et al., Lancet 372 (2008), 216-223; Boche et al., Acta Neuropathol. 120 (2010), 13-20). In the wake of the success of Abeta-based immunization therapy in transgenic animal models, the concept of active immunotherapy was expanded to the tau protein. Active vaccination of wild type mice using the tau protein was however found to induce the formation of neurofibrillary tangles, axonal damage and mononuclear infiltrates in the central nervous system, accompanied by neurologic deficits (Rosenmann et al., Arch Neurol. 63 (2006), 1459-1467). Subsequent studies in transgenic mouse lines using active vaccination with phosphorylated tau peptides revealed reduced brain levels of tau aggregates in the brain and slowed progression of behavior impairments (Sigurdsson, J. Alzheimers. Dis. 15 (2008), 157-168; Boimel et al., Exp. Neurol. 224 (2010), 472-485). These findings highlight the potential benefit but also the tremendous risks associated with active immunotherapy approaches targeting tau. Novel therapeutic strategies are urgently needed addressing pathological tau proteins with efficacious and safe therapy.

Passive immunization with human antibodies derived from healthy human subjects which are evolutionarily optimized and affinity matured by the human immune system would provide a promising new therapeutic avenue with a high probability for excellent efficacy and safety.

BRIEF SUMMARY OF THE INVENTION

The present invention makes use of the tau-specific immune response of healthy human subjects for the isolation of natural anti-tau specific human monoclonal antibodies. In particular, experiments performed in accordance with the present invention were successful in the isolation of monoclonal tau-specific antibodies from a pool of healthy human subjects with no signs of a neurodegenerative tauopathy.

The present invention is thus directed to human antibodies, antigen-binding fragments and similar antigen-binding molecules which are capable of specifically recognizing tau. By "specifically recognizing tau", "antibody specific to/for tau" and "anti-tau antibody" is meant specifically, generally, and collectively, antibodies to the native form of tau, or aggregated or pathologically modified tau isoforms. Provided herein are human antibodies selective for full-length, pathologically phosphorylated and aggregated forms.

In a particular embodiment of the present invention, the human antibody or antigen-binding fragment thereof demonstrates the immunological binding characteristics of an antibody characterized by the variable regions $V_H$ and/or $V_L$ as set forth in FIG. 1.

The antigen-binding fragment of the antibody can be a single chain Fv fragment, an F(ab') fragment, an F(ab) fragment, and an F(ab')$_2$ fragment, or any other antigen-binding fragment. In a specific embodiment, infra, the antibody or fragment thereof is a human IgG isotype antibody. Alternatively, the antibody is a chimeric human-murine or murinized antibody, the latter being particularly useful for diagnostic methods and studies in animals.

Furthermore, the present invention relates to compositions comprising the antibody of the present invention or active fragments thereof, or agonists and cognate molecules, or alternately, antagonists of the same and to immunotherapeutic and immunodiagnostic methods using such compositions in the prevention, diagnosis or treatment of a tauopathy, wherein an effective amount of the composition is administered to a patient in need thereof.

Naturally, the present invention extends to the immortalized human B memory lymphocyte and B cell, respectively, that produces the antibody having the distinct and unique characteristics as defined below.

The present invention also relates to polynucleotides encoding at least a variable region of an immunoglobulin chain of the antibody of the invention. In one embodiment, said variable region comprises at least one complementarity determining region (CDR) of the $V_H$ and/or $V_L$ of the variable region as set forth in FIG. 1.

Accordingly, the present invention also encompasses vectors comprising said polynucleotides and host cells transformed therewith as well as their use for the production of an antibody and equivalent binding molecules which are specific for tau. Means and methods for the recombinant production of antibodies and mimics thereof as well as methods of screening for competing binding molecules, which may or may not be antibodies, are known in the art. However, as described herein, in particular with respect to therapeutic applications in human the antibody of the present invention is a human antibody in the sense that application of said antibody is substantially free of an immune response directed against such antibody otherwise observed for chimeric and even humanized antibodies.

Furthermore, disclosed herein are compositions and methods that can be used to identify tau in samples. The disclosed anti-tau antibodies can be used to screen human blood, CSF, and urine for the presence of tau in samples, for example, by using ELISA-based or surface adapted assay. The methods and compositions disclosed herein can aid in neurodegenerative tauopathies such as Alzheimer's disease diagnosis and can be used to monitor disease progression and therapeutic efficacy.

Hence, it is a particular object of the present invention to provide methods for treating, diagnosing or preventing a neurodegenerative tauopathy such as Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke. The methods comprise administering an effective concentration of a human antibody or antibody derivative to the subject where the antibody targets tau.

Further embodiments of the present invention will be apparent from the description and Examples that follow.

BRIEF DESCRIPTION OF THE DRAWINGS

FIG. 1: Amino acid and nucleotide sequences of the variable region, i.e. heavy chain and kappa/lambda light chain of human antibodies NI-105-4E4 (A), NI-105-24B2 (B) and NI-105.4A3 (C). Framework (FR) and complementarity determining regions (CDRs) are indicated with the CDRs being underlined. Due to the cloning strategy the amino acid sequence at the N-terminus of the heavy chain and light chain may potentially contain primer-induced alterations in FR1, which however do not substantially affect the biological activity of the antibody. In order to provide a consensus human antibody, the nucleotide and amino acid sequences of the original clone were aligned with and tuned in accordance with the pertinent human germ line variable region sequences in the database; see, e.g., Vbase (http://vbase.mrc-cpe.cam.ac.uk/) hosted by the MRC Centre for Protein Engineering (Cambridge, UK). Those amino acids, which are considered to potentially deviate from the consensus germ line sequence due to the PCR primer and thus have been replaced in the amino acid sequence, are indicated in bold.

FIGS. 4A, 4B, 4C, 4D and 4E: Mapping of the N1-105.4E4 binding epitope on hTau40. PepSpot (JPT) technology: Two groups of adjacent peptide spots (peptide 83, 84 and 85; peptide 96 and 97) were specifically identified by NII05.4E4 (FIG. 4A and FIG. 4A'), when compared to the detection antibody only (FIG. 4B). The HRP-conjugated goat anti-human IgG detection antibody alone produces a strong signal on single spot (peptide 50) but does not detect peptides 83, 84, 85, 96 and 97. Alanine scanning: (FIG. 4C) Spots #35-50 and #51-68 contain the original peptides (spots #35 and #51) and their substituted variants (#36-50 and #52-68) (FIGS. 4D and 4E) Amino acid sequence of the original and substituted peptides (#35-50 and #51-68). Alanine scan suggests residues V339, E342, D387, E391 and K395 contribute to N1-105.4E4 binding.

FIG. 14: NI-105.4A3 epitope mapping with PepSpot (JPT) technology (A and B) and alanine scanning (C).

DETAILED DESCRIPTION OF THE INVENTION

I. Definitions

Figure 2:
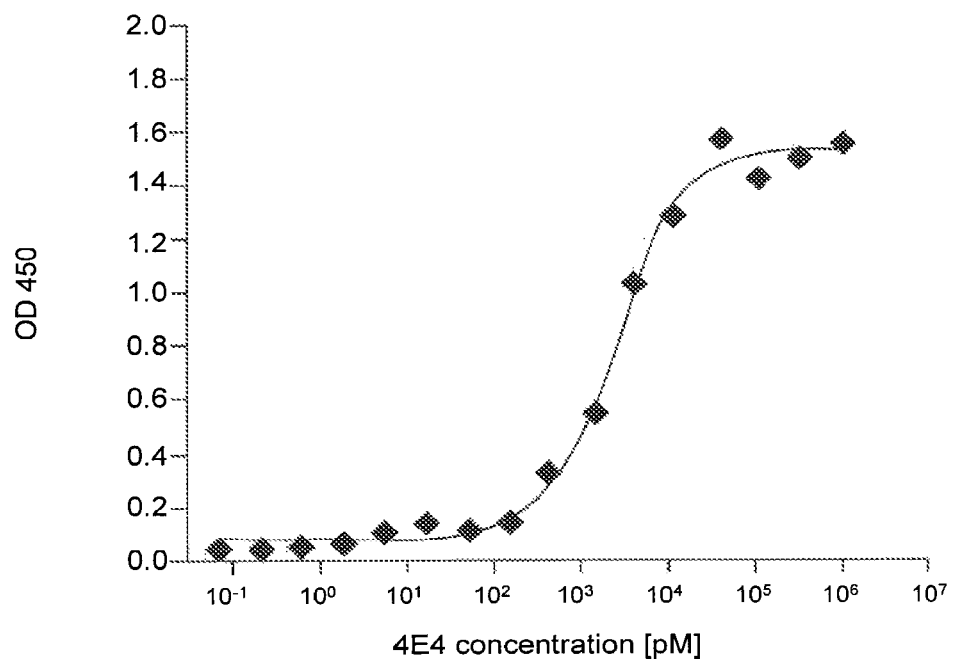
FIG. 2: ELISA plates were coated with recombinant human tau (isoform hTau40) at 1 µg/ml and incubated with the indicated concentrations of NI-105.4E4 antibody. Recombinant human derived antibody NI-105.4E4 binds to recombinant tau with high affinity at 2 nM $EC_{50}$.

Neurodegenerative tauopathies are a diverse group of neurodegenerative disorders that share a common pathologic lesion consisting of intracellular aggregates of abnormal filaments that are mainly composed of pathologically hyperphosphorylated tau in neurons and/or glial cells. Clinical features of the tauopathies are heterogeneous and characterized by dementia and/or motor syndromes. The progressive accumulation of filamentous tau inclusions may cause neuronal and glial degeneration in combination with other deposits as, e.g., beta-amyloid in Alzheimer's disease or as a sole pathenogenic entity as illustrated by mutations in the tau gene that are associated with familial forms of frontotemporal dementia and parkinsonism linked to chromosome 17 (FTDP-17). Because of the heterogeneity of their clinical manifestations a potentially non-exhaustive list of tauopathic diseases may be provided including Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke; see for a review, e.g., Lee et al., Annu. Rev. Neurosci. 24 (2001), 1121-1159 in which Table 1 catalogs the unique members of tauopathies or Sergeant et al., Bioch. Biophy. Acta 1739 (2005), 179-97, with a list in FIG. 2 therein.

In this specification, the terms "tau", is used interchangeable to specifically refer to the native monomer form of tau. The term "tau" is also used to generally identify other conformers of tau, for example, oligomers or aggregates of tau. The term "tau" is also used to refer collectively to all types and forms of tau. Due to alternative splicing 6 tau isoforms are present in the human brain. The protein sequences for these isoforms are:

```
Isoform Fetal-tau of 352aa
                                           (SEQ ID NO: 1)
MAEPRQEFEVMEDHAGTYGLGDRKDQGGYTMHQDQEGDTDAGLKAEEAGI

GDTPSLEDEAAGHVTQARMVSKSKDGTGSDDKKAKGADGKTKIATPRGAA

PPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKS
```

KIGSTENLKHQPGGGKVQIVYKPVDLSKVTSKCGSLGNIHHKPGGGQVEV

KSEKLDFKDRVQSKIGSLDNITHVPGGGNKKIETHKLTFRENAKAKTDHG

AEIVYKSPVVSGDTSPRHLSNVSSTGSIDMVDSPQLATLADEVSASLAKQ

GL

Isoform Tau-B of 381aa (SEQ ID NO: 2)
MAEPRQEFEVMEDHAGTYGLGDRKDQGGYTMHQDQEGDTDAGLKESPLQT

PTEDGSEEPGSETSDAKSTPTAEAEEAGIGDTPSLEDEAAGHVTQARMVS

KSKDGTGSDDKKAKGADGKTKIATPRGAAPPGQKGQANATRIPAKTPPAP

KTPPSSGEPPKSGDRSGYSSPGSPGTPGSRSRTPSLPTPPTREPKKVAVV

RTPPKSPSSAKSRLQTAPVPMPDLKNVKSKIGSTENLKHQPGGGKVQIVY

KPVDLSKVTSKCGSLGNIHHKPGGGQVEVKSEKLDFKDRVQSKIGSLDNI

THVPGGGNKKIETHKLTFRENAKAKTDHGAEIVYKSPVVSGDTSPRHLSN

VSSTGSIDMVDSPQLATLADEVSASLAKQGL

Isoform Tau-C of 410aa (SEQ ID NO: 3)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIVYKPVDLSKVTSKCGSLGNIHHK

PGGGQVEVKSEKLDFKDRVQSKIGSLDNITHVPGGGNKKIETHKLTFREN

AKAKTDHGAEIVYKSPVVSGDTSPRHLSNVSSTGSIDMVDSPQLATLADE

VSASLAKQGL

Isoform Tau-D of 383aa (SEQ ID NO: 4)
MAEPRQEFEVMEDHAGTYGLGDRKDQGGYTMHQDQEGDTDAGLKAEEAGI

GDTPSLEDEAAGHVTQARMVSKSKDGTGSDDKKAKGADGKTKIATPRGAA

PPGQKGQANATRIPAKTPPAPKTPPSSGEPPKSGDRSGYSSPGSPGTPGS

RSRTPSLPTPPTREPKKVAVVRTPPKSPSSAKSRLQTAPVPMPDLKNVKS

KIGSTENLKHQPGGGKVQIINKKLDLSNVQSKCGSKDNIKHVPGGGSVQI

VYKPVDLSKVTSKCGSLGNIHHKPGGGQVEVKSEKLDFKDRVQSKIGSLD

NITHVPGGGNKKIETHKLTFRENAKAKTDHGAEIVYKSPVVSGDTSPRHL

SNVSSTGSIDMVDSPQLATLADEVSASLAKQGL

Isoform Tau-E of 412aa (SEQ ID NO: 5)
MAEPRQEFEVMEDHAGTYGLGDRKDQGGYTMHQDQEGDTDAGLKESPLQT

PTEDGSEEPGSETSDAKSTPTAEAEEAGIGDTPSLEDEAAGHVTQARMVS

KSKDGTGSDDKKAKGADGKTKIATPRGAAPPGQKGQANATRIPAKTPPAP

KTPPSSGEPPKSGDRSGYSSPGSPGTPGSRSRTPSLPTPPTREPKKVAVV

RTPPKSPSSAKSRLQTAPVPMPDLKNVKSKIGSTENLKHQPGGGKVQIIN

KKLDLSNVQSKCGSKDNIKHVPGGGSVQIVYKPVDLSKVTSKCGSLGNIH

HKPGGGQVEVKSEKLDFKDRVQSKIGSLDNITHVPGGGNKKIETHKLTFR

ENAKAKTDHGAEIVYKSPVVSGDTSPRHLSNVSSTGSIDMVDSPQLATLA

DEVSASLAKQGL

Isoform Tau-F of 441aa (SEQ ID NO: 6)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIINKKLDLSNVQSKCGSKDNIKHV

PGGGSVQIVYKPVDLSKVTSKCGSLGNIHHKPGGGQVEVKSEKLDFKDRV

QSKIGSLDNITHVPGGGNKKIETHKLTFRENAKAKTDHGAEIVYKSPVVS

GDTSPRHLSNVSSTGSIDMVDSPQLATLADEVSASLAKQGL

The "wild type" tau amino acid sequence is represented by isoform Tau-F of 441aa (SEQ ID NO:6) further also referenced to as "hTau40", "TauF", "Tau-4" or "full-length tau". The amino acid sequence of tau can be retrieved from the literature and pertinent databases; see Goedert et al., Proc. Natl. Acad. Sci. USA 85 (1988), 4051-4055, Goedert et al., EMBO J. 8(1989), 393-399, Goedert et al., EMBO J. 9 (1990), 4225-4230 and GenBank UniProtKB/swissprot: locus TAU_HUMAN, accession numbers P10636-2 (Fetal-tau) and P10636-4 to -8 (Isoforms B to F).

Another striking feature of tau protein is phosphorylation, which occurs at about 30 of 79 potential serine (Ser) and threonine (Thr) phosphorylation sites. Tau is highly phosphorylated during the brain development. The degree of phosphorylation declines in adulthood. Some of the phosphorylation sites are located within the microtubule binding domains of tau, and it has been shown that an increase of tau phosphorylation negatively regulates the binding of microtubules. For example, Ser262 and Ser396, which lie within or adjacent to microtubule binding motifs, are hyperphosphorylated in the tau proteins of the abnormal paired helical filaments (PHFs)), a major component of the neurofibrillary tangles (NFTs) in the brain of AD patients. PHFs are filamentous aggregates of tau proteins which are abnormally hyperphosphorylated and can be stained with specific anti-tau antibodies and detected by light microscopy. The same holds true for so called straight tau filaments. PHFs form twisted ribbons consisting of two filaments twisted around one another with a periodicity of about 80 nm. These pathological features are commonly referred to as "tau-pathology", "tauopathology" or "tau-related pathology". For a more detailed description of neuropathological features of tauopathies refer to Lee et al., Annu. Rev. Neurosci. 24 (2001), 1121-1159 and Götz, Brain. Res. Rev. 35 (2001), 266-286, the disclosure content of which is incorporated herein by reference. Physiological tau protein stabilizes microtubules in neurons. Pathological phosphorylation leads to abnormal tau localization and aggregation, which causes destabilization of microtubules and impaired cellular transport. Aggregated tau is neurotoxic in vitro (Khlistunova et al., J. Biol. Chem. 281 (2006), 1205-1214). The exact neurotoxic species remains unclear, however, as do the mechanism(s) by which they lead to neuronal death. Aggregates of tau can be observed as the main component of neurofibrillary tangles (NFT) in many tauopathies, such as Alzheimer's disease (AD), Frontotemporal dementias, supranuclear palsy, Pick's disease, Argyrophilic grain disease (AGD), corticobasal degeneration, FTDP-17, Parkinson's disease, Dementia pugilistica (Reviewed in Gendron and Petrucelli, Mol. Neurodegener. 4:13 (2009)). Besides these observations, evidence emerges that tau-mediated neuronal death can occur even in the absence of tangle formation. Soluble phospho-tau species are present in CSF (Aluise et al., Biochim Biophys. Acta. 1782 (2008), 549-558). Tau aggregates can transmit a misfolded state from the outside to the inside of a cell and transfer between co-cultured cells (Frost et al., J. Biol. Chem. 284 (2009), 12845-12852).

In addition to the involvement in neurodegenerative tauopathies, observed alterations in tau phosphorylation during and after ischemia/reperfusion suggest tau playing a crucial role in neuronal damage and clinical pathophysiology of neurovascular disorders such as ischemic stroke (Zheng et al., J. Cell. Biochem. 109 (2010), 26-29).

The human anti-tau antibodies disclosed herein specifically bind tau and epitopes thereof and to various conformations of tau and epitopes thereof. For example, disclosed herein are antibodies that specifically bind tau, tau in its full-length, pathologically modified tau isoforms and tau aggregates. As used herein, reference to an antibody that "specifically binds", "selectively binds", or "preferentially binds" tau refers to an antibody that does not bind other unrelated proteins. In one example, a tau antibody disclosed herein can bind tau or an epitope thereof and show no binding above about 1.5 times background for other proteins. An antibody that "specifically binds" or "selectively binds" a tau conformer refers to an antibody that does not bind all conformations of tau, i.e., does not bind at least one other tau conformer. For example, disclosed herein are antibodies that can preferentially bind to aggregated forms of tau in AD tissue. Since the human anti-tau antibodies of the present invention have been isolated from a pool of healthy human subjects exhibiting an tau-specific immune response the tau antibodies of the present invention may also be called "human auto-antibodies" in order to emphasize that those antibodies were indeed expressed by the subjects and have not been isolated from, for example a human immunoglobulin expressing phage library, which hitherto represented one common method for trying to provide human-like antibodies.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs or variants of the foregoing polypeptides, and any combination thereof. The terms "fragment," "variant," "derivative" and "analog" when referring to antibodies or antibody polypeptides of the present invention include any polypeptides which retain at least some of the antigen-binding properties of the corresponding native binding molecule, antibody, or polypeptide. Fragments of polypeptides of the present invention include proteolytic fragments, as well as deletion fragments, in addition to specific antibody fragments discussed elsewhere herein. Variants of antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of tau specific binding molecules, e.g., antibodies and antibody polypeptides of the present invention, are polypeptides which have been altered so as to exhibit additional features not found on the native polypeptide. Examples include fusion proteins. Variant polypeptides may also be referred to herein as "polypeptide analogs". As used herein a "derivative" of a binding molecule or fragment thereof, an antibody, or an antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding an antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

Unless stated otherwise, the terms "disorder" and "disease" are used interchangeably herein.

A "binding molecule" as used in the context of the present invention relates primarily to antibodies, and fragments thereof, but may also refer to other non-antibody molecules that bind to tau including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent a specific embodiment of binding molecules for the development of therapeutic and diagnostic agents.

The terms "antibody" and "immunoglobulin" are used interchangeably herein. An antibody or immunoglobulin is a tau-binding molecule which comprises at least the variable domain of a heavy chain, and normally comprises at least the variable domains of a heavy chain and a light chain. Basic immunoglobulin structures in vertebrate systems are relatively well understood; see, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the $V_H$ and $V_L$ chains. Any antibody or immunoglobulin fragment which contains sufficient structure to specifically bind to tau is denoted herein interchangeably as a "binding fragment" or an "immunospecific fragment."

In naturally occurring antibodies, an antibody comprises six hypervariable regions, sometimes called "complementarity determining regions" or "CDRs" present in each antigen-binding domain, which are short, non-contiguous sequences of amino acids that are specifically positioned to form the antigen-binding domain as the antibody assumes its three dimensional configuration in an aqueous environment. The "CDRs" are flanked by four relatively conserved "framework" regions or "FRs" which show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined; see, "Sequences of Proteins of Immunological Interest," Kabat, E., et al., U.S. Department of Health and Human Services, (1983); and Chothia and Lesk, J. Mol. Biol., 196 (1987), 901-917, which are incorporated herein by reference in their entireties.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia and Lesk, J. Mol. Biol., 196 (1987), 901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular hypervariable region or CDR of the human IgG subtype of antibody given the variable region amino acid sequence of the antibody.

TABLE 1

| | CDR Definitions[1] | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present invention are according to the Kabat numbering system, which however is theoretical and may not equally apply every antibody of the present invention. For example, depending on the position of the first CDR the following CDRs might be shifted in either direction.

Antibodies or antigen-binding fragments, immunospecific fragments, variants, or derivatives thereof of the invention include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019 Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

In one embodiment, the antibody of the present invention is not IgM or a derivative thereof with a pentavalent structure. Particular, in specific applications of the present invention, especially therapeutic use, IgMs are less useful than IgG and other bivalent antibodies or corresponding binding molecules since IgMs due to their pentavalent structure and lack of affinity maturation often show unspecific cross-reactivities and very low affinity.

In a particular embodiment, the antibody of the present invention is not a polyclonal antibody, i.e. it substantially consists of one particular antibody species rather than being a mixture obtained from a plasma immunoglobulin sample.

Antibody fragments, including single-chain antibodies, may comprise the variable region(s) alone or in combination with the entirety or a portion of the following: hinge region, CH1, CH2, and CH3 domains. Also included in the invention are tau-binding fragments also comprising any combination of variable region(s) with a hinge region, CH1, CH2, and CH3 domains. Antibodies or immunospecific fragments thereof of the present invention may be from any animal origin including birds and mammals. In one embodiment, the antibodies are human, murine, donkey, rabbit, goat, guinea pig, camel, llama, horse, or chicken antibodies. In another embodiment, the variable region may be condricthoid in origin (e.g., from sharks).

In one aspect, the antibody of the present invention is a human monoclonal antibody isolated from a human. Optionally, the framework region of the human antibody is aligned and adopted in accordance with the pertinent human germ line variable region sequences in the database; see, e.g., Vbase (http://vbase.mrc-cpe.cam.ac.uk/) hosted by the MRC Centre for Protein Engineering (Cambridge, UK). For example, amino acids considered to potentially deviate from the true germ line sequence could be due to the PCR primer sequences incorporated during the cloning process. Compared to artificially generated human-like antibodies such as single chain antibody fragments (scFvs) from a phage displayed antibody library or xenogeneic mice the human monoclonal antibody of the present invention is characterized by (i) being obtained using the human immune response rather than that of animal surrogates, i.e. the antibody has been generated in response to natural tau in its relevant conformation in the human body, (ii) having protected the individual or is at least significant for the presence of tau, and (iii) since the antibody is of human origin the risks of cross-reactivity against self-antigens is minimized Thus, in accordance with the present invention the terms "human monoclonal antibody", "human monoclonal autoantibody", "human antibody" and the like are used to denote a tau binding molecule which is of human origin, i.e. which has been isolated from a human cell such as a B cell or hybridoma thereof or the cDNA of which has been directly cloned from mRNA of a human cell, for example a human memory B cell. A human antibody is still "human" even if amino acid substitutions are made in the antibody, e.g., to improve binding characteristics.

Antibodies derived from human immunoglobulin libraries or from animals transgenic for one or more human immunoglobulins and that do not express endogenous immunoglobulins, as described infra and, for example in, U.S. Pat. No. 5,939,598 by Kucherlapati et al., are denoted human-like antibodies in order distinguish them from truly human antibodies of the present invention.

For example, the paring of heavy and light chains of human-like antibodies such as synthetic and semi-synthetic antibodies typically isolated from phage display do not necessarily reflect the original paring as it occurred in the original human B cell. Accordingly Fab and scFv fragments obtained from recombinant expression libraries as commonly used in the prior art can be considered as being artificial with all possible associated effects on immunogenicity and stability.

In contrast, the present invention provides isolated affinity-matured antibodies from selected human subjects, which are characterized by their therapeutic utility and their tolerance in man.

As used herein, the term "murinized antibody" or "murinized immunoglobulin" refers to an antibody comprising one or more CDRs from a human antibody of the present invention; and a human framework region that contains amino acid substitutions and/or deletions and/or insertions that are based on a mouse antibody sequence. The human immunoglobulin providing the CDRs is called the "parent" or "acceptor" and the mouse antibody providing the framework changes is called the "donor". Constant regions need not be present, but if they are, they are usually substantially identical to mouse antibody constant regions, i.e. at least about 85-90%, about 95%, about 96%, about 97%, about 98%, about 99% or more identical. Hence, in some embodiments, a full-length murinized human heavy or light chain immunoglobulin contains a mouse constant region, human CDRs, and a substantially human framework that has a number of "murinizing" amino acid substitutions. Typically, a "murinized antibody" is an antibody comprising a murinized variable light chain and/or a murinized variable heavy chain. For example, a murinized antibody would not encompass a typical chimeric antibody, e.g., because the entire variable region of a chimeric antibody is non-mouse. A modified antibody that has been "murinized" by the process of "murinization" binds to the same antigen as the parent antibody that provides the CDRs and is usually less immunogenic in mice, as compared to the parent antibody.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody or diabody.

In another embodiment, the antibodies, or antigen-binding fragments, variants, or derivatives thereof disclosed herein are composed of a single polypeptide chain such as scFvs and are to be expressed intracellularly (intrabodies) for potential in vivo therapeutic and diagnostic applications.

The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. In one embodiment, the light chain portion comprises at least one of a $V_L$ or CL domain.

The minimum size of a peptide or polypeptide epitope for an antibody is thought to be about four to five amino acids. Peptide or polypeptide epitopes may contain at least seven, at least nine or between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, a peptide or polypeptide epitope recognized by antibodies of the present invention contains a sequence of at least 4, at least 5, at least 6, at least 7, at least 8, at least 9, at least 10, at least 15, at least 20, at least 25, or between about 5 to about 30, about 10 to about 30 or about 15 to about 30 contiguous or non-contiguous amino acids of tau.

By "specifically binding", or "specifically recognizing", used interchangeably herein, it is generally meant that a binding molecule, e.g., an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. A skilled artisan understands that an antibody may specifically bind to, or specifically recognize an isolated polypeptide comprising, or consisting of, amino acid residues corresponding to a linear portion of a non-contiguous epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D".

Where present, the term "immunological binding characteristics," or other binding characteristics of an antibody with an antigen, in all of its grammatical forms, refers to the specificity, affinity, cross-reactivity, and other binding characteristics of an antibody.

By "preferentially binding", it is meant that the binding molecule, e.g., antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, a binding molecule, e.g., an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, a binding molecule, e.g., an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

A binding molecule, e.g., an antibody or antigen-binding fragment, variant, or derivative disclosed herein may be said to bind a tau or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. In one embodiment, an antibody of the invention may be said to bind tau or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$.

A binding molecule, e.g., an antibody or antigen-binding fragment, variant, or derivative disclosed herein may be said to bind tau or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. In one embodiment, an antibody of the invention may be said to bind tau or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

A binding molecule, e.g., an antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%. A skilled artisan understands that the binding of an antibody to its epitope may also be competitively inhibited by a binding molecule that is not an antibody. For example, the specific binding of an antibody described herein to tau, e.g., hTau40, may be competitively inhibited by microtubules.

As used herein, the term "affinity" refers to a measure of the strength of the binding of an individual epitope with the CDR of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" In *Fundamental Immunology*, Paul, W. E., Ed., Raven Press New York, N.Y. (1984), Kuby, Janis Immunology, W. H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., $K_D$, IC$_{50}$, are preferably made with standardized solutions of antibody and antigen, and a standardized buffer.

Binding molecules, e.g., antibodies or antigen-binding fragments, variants or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Binding molecules, e.g., antibodies or antigen-binding fragments, variants or derivatives thereof of the invention may also be described or specified in terms of their binding affinity to tau. In one embodiment, binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "CH1 domain" includes the first (most amino terminal) constant region domain of an immunoglobulin heavy chain. The CH1 domain is adjacent to the $V_H$ domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently.

Hinge regions can be subdivided into three distinct domains: upper, middle, and lower hinge domains; see Roux et al., J. Immunol. 161 (1998), 4083.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the terms "linked", "fused" or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product, and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the term "sample" refers to any biological material obtained from a subject or patient. In one aspect, a sample can comprise blood, cerebrospinal fluid ("CSF"), or urine. In other aspects, a sample can comprise whole blood, plasma, B cells enriched from blood samples, and cultured cells (e.g., B cells from a subject). A sample can also include a biopsy or tissue sample including neural tissue. In still other aspects, a sample can comprise whole cells and/or a lysate of the cells. Blood samples can be collected by methods known in the art. In one aspect, the pellet can be resuspended by vortexing at 4° C. in 200 µl buffer (20 mM Tris, pH. 7.5, 0.5% Nonidet, 1 mM EDTA, 1 mM PMSF, 0.1M NaCl, IX Sigma Protease Inhibitor, and IX Sigma Phosphatase Inhibitors 1 and 2). The suspension can be kept on ice for 20 minutes with intermittent vortexing. After spinning at 15,000×g for 5 minutes at about 4° C., aliquots of supernatant can be stored at about −70° C.

As used herein, the terms "treat" or "treatment" refer to both therapeutic treatment and prophylactic or preventative measures, wherein the object is to prevent or slow down (lessen) an undesired physiological change or disorder, such as the development of Parkinsonism. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

By "subject" or "individual" or "animal" or "patient" or "mammal," is meant any subject, particularly a mammalian subject, e.g., a human patient, for whom diagnosis, prognosis, prevention, or therapy is desired.

II. Antibodies

The present invention generally relates to human anti-tau antibodies and antigen-binding fragments thereof. In one embodiment, an antibody of the present invention demonstrates the immunological binding characteristics and/or biological properties as outlined for the antibodies illustrated in the Examples. In accordance with the present invention human monoclonal antibodies specific for tau were cloned from a pool of healthy human subjects.

In the course of the experiments performed in accordance with the present invention initial attempts failed to clone tau specific antibodies but almost always resulted in false-positive clones. In order to circumvent this problem, antibodies in conditioned media of human memory B cell cultures were screened in parallel for binding to recombinant tau protein, PHFTau extracted from AD brain, healthy control brain extracts and bovine serum albumin (BSA). Only B-cell cultures that were positive for recombinant tau and/or PHFTau but not control brain extract or BSA were subjected to antibody cloning.

Initial attempts to isolating to specific antibodies were focused at pools of healthy human subjects with high plasma binding activity to tau, suggestive of elevated levels of circulating tau antibodies plasma. Unexpectedly, these attempts failed to produce tau specific human memory B cells and the antibodies described in the current invention were isolated from pools of healthy human subjects that were not preselected for high tau plasma reactivity or had low plasma reactivity to tau.

Due to this measure, several antibodies could be isolated. Selected antibodies were further analyzed for class and light chain subclass determination. Selected relevant antibody messages from memory B cell cultures are then transcribed by RT-PCR, cloned and combined into expression vectors for recombinant production; see the appended Examples. Recombinant expression of the human antibodies in HEK293 or CHO cells and the subsequent characterization of their binding specificities towards full-length tau (FIG. 2, FIG. 7 and FIG. 12), pathologically modified forms thereof on Western Blot (FIG. 3 and FIG. 8) and their distinctive binding to pathologically aggregated tau confirmed that for the first time human antibodies have been cloned that are highly specific for tau and recognize distinctive the pathologically modified forms of tau protein.

Thus, the present invention generally relates to an isolated naturally occurring human monoclonal anti-tau antibody and binding fragments, derivatives and variants thereof. In one embodiment of the invention, the antibody is capable of specifically binding full-length recombinant tau and/or the pathologically aggregated and/or phosphorylated form (PH-FTau) isolated from AD brain under denaturing conditions on Western Blot; see FIG. 3 and FIG. 8.

Figure 11:
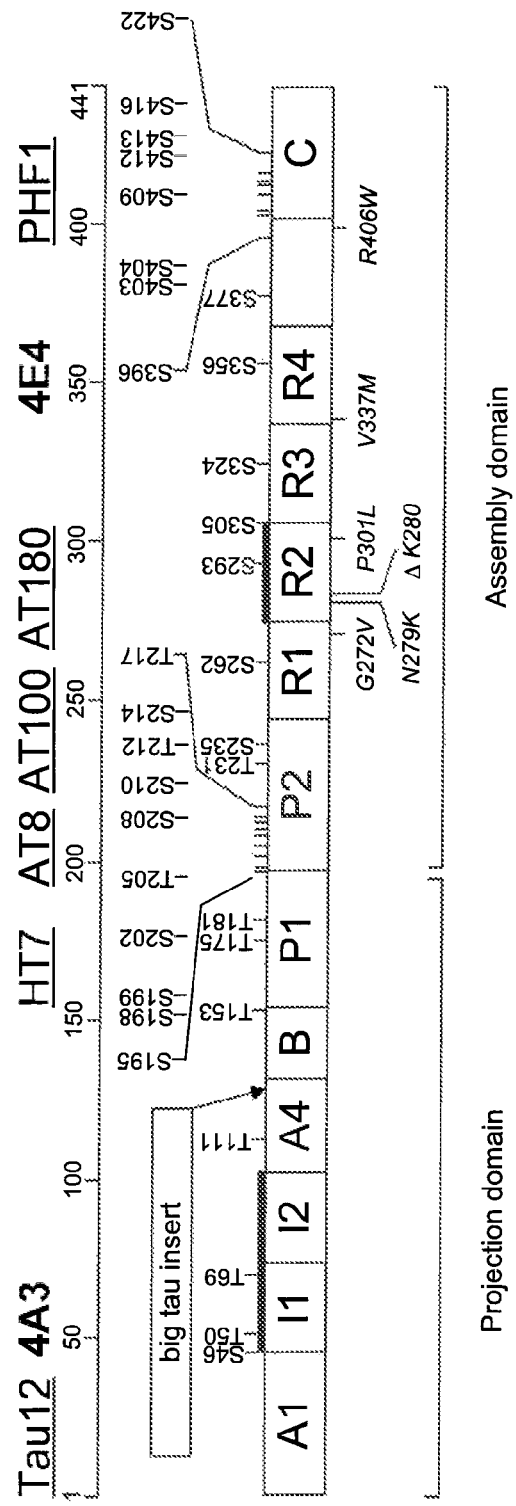
FIG. 11: The NI-105.4E4 and NI-105.4A3 epitopes and epitopes of commonly used commercially available mouse monoclonal tau antibodies are shown. Human antibody NI-105.4E4 targets a unique epitope that comprises two linear polypeptides, one of which is located in the microtubule binding domain (R4) of tau which is masked in physiological microtubule-associated tau. Tau-12 (Covance, California, U.S.A.), HT7, AT8, AT180 (Thermo Scientific, U.S.A.); PHF1 (Lewis et al., Science 293 (2001), 1487-1491).

In one embodiment, the present invention is directed to an anti-tau antibody, or antigen-binding fragment, variant or derivatives thereof, where the antibody specifically binds to the same epitope of tau as a reference antibody selected from the group consisting of NI-105-4E4, NI-105-24B2 or NI-105.4A3. In addition, preliminary results of direct ELISA assays performed with the exemplary antibody NI-105-4E4 revealed that NI-105-4E4 specifically recognizes the C-terminus of tau. Additional assays performed suggest that NI-105.4E4 recognizes a discontinuous epitope comprising two linear sequences: a first linear sequence within the R4 microtubule binding domain and a second linear sequence within the region between the R4 and C domains as depicted in FIG. 11. In one embodiment, a linear polypeptide comprised by a non-continuous epitope, or an epitope recognized by an antibody provided by this invention is located in the microtubule binding domain of tau, which is masked in physiological microtubule-associated tau. Epitope mapping identified a first sequence within the microtubule binding domain of human tau including aa337-343 VEVKSEK (SEQ ID NO:7) as a unique linear polypeptide comprised by the epitope recognized by antibody NI-105.4E4 of this invention. Additional experiments and comparison with a commercially available AT180 mouse monoclonal tau antibody confirmed that NI-105-4E4 specifically recognizes the unique epitope of SEQ ID NO:7. Most advantageously, the SEQ ID NO:7 epitope recognized by the antibody NI-105.4E4 of this invention is 100% conserved in all 6 tau isoforms present in the human brain of the amino acid sequences represented by SEQ ID NO:1 to 6 and in other species, such as mouse and rat as well providing an additional research tool in respective animal models with the antibodies of the present invention. Further experimentation showed that residues 3 and 6 of the SEQ ID NO: 7 polypeptide, corresponding to residues V339 and E342 of SEQ ID NO: 6, contribute to the binding of NI-105.4E4. Epitope mapping further identified a second sequence (SEQ ID NO:41) within the microtubule binding domain of human tau including aa387-397 of SEQ ID NO:6 as a unique linear polypeptide comprised by the epitope recognized by antibody NI-105.4E4 of this invention. Residues 1, 5 and 9 of SEQ ID NO: 41, corresponding to residues D387, E391 and K395 of SEQ ID NO: 6, contribute to the binding of NI-105.4E4.

In one embodiment, an antibody described herein specifically binds to tau at an epitope comprising the amino acid residues of SEQ ID NO: 7. In another embodiment, an antibody described herein specifically binds to tau at an epitope comprising the amino acid residues of SEQ ID: 41. In a specific embodiment, an antibody described herein specifically binds to tau at an epitope comprising the amino acid residues of SEQ ID NO:7 and SEQ ID NO:41. In a further embodiment, an antibody described herein specifically binds to tau at an epitope comprising one or more amino acid residues selected from the group consisting of residues V339, E342, D387, E391 and K395 of SEQ ID NO:6. The epitope may comprise any one, any two, any three, any four or all five residues from the group consisting of residues V339, E342, D387, E391 and K395 of SEQ ID NO:6. In a specific embodiment, tau is hTau40.

In one embodiment, an antibody described herein binds to tau at an epitope comprising the microtubule binding domain of tau. In a specific embodiment, an antibody described herein binds to tau at an epitope comprising amino acid residues from the R4 region of tau as depicted in FIG. 11. In one embodiment, an antibody described herein competes with microtubules for specific binding to tau. In another embodiment, an antibody described herein has reduced binding affinity to microtubule associated tau compared to the antibodies binding affinity to tau no associated with microtubules. In a further embodiment, an antibody described herein does not bind, or substantially does not bind to tau associated with microtubules. In specific embodiments, the tau protein may be native tau protein or recombinant tau protein. In a specific embodiment, tau is hTau40.

Epitope mapping further identified a sequence (SEQ ID NO:42) of human tau including aa35-49 of SEQ ID NO:6 as a unique linear epitope recognized by antibody NI-105.4A3 of this invention. Residues 6, 7 and 10 of SEQ ID NO: 42, corresponding to residues D40, A41 and K44 of SEQ ID NO: 6, contribute to the binding of NI-105.4A3. In one embodiment, an antibody described herein specifically binds to tau at an epitope comprising the amino acid residues of SEQ ID NO: 42. In a further embodiment, an antibody described herein specifically binds to tau at an epitope comprising one or more amino acid residues selected from the group consisting of residues D40, A41 and K44 of SEQ ID NO:6. The epitope may comprise any one, any two, or all any three residues from the group consisting of residues D40, A41 and K44 of SEQ ID NO:6. In a specific embodiment, tau is hTau40.

Figure 6:
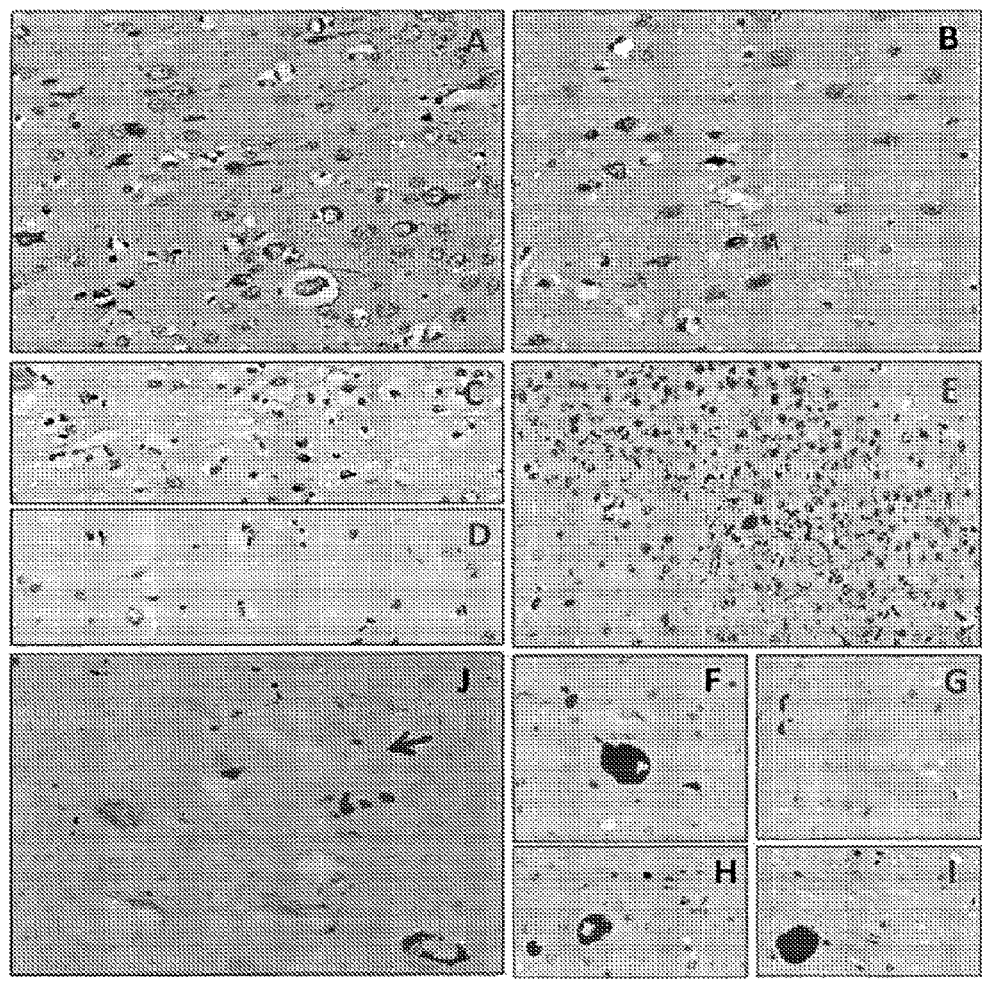
FIG. 6: NI-105.4E4 binds to neurofibrillary tangles (NFT), dystrophic neurites and neuropil threads in AD brain and human TauP301L expressing mice. NI105-4E4 staining identifies NFTs and neuropil threads in AD brain (A), with no significant binding to tau in the brain of healthy control subject (B). In TauP301L transgenic mouse (E-I) NI-105.4E4 binds strongly to the pathological tau resembling NFT (E, F and H), neuropil threads (E and G) and dystrophic neurites (E and H). In addition, NI-105.4E4 also identifies tau aggregates at pre-tangle stage (I). NI-105.4E4 binds to NFT, dystrophic neurites and neuropil threads in transgenic mouse expressing human APP with the Swedish and the Arctic mutation and TauP301L; the arrow marks a beta-amyloid plaque, surrounded by dystrophic neurites recognized by NI-105.4E4 (J). Secondary antibody only does not give signal both in human AD (C) and healthy control (D).

Further, without intending to be bound by initial experimental observations as demonstrated in the Examples and shown in FIG. 6, the human monoclonal NI-105-4E4 anti-tau antibody of the present invention is characterized in specifically binding pathologically aggregated tau and not substantially recognizing tau in the physiological form in brain tissue. In one embodiment, a human anti-tau antibody of the present invention may specifically bind pathologically aggregated tau and not substantially bind tau in the physiological form in brain tissue. In addition, a human anti-tau antibody of the present invention may be further characterized by its ability to recognize tau at the pre-tangle stage, in neurofibrillary tangles (NFT), neutropil threads and/or dystrophic neurites in the brain. Hence, the present invention provides a set of human tau antibodies with binding specificities, which are thus particularly useful for diagnostic and therapeutic purposes.

In one embodiment, the antibody of the present invention exhibits the binding properties of the exemplary NI-105-4E4 antibody as described in the Examples. In addition, or alternatively, an anti-tau antibody of the present invention preferentially recognizes pathologically aggregated tau rather than physiological forms, in particular when analyzed according to Example 4. In addition, or alternatively, an anti-tau antibody of the present invention binds to disease causing mutants of human tau, in particular those described in Example 4. In this context, the binding specificities may be in the range as shown for the exemplary NI-105.4E4, NI-1054A3 and NI-105.24B2 antibodies in FIG. 2, FIG. 12 and FIG. 7, respectively, i.e. having half maximal effective concentrations (EC50) of about 100 pM to 100 nM, or an EC50 of about 100 pM to 10 nM for wild-type tau.

Hence, an anti-tau antibody of the present invention binds preferentially to pathological modified forms of tau in brain, e.g. pathological aggregates of tau as exemplified by immunohistochemical staining described in Example 4. In another embodiment an anti-tau antibody of the present invention preferentially binds to both recombinant tau and pathologically modified forms of tau as exemplified in Example 2 by Western Blot.

The present invention is also drawn to an antibody, or antigen-binding fragment, variant or derivatives thereof, where the antibody comprises an antigen-binding domain identical to that of an antibody selected from the group consisting of NI-105-4E4, NI-105-24B2 and NI-105.4A3.

The present invention further exemplifies several such binding molecules, e.g. antibodies and binding fragments thereof, which may be characterized by comprising in their variable region, e.g. binding domain at least one complementarity determining region (CDR) of the VH and/or VL variable region comprising any one of the amino acid sequences depicted in FIG. 1. The corresponding nucleotide sequences encoding the above-identified variable regions are set forth in Table 2 below. An exemplary set of CDRs of the above amino acid sequences of the VH and/or VL region as depicted in FIG. 1. However, as discussed in the following the person skilled in the art is well aware of the fact that in addition or alternatively CDRs may be used, which differ in their amino acid sequence from those set forth in FIG. 1 by one, two, three or even more amino acids in case of CDR2 and CDR3.

In one embodiment, an antibody of the present invention comprises at least one CDR comprising, or consisting of an amino acid sequence selected from the group consisting of SEQ ID NO: 23-25, 26-28, 29-31, 32-34, 35-37 and 38-40. In one embodiment, an antibody of the present invention comprises one, two, three, four, five or six CDRs comprising, or consisting of an amino acid sequence selected from the group consisting of SEQ ID NO: 23-25, 26-28, 29-31, 32-34, 35-37 and 38-40. The antibody may comprise a heavy chain variable region comprising a VH CDR1 of SEQ ID NO: 23, 29 or 35; a VH CDR2 of SEQ ID NO: 24, 30 or 36; or a VH CDR3 of SEQ ID NO: 25, 31 or 37. The antibody may comprise a light chain variable region comprising a VL CDR1 of SEQ ID NO: 26, 32 or 38; a VL CDR2 of SEQ ID NO: 27, 33 or 39; or a VL CDR3 of SEQ ID NO: 28, 34 or 40. The antibody may comprise a heavy chain variable region comprising a VH CDR1 of SEQ ID NO: 23, 29 or 35; a VH CDR2 of SEQ ID NO: 24, 30 or 36; or a VH CDR3 of SEQ ID NO: 25, 31 or 37, and may further comprise a light chain variable region comprising a VL CDR1 of SEQ ID NO: 26, 32 or 38; a VL CDR2 of SEQ ID NO: 27, 33 or 39; or a VL CDR3 of SEQ ID NO: 28, 34 or 40.

In one embodiment, an antibody of the present invention may comprise a heavy chain variable region comprising a VH CDR1 of SEQ ID NO: 23, 29 or 35; a VH CDR2 of SEQ ID NO: 24, 30 or 36; and a VH CDR3 of SEQ ID NO: 25, 31 or 37. In one embodiment, an antibody of the present invention may comprise a light chain variable region comprising a VL CDR1 of SEQ ID NO: 26, 32 or 38; a VL CDR2 of SEQ ID NO: 27, 33 or 39; and a VL CDR3 of SEQ ID NO: 28, 34 or 40. The antibody may further comprise a heavy chain variable region comprising a VH CDR1 of SEQ ID NO: 23, 29 or 35; a VH CDR2 of SEQ ID NO: 24, 30 or 36; and a VH CDR3 of SEQ ID NO: 25, 31 or 37, and may further comprise a light chain variable region comprising a VL CDR1 of SEQ ID NO: 26, 32 or 38; a VL CDR2 of SEQ ID NO: 27, 33 or 39; and a VL CDR3 of SEQ ID NO: 28, 34 or 40.

In one embodiment, an antibody of the present invention may comprise a heavy chain variable region comprising a VH CDR1 of SEQ ID NO: 23; a VH CDR2 of SEQ ID NO: 24; and a VH CDR3 of SEQ ID NO: 25. In one embodiment, an antibody of the present invention may comprise a heavy chain variable region comprising a VH CDR1 of SEQ ID NO: 29; a VH CDR2 of SEQ ID NO: 30; and a VH CDR3 of SEQ ID NO: 31. In one embodiment, an antibody of the present invention may comprise a heavy chain variable region comprising a VH CDR1 of SEQ ID NO: 35; a VH CDR2 of SEQ ID NO: 36; and a VH CDR3 of SEQ ID NO: 37.

In one embodiment, an antibody of the present invention may comprise a light chain variable region comprising a VL CDR1 of SEQ ID NO: 26; a VL CDR2 of SEQ ID NO: 27; and a VL CDR3 of SEQ ID NO: 28. In one embodiment, an antibody of the present invention may comprise a light chain variable region comprising a VL CDR1 of SEQ ID NO: 32; a VL CDR2 of SEQ ID NO: 33; and a VL CDR3 of SEQ ID NO: 34. In one embodiment, an antibody of the present invention may comprise a light chain variable region comprising a VL CDR1 of SEQ ID NO: 38; a VL CDR2 of SEQ ID NO: 39; and a VL CDR3 of SEQ ID NO: 40.

In one embodiment, an antibody of the present invention may comprise a heavy chain variable region comprising a VH CDR1 of SEQ ID NO: 23; a VH CDR2 of SEQ ID NO: 24; and a VH CDR3 of SEQ ID NO: 25, and may further comprise a light chain variable region comprising a VL CDR1 of SEQ ID NO: 26; a VL CDR2 of SEQ ID NO: 27; and a VL CDR3 of SEQ ID NO: 28.

In one embodiment, an antibody of the present invention may comprise a heavy chain variable region comprising a VH CDR1 of SEQ ID NO: 29; a VH CDR2 of SEQ ID NO: 30; and a VH CDR3 of SEQ ID NO: 31 and may further comprise a light chain variable region comprising a VL CDR1 of SEQ ID NO: 32; a VL CDR2 of SEQ ID NO: 33; and a VL CDR3 of SEQ ID NO: 34.

In one embodiment, an antibody of the present invention may comprise a heavy chain variable region comprising a VH CDR1 of SEQ ID NO: 35; a VH CDR2 of SEQ ID NO: 36; and a VH CDR3 of SEQ ID NO: 37 and may further comprise a light chain variable region comprising a VL CDR1 of SEQ ID NO: 38; a VL CDR2 of SEQ ID NO: 39; and a VL CDR3 of SEQ ID NO: 40.

In one embodiment, the antibody of the present invention is any one of the antibodies comprising an amino acid sequence of the VH and/or VL region as depicted in FIG. 1. In one embodiment, the antibody of the present invention is characterized by the preservation of the cognate pairing of the heavy and light chain as was present in the human B-cell.

In one embodiment, an antibody of the present invention comprises a heavy chain variable region (VH) comprising, or consisting of an amino acid sequence selected from the group consisting of SEQ ID NO: 9, 13, 17 and 93. In one embodiment, an antibody of the present invention comprises a light chain variable region (VL) comprising, or consisting of an amino acid sequence selected from the group consisting of SEQ ID NO: 11, 15 and 19. In one embodiment, an antibody of the present invention comprises a heavy chain variable region (VH) comprising, or consisting of an amino acid sequence selected from the group consisting of SEQ ID NO: 9, 13, 17 and 93, and further comprises a light chain variable region (VL) comprising, or consisting of an amino acid sequence selected from the group consisting of SEQ ID NO: 11, 15 and 19. In a specific embodiment, the antibody comprises a VH of SEQ ID NO: 9 and a VL of SEQ ID NO: 11; or a VH of SEQ ID NO: 93 and a VL of SEQ ID NO: 11; a VH of SEQ ID NO: 13 and a VL of SEQ ID NO: 15; or a VH of SEQ ID NO: 17 and a VL of SEQ ID NO: 19.

Alternatively, the antibody of the present invention is an antibody or antigen-binding fragment, derivative or variant thereof, which competes for binding to tau, such as, for example, hTau40, with at least one of the antibodies having the VH and/or VL region as depicted in FIG. 1. In one embodiment, an antibody of the present invention competes for specific binding to hTau40 with NI-105.4E4, NI-105.24B2 or NI-105.4A3. Those antibodies may be human as well, in particular for therapeutic applications. Alternatively, the antibody is a murine, murinized and chimeric murine-human antibody, which are particularly useful for diagnostic methods and studies in animals.

In one embodiment the antibody of the present invention is provided by cultures of single or oligoclonal B-cells that are cultured and the supernatant of the culture, which contains antibodies produced by said B-cells is screened for presence and affinity of anti-tau antibodies therein. The screening process comprises the steps of a sensitive tissue amyloid plaque immunoreactivity (TAPIR) assay such as described in international application WO2004/095031, the disclosure content of which is incorporated herein by reference; screen on brain sections for binding to PHFTau; screening for binding of a peptide derived from tau of the amino acid sequence represented by SEQ ID NO:6 with phosphate groups on amino acids Ser-202 and Thr-205; on amino acid Thr-231; and/or on amino acids Ser-396 and Ser-404 of said sequence; a screen for binding of recombinant human tau of the amino acid sequence represented by SEQ ID NO:6 and isolating the antibody for which binding is detected or the cell producing said antibody.

As mentioned above, due to its generation upon a human immune response the human monoclonal antibody of the present invention will recognize epitopes which are of particular pathological relevance and which might not be accessible or less immunogenic in case of immunization processes for the generation of, for example, mouse monoclonal antibodies and in vitro screening of phage display libraries, respectively. Accordingly, it is prudent to stipulate that the epitope of the human anti-tau antibody of the present invention is unique and no other antibody which is capable of binding to the epitope recognized by the human monoclonal antibody of the present invention exists; see also FIG. 11 which shows the unique epitope of antibodies NI-105.4E4 and NI-105.4A3. Therefore, the present invention also extends generally to anti-tau antibodies and tau binding molecules which compete with the human monoclonal antibody of the present invention for specific binding to tau. The present invention is more specifically directed to an antibody, or antigen-binding fragment, variant or derivatives thereof, where the antibody specifically binds to the same epitope of tau as a reference antibody selected from the group consisting of NI-105.4E4, NI-105.24B2 and NI-105.4A3.

Competition between antibodies is determined by an assay in which the immunoglobulin under test inhibits specific binding of a reference antibody to a common antigen, such as tau. Numerous types of competitive binding assays are known, for example: solid phase direct or indirect radioimmunoassay (RIA), solid phase direct or indirect enzyme immunoassay (EIA), sandwich competition assay; see Stahli et al., Methods in Enzymology 9 (1983), 242-253; solid phase direct biotin-avidin EIA; see Kirkland et al., J. Immunol. 137 (1986), 3614-3619 and Cheung et al., Virology 176 (1990), 546-552; solid phase direct labeled assay, solid phase direct labeled sandwich assay; see Harlow and Lane, Antibodies, A Laboratory Manual, Cold Spring Harbor Press (1988); solid phase direct label RIA using 1125 label; see Morel et al, Molec. Immunol. 25 (1988), 7-15 and Moldenhauer et al., Scand. J. Immunol. 32 (1990), 77-82. Typically, such an assay involves the use of purified tau or aggregates thereof bound to a solid surface or cells bearing either of these, an unlabelled test immunoglobulin and a labeled reference immunoglobulin, i.e. the human monoclonal antibody of the present invention. Competitive inhibition is measured by determining the amount of label bound to the solid surface or cells in the presence of the test immunoglobulin. Usually the test immunoglobulin is present in excess. In one embodiment, the competitive binding assay is performed under conditions as described for the ELISA assay in the appended Examples. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50% or 75%. Hence, the present invention is further drawn to an antibody, or antigen-binding fragment, variant or derivatives thereof, where the antibody competitively inhibits a reference antibody selected from the group consisting of NI-105.4E4, NI-105.24B2 or NI-105.4A3 from binding to tau.

In another embodiment, the present invention provides an isolated polypeptide comprising, consisting essentially of, or consisting of an immunoglobulin heavy chain variable region (VH), where at least one of VH-CDRs of the heavy chain variable region or at least two of the VH-CDRs of the heavy chain variable region are at least 80%, 85%, 90%, 95%, 96%, 97%, 98% or 99% identical to reference heavy chain VH-CDR1, VH-CDR2 or VH-CDR3 amino acid sequences from the antibodies disclosed herein. Alternatively, the VH-CDR1, VH-CDR2 and VH-CDR3 regions of the VH are at least 80%, 85%, 90%, 95%, 96%, 97%, 98% or 99% identical to reference heavy chain VH-CDR1, VH-CDR2 and VH-CDR3 amino acid sequences from the antibodies disclosed herein. Thus, according to this embodiment a heavy chain variable region of the invention has VH-CDR1, VH-CDR2 and VH-CDR3 polypeptide sequences related to the groups shown in FIG. 1. While FIG. 1 shows VH-CDRs defined by the Kabat system, other CDR definitions, e.g., VH-CDRs defined by the Chothia system, are also included in the present invention, and can be easily identified by a person of ordinary skill in the art using the data presented in FIG. 1. In one embodiment, the amino acid sequence of the reference VH CDR1 is SEQ ID NO: 23, 29, or 35; the amino acid sequence of the reference VH CDR2 is SEQ ID NO: 24, 30 or 36; and the amino acid sequence of the reference VH CDR3 is SEQ ID NO: 25, 31 or 37.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in FIG. 1. In one embodiment, the amino acid sequence of the VH CDR1 is SEQ ID NO: 23, 29, or 35; the amino acid sequence of the VH CDR2 is SEQ ID NO: 24, 30 or 36; and the amino acid sequence of the VH CDR3 is SEQ ID NO: 25, 31 or 37.

In another embodiment, the present invention provides an isolated polypeptide comprising, consisting essentially of, or consisting of an immunoglobulin heavy chain variable region (VH) in which the VH-CDR1, VH-CDR2 and VH-CDR3 regions have polypeptide sequences which are identical to the VH-CDR1, VH-CDR2 and VH-CDR3 groups shown in FIG. 1, except for one, two, three, four, five, six, seven, eight, nine, or ten amino acid substitutions in any one VH-CDR. In certain embodiments the amino acid substitutions are conservative. In one embodiment, the amino acid sequence of the VH CDR1 is SEQ ID NO: 23, 29, or 35; the amino acid sequence of the VH CDR2 is SEQ ID NO: 24, 30 or 36; and the amino acid sequence of the VH CDR3 is SEQ ID NO: 25, 31 or 37.

In another embodiment, the present invention provides an isolated polypeptide comprising, consisting essentially of, or consisting of an immunoglobulin light chain variable region (VL), where at least one of the VL-CDRs of the light chain variable region or at least two of the VL-CDRs of the light chain variable region are at least 80%, 85%, 90%, 95%, 96%, 97%, 98% or 99% identical to reference light chain VL-CDR1, VL-CDR2 or VL-CDR3 amino acid sequences from antibodies disclosed herein. Alternatively, the VL-CDR1, VL-CDR2 and VL-CDR3 regions of the VL are at least 80%, 85%, 90%, 95%, 96%, 97%, 98% or 99% identical to reference light chain VL-CDR1, VL-CDR2 and VL-CDR3 amino acid sequences from antibodies disclosed herein. Thus, according to this embodiment a light chain variable region of the invention has VL-CDR1, VL-CDR2 and VL-CDR3 polypeptide sequences related to the polypeptides shown in FIG. 1. While FIG. 1 shows VL-CDRs defined by the Kabat system, other CDR definitions, e.g., VL-CDRs defined by the Chothia system, are also included in the present invention. In one embodiment, the amino acid sequence of the reference VL CDR1 is SEQ ID NO: 26, 32 or 38; the amino acid sequence of the reference VL CDR2 is SEQ ID NO: 27, 33 or 39; and the amino acid sequence of the reference VL CDR3 is SEQ ID NO: 28, 34 or 40.

In another embodiment, the present invention provides an isolated polypeptide comprising, consisting essentially of, or consisting of an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in FIG. 1. In one embodiment, the amino acid sequence of the VL CDR1 is SEQ ID NO: 26, 32 or 38; the amino acid sequence of the VL CDR2 is SEQ ID NO: 27, 33 or 39; and the amino acid sequence of the VL CDR3 is SEQ ID NO: 28, 34 or 40.

In another embodiment, the present invention provides an isolated polypeptide comprising, consisting essentially of, or consisting of an immunoglobulin heavy chain variable region (VL) in which the VL-CDR1, VL-CDR2 and VL-CDR3 regions have polypeptide sequences which are identical to the VL-CDR1, VL-CDR2 and VL-CDR3 groups shown in FIG. 1, except for one, two, three, four, five, six, seven, eight, nine, or ten amino acid substitutions in any one VL-CDR. In certain embodiments the amino acid substitutions are conservative. In one embodiment, the amino acid sequence of the VL CDR1 is SEQ ID NO: 26, 32 or 38; the amino acid sequence of the VL CDR2 is SEQ ID NO: 27, 33 or 39; and the amino acid sequence of the VL CDR3 is SEQ ID NO: 28, 34 or 40.

An immunoglobulin or its encoding cDNA may be further modified. Thus, in a further embodiment the method of the present invention comprises any one of the step(s) of producing a chimeric antibody, murinized antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)2, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

Additionally, the present invention encompasses peptides including those containing a binding molecule as described above, for example containing the CDR3 region of the variable region of any one of the mentioned antibodies, in particular CDR3 of the heavy chain since it has frequently been observed that heavy chain CDR3 (HCDR3) is the region having a greater degree of variability and a predominant participation in antigen-antibody interaction. Such peptides may easily be synthesized or produced by recombinant means to produce a binding agent useful according to the invention. Such methods are well known to those of ordinary skill in the art. Peptides can be synthesized for example, using automated peptide synthesizers which are commercially available. The peptides can also be produced by recombinant techniques by incorporating the DNA expressing the peptide into an expression vector and transforming cells with the expression vector to produce the peptide.

Hence, the present invention relates to any binding molecule, e.g., an antibody or binding fragment thereof which is oriented towards the human anti-tau antibodies of the present invention and display the mentioned properties, i.e. which specifically recognize tau. Such antibodies and binding molecules can be tested for their binding specificity and affinity by ELISA and Western Blot and immunohistochemistry as described herein, see, e.g., the Examples. Furthermore, preliminary results of subsequent experiments performed in accordance with the present invention revealed that the human ant-tau antibody of the present invention, in particular antibody NI-105.4E4 binds primarily to pathologically aggregated tau resembling neurofibrillary tangles (NFT), neuropil threads present on human brain sections of patients who suffered from Alzheimer's disease (AD) in addition. Thus, in a particular preferred embodiment of the present invention, the human antibody or binding fragment, derivative or variant thereof recognizes tau on human AD brain sections. Moreover, the distinct ability of the antibody NI-105.4E4 to differentially bind to tau pathologies could also be shown in transgenic mouse overexpressing human tau P301L. In addition to the already mentioned NFT's and neuropil threads the antibody NI-105.4E4 binds on mouse brain sections also dystrophic neurites and identifies tau aggregates at pre-tangle stage; see Example 4 and FIG. 6.

As an alternative to obtaining immunoglobulins directly from the culture of immortalized B cells or B memory cells, the immortalized cells can be used as a source of rearranged heavy chain and light chain loci for subsequent expression and/or genetic manipulation. Rearranged antibody genes can be reverse transcribed from appropriate mRNAs to produce cDNA. If desired, the heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Once the genetic material is available, design of analogs as described above which retain both their ability to bind the desired target is straightforward. Methods for the cloning of antibody variable regions and generation of recombinant antibodies are known to the person skilled in the art and are described, for example, Gilliland et al., Tissue Antigens 47 (1996), 1-20; Doenecke et al., Leukemia 11 (1997), 1787-1792.

Once the appropriate genetic material is obtained and, if desired, modified to encode an analog, the coding sequences, including those that encode, at a minimum, the variable regions of the heavy and light chain, can be inserted into expression systems contained on vectors which can be transfected into standard recombinant host cells. A variety of such host cells may be used; for efficient processing, however, mammalian cells may be considered. Typical mammalian cell lines useful for this purpose include, but are not limited to, CHO cells, HEK 293 cells, or NSO cells.

The production of the antibody or analog is then undertaken by culturing the modified recombinant host under culture conditions appropriate for the growth of the host cells and the expression of the coding sequences. The antibodies are then recovered by isolating them from the culture. The expression systems are designed to include signal peptides so that the resulting antibodies are secreted into the medium; however, intracellular production is also possible.

In accordance with the above, the present invention also relates to a polynucleotide encoding the antibody or equivalent binding molecule of the present invention In one embodiment, the polynucleotide encodes at least a variable region of an immunoglobulin chain of the antibody described above. Typically, said variable region encoded by the polynucleotide comprises at least one complementarity determining region (CDR) of the VH and/or VL of the variable region of the said antibody.

The person skilled in the art will readily appreciate that the variable domain of the antibody having the above-described variable domain can be used for the construction of other polypeptides or antibodies of desired specificity and biological function. Thus, the present invention also encompasses polypeptides and antibodies comprising at least one CDR of the above-described variable domain and which advantageously have substantially the same or similar binding properties as the antibody described in the appended examples. The person skilled in the art knows that binding affinity may be enhanced by making amino acid substitutions within the CDRs or within the hypervariable loops (Chothia and Lesk, J. Mol. Biol. 196 (1987), 901-917) which partially overlap with the CDRs as defined by Kabat; see, e.g., Riechmann, et al, Nature 332 (1988), 323-327. Thus, the present invention also relates to antibodies wherein one or more of the mentioned CDRs comprise one or more, or not more than two amino acid substitutions. In one embodiment, the antibody of the invention comprises in one or both of its immunoglobulin chains two or all three CDRs of the variable regions as set forth in FIG. 1.

Binding molecules, e.g., antibodies, or antigen-binding fragments, variants, or derivatives thereof of the invention, as known by those of ordinary skill in the art, can comprise a constant region which mediates one or more effector functions. For example, binding of the C1 component of complement to an antibody constant region may activate the complement system. Activation of complement is important in the opsonization and lysis of cell pathogens. The activation of complement also stimulates the inflammatory response and may also be involved in autoimmune hypersensitivity. Further, antibodies bind to receptors on various cells via the Fc region, with a Fc receptor binding site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

Accordingly, certain embodiments of the present invention include an antibody, or antigen-binding fragment, variant, or derivative thereof, in which at least a fraction of one or more of the constant region domains has been deleted or otherwise altered so as to provide desired biochemical characteristics such as reduced effector functions, the ability to non-covalently dimerize, increased ability to localize at the site of tau aggregation and deposition, reduced serum half-life, or increased serum half-life when compared with a whole, unaltered antibody of approximately the same immunogenicity. For example, certain antibodies for use in the diagnostic and treatment methods described herein are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted. In other embodiments, certain antibodies for use in the diagnostic and treatment methods described herein have a constant region, e.g., an IgG heavy chain constant region, which is altered to eliminate glycosylation, referred to elsewhere herein as aglycosylated or "agly" antibodies. Such "agly" antibodies may be prepared enzymatically as well as by engineering the consensus glycosylation site(s) in the constant region. While not being bound by theory, it is believed that "agly" antibodies may have an improved safety and stability profile in vivo. Methods of producing aglycosylated antibodies, having desired effector function are found for example in international application WO2005/018572, which is incorporated by reference in its entirety.

In certain antibodies, or antigen-binding fragments, variants, or derivatives thereof described herein, the Fc portion may be mutated to decrease effector function using techniques known in the art. For example, the deletion or inactivation (through point mutations or other means) of a constant region domain may reduce Fc receptor binding of the circulating modified antibody thereby increasing tau localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tau localization, biodistribution and serum half-life, may easily be measured and quantified using well know immunological techniques without undue experimentation.

In certain antibodies, or antigen-binding fragments, variants, or derivatives thereof described herein, the Fc portion may be mutated or exchanged for alternative protein sequences to increase the cellular uptake of antibodies by way of example by enhancing receptor-mediated endocytosis of antibodies via Fcγ receptors, LRP, or Thy1 receptors or by 'SuperAntibody Technology', which is said to enable antibodies to be shuttled into living cells without harming them (Expert Opin. Biol. Ther. (2005), 237-241). For example, the generation of fusion proteins of the antibody binding region and the cognate protein ligands of cell surface receptors or bi- or multi-specific antibodies with a specific sequences biding to tau as well as a cell surface receptor may be engineered using techniques known in the art.

In certain antibodies, or antigen-binding fragments, variants, or derivatives thereof described herein, the Fc portion may be mutated or exchanged for alternative protein sequences or the antibody may be chemically modified to increase its blood brain barrier penetration.

Modified forms of antibodies, or antigen-binding fragments, variants, or derivatives thereof of the invention can be made from whole precursor or parent antibodies using techniques known in the art. Exemplary techniques are discussed in more detail herein. Antibodies, or antigen-binding fragments, variants, or derivatives thereof of the invention can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail elsewhere herein.

Antibodies, or antigen-binding fragments, variants, or derivatives thereof of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In particular embodiments, antibodies, or antigen-binding fragments, variants, or derivatives thereof of the invention will not elicit a deleterious immune response in the animal to be treated, e.g., in a human. In certain embodiments, binding molecules, e.g., antibodies, or antigen-binding fragments thereof of the invention are derived from a patient, e.g., a human patient, and are subsequently used in the same species from which they are derived, e.g., human, alleviating or minimizing the occurrence of deleterious immune responses.

De-immunization can also be used to decrease the immunogenicity of an antibody. As used herein, the term "de-immunization" includes alteration of an antibody to modify T cell epitopes; see, e.g., international applications WO98/52976 and WO00/34317. For example, VH and VL sequences from the starting antibody are analyzed and a human T cell epitope "map" from each V region showing the location of epitopes in relation to complementarity determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., tau-specific antibodies or immunospecific fragments thereof for use in the diagnostic and treatment methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, Cold Spring Harbor Laboratory Press, 2nd ed. (1988); Hammerling et al., in: Monoclonal Antibodies and T-Cell Hybridomas Elsevier, N.Y., 563-681 (1981), said references incorporated by reference in their entireties. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. In certain embodiments, antibodies of the present invention are derived from human B cells which have been immortalized via transformation with Epstein-Barr virus, as described herein.

In the well-known hybridoma process (Kohler et al., Nature 256 (1975), 495) the relatively short-lived, or mortal, lymphocytes from a mammal, e.g., B cells derived from a human subject as described herein, are fused with an immortal tumor cell line (e.g., a myeloma cell line), thus, producing hybrid cells or "hybridomas" which are both immortal and capable of producing the genetically coded antibody of the B cell. The resulting hybrids are segregated into single genetic strains by selection, dilution, and re-growth with each individual strain comprising specific genes for the formation of a single antibody. They produce antibodies, which are homogeneous against a desired antigen and, in reference to their pure genetic parentage, are termed "monoclonal".

Hybridoma cells thus prepared are seeded and grown in a suitable culture medium that contain one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. The binding specificity of the monoclonal antibodies produced by hybridoma cells is determined by in vitro assays such as immunoprecipitation, radioimmunoassay (RIA) or enzyme-linked immunoabsorbent assay (ELISA) as described herein. After hybridoma cells are identified that produce antibodies of the desired specificity, affinity and/or activity, the clones may be subcloned by limiting dilution procedures and grown by standard methods; see, e.g., Goding, Monoclonal Antibodies: Principles and Practice, Academic Press, pp 59-103 (1986). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, lymphocytes can be selected by micromanipulation and the variable genes isolated. For example, peripheral blood mononuclear cells can be isolated from an immunized or naturally immune mammal, e.g., a human, and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Antibody fragments that recognize specific epitopes may be generated by known techniques. For example, Fab and F(ab')2 fragments may be produced recombinantly or by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Such fragments are sufficient for use, for example, in immunodiagnostic procedures involving coupling the immunospecific portions of immunoglobulins to detecting reagents such as radioisotopes.

Human antibodies, such as described herein, are particularly desirable for therapeutic use in human patients. Human antibodies of the present invention are isolated, e.g., from healthy human subjects who because of their age may be suspected to be at risk of developing a tauopathic disorder, e.g., Alzheimer's disease, or a patient with the disorder but with an unusually stable disease course. However, though it is prudent to expect that elderly healthy and symptom-free subjects, respectively, more regularly will have developed protective anti-tau antibodies than younger subjects, the latter may be used as well as source for obtaining a human antibody of the present invention. This is particularly true for younger patients who are predisposed to develop a familial form of a tauopathic disease but remain symptom-free since their immune system functions more efficiently than that in older adults.

In one embodiment, an antibody of the invention comprises at least one heavy or light chain CDR of an antibody molecule. In another embodiment, an antibody of the invention comprises at least two CDRs from one or more antibody molecules. In another embodiment, an antibody of the invention comprises at least three CDRs from one or more antibody molecules. In another embodiment, an antibody of the invention comprises at least four CDRs from one or more antibody molecules. In another embodiment, an antibody of the invention comprises at least five CDRs from one or more antibody molecules. In another embodiment, an antibody of the invention comprises at least six CDRs from one or more antibody molecules. Exemplary antibody molecules comprising at least one CDR that can be included in the subject antibodies are described herein.

Antibodies of the present invention can be produced by any method known in the art for the synthesis of antibodies, in particular, by chemical synthesis or by recombinant expression techniques as described herein.

In one embodiment, an antibody, or antigen-binding fragment, variant, or derivative thereof of the invention comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide may be substituted for the deleted domain to provide flexibility and freedom of movement for the variable region. Those skilled in the art will appreciate that such constructs are particularly preferred due to the regulatory properties of the CH2 domain on the catabolic rate of the antibody. Domain deleted constructs can be derived using a vector encoding an IgG1 human constant domain, see, e.g., international applications WO02/060955 and WO02/096948A2. This vector is engineered to delete the CH2 domain and provide a synthetic vector expressing a domain deleted IgG1 constant region.

In certain embodiments, antibodies, or antigen-binding fragments, variants, or derivatives thereof of the present invention are minibodies. Minibodies can be made using methods described in the art, see, e.g., U.S. Pat. No. 5,837,821 or international application WO 94/09817.

In one embodiment, an antibody, or antigen-binding fragment, variant, or derivative thereof of the invention comprises an immunoglobulin heavy chain having deletion or substitution of a few or even a single amino acid as long as it permits association between the monomeric subunits. For example, the mutation of a single amino acid in selected areas of the CH2 domain may be enough to substantially reduce Fc binding and thereby increase tau localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be synthetic through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

The present invention also provides antibodies that comprise, consist essentially of, or consist of, variants (including derivatives) of antibody molecules (e.g., the VH regions and/or VL regions) described herein, which antibodies or fragments thereof immunospecifically bind to tau. Standard techniques known to those of skill in the art can be used to introduce mutations in the nucleotide sequence encoding an antibody, including, but not limited to, site-directed mutagenesis and PCR-mediated mutagenesis which result in amino acid substitutions. In one embodiment, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VH-CDR1, VH-CDR2, VH-CDR3, VL region, VL-CDR1, VL-CDR2, or VL-CDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind tau).

For example, it is possible to introduce mutations only in framework regions or only in CDR regions of an antibody molecule. Introduced mutations may be silent or neutral missense mutations, e.g., have no, or little, effect on an antibody's ability to bind antigen, indeed some such mutations do not alter the amino acid sequence whatsoever. These types of mutations may be useful to optimize codon usage, or improve a hybridoma's antibody production. Codon-optimized coding regions encoding antibodies of the present invention are disclosed elsewhere herein. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein may routinely be expressed and the functional and/or biological activity of the encoded protein, (e.g., ability to immunospecifically bind at least one epitope of tau) can be determined using techniques described herein or by routinely modifying techniques known in the art.

Tau binding agents, for example, but not limited to, tau binding antibodies of the present invention may be characterized using any in vivo or in vitro models of neurodegenerative tauopathies. A skilled artisan readily understands that a tau binding agent (e.g., an antibody) of the invention may be characterized in a mouse model for neurodegenerative tauopathies. for example, but not limited to, any one of the following three different animal models for tauopathies may be used to characterize and validate the tau antibodies (and molecules with the binding specificities thereof) of the present invention.

1. Transgenic TauP301L mice (line 183): expressing human Tau40 with P301L mutation under the murine Thy1.2 promoter (Generation of these transgenic animals is described in Götz et al., J. Biol. Chem. 276 (2001), 529-534 and in international application WO 2003/017918, the disclosure content of which is incorporated herein by reference)

2. JNPL3 mice expressing the shortest human tau isoform with P301L mutation under the murine PrP promoter (available from Taconic, Hudson, N.Y., U.S.A).

3. P301STau (line PS19) mice expressing human tau with P301S mutation under the murine PrP promoter (available from the Jackson Laboratory, Bar Harbor, Me., U.S.A).

A skilled artisan understands that an experimental model of neurodegenerative tauopathies may be used in a preventative setting or it may be used in a therapeutic setting. In a preventative setting, the dosing of animals starts prior to the onset of the neurodegenerative tauopathies or symptoms thereof. In preventative settings, a tau binding agent (e.g., antibody) of the invention is evaluated for its ability to prevent, reduce or delay the onset of neurodegenerative tauopathies or symptoms thereof. In a therapeutic setting, the dosing of animals start after the onset of neurodegenerative tauopathies or a symptom thereof. In a therapeutic setting, a tau binding agent (e.g., antibody) of the invention is evaluated for its ability to treat, reduce or alleviate the neurodegenerative tauopathies or a symptom thereof. Symptoms of the neurodegenerative tauopathies include, but are not limited to, accumulation of pathological tau deposits, neurofibrillary tangles (NFT), hyperphosphorylated tau polypeptide, insoluble tau fractions in the neurons, brain, spinal cord, cerebrospinal fluid or serum of the experimental object. A skilled artisan understands that a positive preventative or therapeutic outcome in any animal model of neurodegenerative tauopathies indicates that the particular tau binding agent (e.g., antibody) may be used for preventative or therapeutic purposes in a subject other than the experimental model organism, for example, it may be used to treat neurodegenerative tauopathies in a human subject in need thereof.

In one embodiment, a tau binding agent (e.g., an antibody) of the invention may be administered to a tauopathy mouse model and corresponding control wild type mice. The antibody administered may be a murinized antibody of the present invention or a human-murine chimera of an antibody of the present invention. See, for example, Example 6 and 7. The tau binding agent (e.g., an antibody) may be administered by any means known in the art, for example, by intraperitoneal, intracranial, intramuscular, intravenous, subcutaneous, oral, and aerosol administration. Experimental animals may be given one, two, three, four, five or more doses of the tau binding agent (e.g., an antibody) or a control composition, such as PBS. In one embodiment, experimental animals will be administered one or two doses of a tau binding agent (e.g., an antibody). See, for example, Example 9. In another embodiment, the animals are chronically dosed with the tau binding agent (e.g., an antibody) over several weeks or months. See, for example, Example 10. A skilled artisan can readily design a dosing regimen that fits the experimental purpose, for example, dosing regimen for acute studies, dosing regimen for chronic studies, dosing regimen for toxicity studies, dosing regimen for preventative or therapeutic studies. The presence of the tau binding agent (e.g., antibody) in a particular tissue compartment of the experimental animals, for example, but not limited to, serum, blood, cerebrospinal fluid, brain tissue, may be established using well know methods of the art. See, for example, Example 9 and 10. In one embodiment, a tau binding agent (e.g., antibody) of the invention is capable to penetrate the blood brain barrier. A skilled artisan understands that by adjusting the tau binding agent (e.g., antibody) dose and the dosing frequency, a desired tau binding agent (e.g., antibody) concentration may be maintained in the experimental animals. Any effect of a tau binding agent (e.g., antibody) of the present invention in the tauopathy models may be assessed by comparing the level, biochemical characteristics or distribution of tau in the treated and control animals. In one example, the neurofibrillary tangles (NFT) are examined using the silver impregnation technique of Gallyas or by immunostaining with monoclonal mouse antibody AT100 and AT180, which recognize pathologically phosphorylated tau in NFT. The number or frequency of Gallyas-positive neurons and/or AT100, AT180 labeled neurons in the brain and spinal cord in antibody treated mice and control animals may be determined to evaluate the effect of antibody treatment. In one embodiment, an antibody of the present invention is capable of reducing the level, amount or concentration of neurofibrillary tangles in the brain or spinal cord in an animal model. The antibody may reduce the level, amount or concentration of neurofibrillary tangles by at least about 5%, 10%, 20%, 30%, 50%, 70%, 90% or more. In another embodiment, an antibody of the present invention is capable of reducing the number or frequency of Gallyas-positive neurons in the brain or spinal cord in an animal model, for example, by at least about 5%, 10%, 20%, 30%, 50%, 70%, 90% or more. In a further embodiment, an antibody of the present invention is capable of reducing the number or frequency of AT100 or AT180 antibody positive neurons in the brain or spinal cord in an animal model, for example, by at least about 5%, 10%, 20%, 30%, 50%, 70%, 90% or more. The effect of an antibody of the present invention may also be assessed by examining the distribution and biochemical properties of tau following antibody administration. In one embodiment, an antibody of the present invention is capable of reducing the amount or concentration of tau protein in the brain or spinal cord of an animal model, for example, by at least about 5%, 10%, 20%, 30%, 50%, 70%, 90% or more. In another embodiment, an antibody of the present invention is capable of reducing the amount or concentration of insoluble tau protein in the brain or spinal cord of an animal model, for example, by at least about 5%, 10%, 20%, 30%, 50%, 70%, 90% or more. Insoluble tau fraction may be prepared as described, for example, in Example 10 or in Goedert M, Spillantini M G, Cairns N J, Crowther R A. Neuron 8, 159 (1992). The amount of tau protein in a biological sample may be determined by any method known to one of skill, for example, as described in Example 10. In a further embodiment, an antibody of the present invention may reduce the amount or concentration of hyperphosphorylated tau protein in the brain or spinal cord in an animal model, for example, by at least about 5%, 10%, 20%, 30%, 50%, 70%, 90% or more. Hyperphosphorylated tau may be detected using antibodies specific for pathologically hyperphosphorylated forms of tau, such as AT100 or AT180. An antibody of the present invention may also reduce tau concentration in the blood, serum or cerebrospinal fluid or an animal model, for example, by at least about 5%, 10%, 20%, 30%, 50%, 70%, 90% or more. In one embodiment, the % reduction is relative compared to the level, number, frequency, amount or concentration that existed before treatment, or to the level, number, frequency, amount or concentration that exist in an untreated/control treated subject.

In one embodiment, an antibody of the present invention may prevent or delay the onset of at least one symptom of a neurodegenerative tauopathy in a subject. In one embodiment, an antibody of the present invention may reduce or eliminate at least one symptom of a neurodegenerative tauopathy in a subject. The symptom may be the formation of pathological tau deposits, hyperphosphorylated tau deposits, insoluble tau deposits, neurofibrillary fibers, neurofibrillary fibers, pre-tangle phosphor tau aggregates, intraneuronal neurofibrillary tangles or extraneuronal neurofibrillary tangles in the brain or spinal cord of a subject. See, e.g., Augustinack et al, Acta Neuropathol 103:26-35 (2002). The symptom may also be the presence, or elevated concentration or amount, of tau in the serum, blood, urine or cerebrospinal fluid, wherein elevated concentration amount is compared to a healthy subject. The symptom may be a neurological symptom, for example, altered conditioned taste aversion, altered contextual fear conditioning, memory impairment, loss of motor function. In one embodiment, memory impairment is assessed using a two-trial Y-maze task. In one embodiment, the at least one symptom is reduced by at least about 5%, 10%, 15%, 20%, 30%, 50%, 70%, or 90%. The present invention also provides a method of preventing or delaying the onset of at least one symptom of a neurodegenerative tauopathy in a subject in need thereof, comprising administering a therapeutically effective amount of a tau antibody described herein. The present invention further provides a method of reducing or eliminating least one symptom of a neurodegenerative tauopathy in a subject in need thereof, comprising administering a therapeutically effective amount of a tau antibody described herein. In one embodiment, the subject is an experimental organism, such as, but not limited to, transgenic mouse. In one embodiment, the subject is a human.

III. Polynucleotides Encoding Antibodies

A polynucleotide encoding an antibody, or antigen-binding fragment, variant, or derivative thereof can be composed of any polyribonucleotide or polydeoxyribonucleotide, which may be unmodified RNA or DNA or modified RNA or DNA. For example, a polynucleotide encoding an antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an antibody, or antigen-binding fragment, variant, or derivative thereof can be composed of triple-stranded regions comprising RNA or DNA or both RNA and DNA. A polynucleotide encoding an antibody, or antigen-binding fragment, variant, or derivative thereof may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. In one embodiment, conservative amino acid substitutions are made at one or more non-essential amino acid residues.

As is well known, RNA may be isolated from the original B cells, hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art. In one embodiment, cDNAs that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as human constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90%, 95%, 96%, about 97%, 98%, or 99% identical to reference heavy chain VH-CDR1, VH-CDR2, or VH-CDR3 amino acid sequences from the antibodies disclosed herein. Alternatively, the VH-CDR1, VH-CDR2, or VH-CDR3 regions of the VH are at least 80%, 85%, 90%, 95%, 96%, about 97%, 98%, or 99% identical to reference heavy chain VH-CDR1, VH-CDR2, and VH-CDR3 amino acid sequences from the antibodies disclosed herein. Thus, according to this embodiment a heavy chain variable region of the invention has VH-CDR1, VH-CDR2, or VH-CDR3 polypeptide sequences related to the polypeptide sequences shown in FIG. 1. In one embodiment, the amino acid sequence of the reference VH CDR1 is SEQ ID NO: 23, 29, or 35; the amino acid sequence of the reference VH CDR2 is SEQ ID NO: 24, 30 or 36; and the amino acid sequence of the reference VH CDR3 is SEQ ID NO: 25, 31 or 37.

In one embodiment, the present invention provides an isolated polynucleotide comprising, consisting essentially of, or consisting of a nucleic acid encoding an immunoglobulin heavy chain variable region (VH), in which the VH-CDR1, VH-CDR2 and VH-CDR3 regions have polypeptide sequences which are identical to the VH-CDR1, VH-CDR2 and VH-CDR3 groups shown in FIG. 1, except for one, two, three, four, five, six, seven, eight, nine, or ten amino acid substitutions in any one VH-CDR. In certain embodiments the amino acid substitutions are conservative. In one embodiment, the amino acid sequence of the VH CDR1 is SEQ ID NO: 23, 29, or 35; the amino acid sequence of the VH CDR2 is SEQ ID NO: 24, 30 or 36; and the amino acid sequence of the VH CDR3 is SEQ ID NO: 25, 31 or 37.

In another embodiment, the present invention provides an isolated polynucleotide comprising, consisting essentially of, or consisting of a nucleic acid encoding an immunoglobulin light chain variable region (VL), where at least one of the VL-CDRs of the light chain variable region or at least two of the VL-CDRs of the light chain variable region are at least 80%, 85%, 90%, 95%, 96%, about 97%, 98%, or 99% identical to reference light chain VL-CDR1, VL-CDR2, or VL-CDR3 amino acid sequences from the antibodies disclosed herein. Alternatively, the VL-CDR1, VL-CDR2, or VL-CDR3 regions of the VL are at least 80%, 85%, 90%, 95%, 96%, about 97%, 98%, or 99% identical to reference light chain VL-CDR1, VL-CDR2, and VL-CDR3 amino acid sequences from the antibodies disclosed herein. Thus, according to this embodiment a light chain variable region of the invention has VL-CDR1, VL-CDR2, or VL-CDR3 polypeptide sequences related to the polypeptide sequences shown in FIG. 1. In one embodiment, the amino acid sequence of the reference VL CDR1 is SEQ ID NO: 26, 32 or 38; the amino acid sequence of the reference VL CDR2 is SEQ ID NO: 27, 33 or 39; and the amino acid sequence of the reference VL CDR3 is SEQ ID NO: 28, 34 or 40.

In another embodiment, the present invention provides an isolated polynucleotide comprising, consisting essentially of, or consisting of a nucleic acid encoding an immunoglobulin light chain variable region (VL) in which the VL-CDR1, VL-CDR2 and VL-CDR3 regions have polypeptide sequences which are identical to the VL-CDR1, VL-CDR2 and VL-CDR3 groups shown in FIG. 1, except for one, two, three, four, five, six, seven, eight, nine, or ten amino acid substitutions in any one VL-CDR. In certain embodiments the amino acid substitutions are conservative. In one embodiment, the amino acid sequence of the VL CDR1 is SEQ ID NO: 26, 32 or 38; the amino acid sequence of the VL CDR2 is SEQ ID NO: 27, 33 or 39; and the amino acid sequence of the VL CDR3 is SEQ ID NO: 28, 34 or 40.

In another embodiment, the present invention provides an isolated polynucleotide comprising, consisting essentially of, or consisting of a nucleic acid encoding an immunoglobulin light chain variable region (VH) in which the VH-CDR1, VH-CDR2, and VH-CDR3 regions have polypeptide sequences which are identical to the VH-CDR1, VH-CDR2, and VH-CDR3 groups shown in FIG. 1. In one embodiment, the amino acid sequence of the VH CDR1 is SEQ ID NO: 23, 29, or 35; the amino acid sequence of the VH CDR2 is SEQ ID NO: 24, 30 or 36; and the amino acid sequence of the VH CDR3 is SEQ ID NO: 25, 31 or 37.

In another embodiment, the present invention provides an isolated polynucleotide comprising, consisting essentially of, or consisting of a nucleic acid encoding an immunoglobulin heavy chain variable region (VL) in which the VL-CDR1, VL-CDR2, and VL-CDR3 regions have polypeptide sequences which are identical to the VL-CDR1, VL-CDR2, and VL-CDR3 groups shown in FIG. 1. In one embodiment, the amino acid sequence of the VL CDR1 is SEQ ID NO: 26, 32 or 38; the amino acid sequence of the VL CDR2 is SEQ ID NO: 27, 33 or 39; and the amino acid sequence of the VL CDR3 is SEQ ID NO: 28, 34 or 40.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In one embodiment of the present invention, the polynucleotide comprises, consists essentially of, or consists of a nucleic acid having a polynucleotide sequence of the VH or VL region of an anti-tau antibody as depicted in Table 2. In this respect, the person skilled in the art will readily appreciate that the polynucleotides encoding at least the variable domain of the light and/or heavy chain may encode the variable domain of both immunoglobulin chains or only one. The present invention further provides a polynucleotide comprising, or consisting of a nucleotide sequence encoding the amino acid sequence of SEQ ID: 93.

TABLE 2

Nucleotide sequences of the $V_H$ and $V_L$ region of tau specific antibodies.

| Antibody | Nucleotide sequences of variable heavy (VH) and variable light (VL) chains |
|---|---|
| NI-105.4E4-$V_H$ SEQ ID NO: 8 | GAGGTGCAGCTGGTGGAGTCTGGGGGAGGCTTGGTCCAGCCTGGGGGATC CCTGAAACTCTCCTGTGCAGCCTCTGGGTTCAATTTCAACATCTCTGCTA TACACTGGGTCCGCCAGGCTTCCGGGAAAGGGCTGGAGTGGGTTGGCCGA ATAAGAAGTAAATCTCACAATTACGCGACTTTATATGCTGCGTCCCTGAA AGGCCGGTTCACCCTCTCCAGAGATGATTCAAGGAACACGGCGTATCTGC AAATGAGCAGCCTGCAAACCGAGGATATGGCCGTCTATTACTGTACTGTT CTGAGTGCGAATTACGACACCTTTGACTACTGGGGCCAGGGAACCCTGGT CACCGTCTCCTCG |
| NI-105.4E4-$V_L$ SEQ ID NO: 10 | TCCTATGAGCTGACTCAGCCACCCTCGGTGTCAGTGTCCCCAGGACAGAC GGCCAGGATCTCCTGCTTTGGAGATACATTGCCAAAGCAATATACTTATT GGTATCAGCAGAAGCCTGGCCAGGCCCCTGTGTTAGTGATTTATAAAGAC ACTGAGAGGCCCTCAGGGATCCCCGAGCGATTCTCTGGCTCCAGCTCAGG GACAACAGTCACCTTGACCATCAGTGGAGTCCAGGCAGAAGACGAGGCTG ACTATTACTGTCTATCAGCTGACAACAGTGCTACTTGGGTGTTCGGCGGA GGGACCAAGGTGACCGTCCTA |
| NI-105.24B2-$V_H$ SEQ ID NO: 12 | CAGGTGCAGCTGGTGCAGTCTGGGGCTGAGGTGAAGAAGCCTGGGGCCTC GGTGAAGGTTTCCTGTAAGGCATCTGGATACACCTTCGTCAATTACATTA TACACTGGGTGCGACAGGCCCCTGGACAAGGGCTTGAGTGGATGGGAATC ATCAATCCTAATGGCGGAAACACAAGTTATGCAGAGAAATTCCAGGCCCG AGTCACCTTGACCAGCGACACGTCTACGAGTACGGTGTACATGGACCTGA GCAGCCTGACATCTGAGGACACGGCCGTCTATTACTGTGCCGTCCTTTCC CCTTCGAATCCCTGGGGCCAGGGGACCACGGTCACCGTCTCCTCG |

TABLE 2-continued

Nucleotide sequences of the V_H and V_L region of tau specific antibodies.

| Antibody | Nucleotide sequences of variable heavy (VH) and variable light (VL) chains |
|---|---|
| NI-105.24B2-V_L SEQ ID NO: 14 | TCCTATGAGCTGACTCAGCCACCCTCGGTGTCAGTGTCCCCAGGACAGAC GGCCGGGATCACCTGCTCTGGAGATGCTTTGCCAAAGCAATTTGTTTATT GGTACCAGAAGAAGCCAGGCCAGGCCCCTGTGTTATTGATATATAAAGAC ACTGAGAGGCCCTCACGAATCCCTGAGCGCTTCTCTGGCTCCACCTCAGG GACAACAGTCGCGTTGACCATCAATGGGGTCCAGGCAGAGGACGAGGCTG ACTATTACTGTCAATCAGCCGACCGCAGTGGTGCTCTTTGGGTGTTCGGC GGAGGGACCAAGCTGACCGTCCTA |
| NI-105.4A3-V_H SEQ ID NO: 16 | CAGGTGCAGCTGGTGGAGTCTGGGGGAGGCGCGGTCCAGCCTGGGGGGTC CCTGAGACTCTCCTGTGCAGCCTCTGGATTCACCTTCAGTGACTATGCCA TGCACTGGGTCCGCCAGGCTCCAGGCAAGGGGCTGCAGTGGGTGGCAGTT ATATCGTATGAGGGAACTTATAAATACTATGCAGACTCCGTGAAGGGCCG ATTCACCATCTCCAGAGACAATTCCAAGAACACGCTGAACTTGCAGATGA GCAGCCTGAGAGTTGAAGACACGGCTGTGTATTTCTGTGTGAAAGCTCGA GCCTTTGCCTCCGGACAGCGAAGCACCTCCACCGTACCTGACTACTGGGG CCAGGGAACCCTGGTCACCGTCTCCTCG |
| NI-105.4A3-V_L SEQ ID NO: 18 | TCCTATGAGCTGACTCAGCCACCCTCGGTGTCAGTGTCCCCAGGACAAAC GGCCAGGATCACCTGCTCTGGAGATGCATTGCCAAAAAAATATGCTTATT GGTACCAGCAGAAGTCAGGCCAGGCCCCTGTGTTGGTCATCTATGAGGAC AACAAACGACCCTCCGGGATCCCTGAGAGATTCTCTGGCTCCAGCTCAGG GACAGTGGCCACCTTGACTATCAGTGGGGCCCAGGTGGACGATGAAGCTG ACTACTACTGCTACTCGACAGACATCAGTGGTGACCTTCGGGTGTTCGGC GGAGGGACCAAGCTGACCGTCCTC |

In one embodiment, the present invention provides an isolated polynucleotide comprising, consisting essentially of, or consisting of a nucleic acid encoding an immunoglobulin heavy chain variable region at least 80%, 85%, 90%, 95%, 96%, about 97%, 98%, or 99% or 95% identical to reference heavy chain VH. In one embodiment, the amino acid sequence of the reference heavy chain variable region is SEQ ID NO: 9, 13, 17 or 93.

In one embodiment, the present invention provides an isolated polynucleotide comprising, consisting essentially of, or consisting of a nucleic acid encoding an immunoglobulin light chain variable region at least 80%, 85%, 90%, 95%, 96%, about 97%, 98%, or 99% or 95% identical to reference light chain VL. In one embodiment, the amino acid sequence of the reference light chain variable region is SEQ ID NO: 11, 15 or 19.

The present invention also includes fragments of the polynucleotides of the invention, as described elsewhere. Additionally polynucleotides which encode fusion polynucleotides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides, e.g., as described in Kutmeier et al., BioTechniques 17 (1994), 242, which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody, or antigen-binding fragment, variant, or derivative thereof may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably polyA+ RNA, isolated from, any tissue or cells expressing the tau-specific antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al., Molecular Cloning, A Laboratory Manual, 2d Ed., Cold Spring Harbor Laboratory, Cold Spring Harbor, N.Y. (1990) and Ausubel et al., eds., Current Protocols in Molecular Biology, John Wiley & Sons, NY (1998), which are both incorporated by reference herein in their entireties), to generate antibodies having a different amino acid sequence, for example to create amino acid substitutions, deletions, and/or insertions.

IV. Expression of Antibody Polypeptides

Following manipulation of the isolated genetic material to provide antibodies, or antigen-binding fragments, variants, or derivatives thereof of the invention, the polynucleotides encoding the antibodies are typically inserted in an expression vector for introduction into host cells that may be used to produce the desired quantity of antibody. Recombinant expression of an antibody, or fragment, derivative or analog thereof, e.g., a heavy or light chain of an antibody which binds to a target molecule is described herein. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., international applications WO 86/05807 and WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells. For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by co-transformation. Additional elements may also be needed for optimal synthesis of mRNA. These elements may include signal sequences, splice signals, as well as transcriptional promoters, enhancers, and termination signals.

In particular embodiments the cloned variable region genes are inserted into an expression vector along with the heavy and light chain constant region genes (e.g., human heavy and light chain constant region genes) as discussed above. In one embodiment, this is effected using a proprietary expression vector of Biogen IDEC, Inc., referred to as NEOSPLA, disclosed in U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those which express suitably high levels if immunoglobulin heavy and light chains is routine experimentation which can be carried out, for example, by robotic systems. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the antibodies, or antigen-binding fragments, variants, or derivatives thereof of the invention may be expressed using polycistronic constructs such as those disclosed in US patent application publication no. 2003-0157641 A1 and incorporated herein in its entirety. In these expression systems, multiple gene products of interest such as heavy and light chains of antibodies may be produced from a single polycistronic construct. These systems advantageously use an internal ribosome entry site (IRES) to provide relatively high levels of antibodies. Compatible IRES sequences are disclosed in U.S. Pat. No. 6,193,980 which is also incorporated herein. Those skilled in the art will appreciate that such expression systems may be used to effectively produce the full range of antibodies disclosed in the instant application.

More generally, once the vector or DNA sequence encoding a monomeric subunit of the antibody has been prepared, the expression vector may be introduced into an appropriate host cell. Introduction of the plasmid into the host cell can be accomplished by various techniques well known to those of skill in the art. These include, but are not limited to, transfection including lipotransfection using, e.g., Fugene® or lipofectamine, protoplast fusion, calcium phosphate precipitation, cell fusion with enveloped DNA, microinjection, and infection with intact virus. Typically, plasmid introduction into the host is via standard calcium phosphate co-precipitation method. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In particular embodiments for the expression of double-chained antibodies, vectors encoding both the heavy and light chains may be co-expressed in the host cell for expression of the entire immunoglobulin molecule, as detailed below.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain is advantageously placed before the heavy chain to avoid an excess of toxic free heavy chain; see Proudfoot, Nature 322 (1986), 52; Kohler, Proc. Natl. Acad. Sci. USA 77 (1980), 2197. The coding sequences for the heavy and light chains may comprise cDNA or genomic DNA.

As used herein, "host cells" refers to cells which harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, NSO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In one embodiment, bacterial cells such as *Escherichia coli*, and more preferably, eukaryotic cells, especially for the expression of whole recombinant antibody molecule, are used for the expression of a recombinant antibody molecule. For example, mammalian cells such as Chinese Hamster Ovary (CHO) cells, in conjunction with a vector such as the major intermediate early gene promoter element from human cytomegalovirus is an effective expression system for antibodies; see, e.g., Foecking et al., Gene 45 (1986), 101; Cockett et al., Bio/Technology 8 (1990), 2.

The host cell line used for protein expression is often of mammalian origin; those skilled in the art are credited with ability to determine particular host cell lines which are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, WI38, R1610 (Chinese hamster fibroblast) BALBC/3T3 (mouse fibroblast), HAK (hamster kidney line), SP2/0 (mouse myeloma), P3×63-Ag3.653 (mouse myeloma), BFA-1c1BPT (bovine endothelial cells), RAJI (human lymphocyte) and 293 (human kidney). In a specific embodiment, host cell lines are CHO or 293 cells. Host cell lines are typically available from commercial services, the American Tissue Culture Collection or from published literature.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including but not limited to the herpes simplex virus thymidine kinase (Wigler et al., Cell 11 (1977), 223), hypoxanthine-guanine phosphoribosyltransferase (Szybalska & Szybalski, Proc. Natl. Acad. Sci. USA 48 (1992), 202), and adenine phosphoribosyltransferase (Lowy et al., Cell 22 (1980), 817) genes can be employed in tk-, hgprt- or aprt-cells, respectively. Also, anti-metabolite resistance can be used as the basis of selection for the following genes: dhfr, which confers resistance to methotrexate (Wigler et al., Natl. Acad. Sci. USA 77 (1980), 357; O'Hare et al., Proc. Natl. Acad. Sci. USA 78 (1981), 1527); gpt, which confers resistance to mycophenolic acid (Mulligan & Berg, Proc. Natl. Acad. Sci. USA 78 (1981), 2072); neo, which confers resistance to the aminoglycoside G-418 Goldspiel et al., Clinical Pharmacy 12 (1993), 488-505; Wu and Wu, Biotherapy 3 (1991), 87-95; Tolstoshev, Ann. Rev. Pharmacol. Toxicol. 32 (1993), 573-596; Mulligan, Science 260 (1993), 926-932; and Morgan and Anderson, Ann Rev. Biochem. 62 (1993), 191-217; TIB TECH 11 (1993), 155-215; and hygro, which confers resistance to hygromycin (Santerre et al., Gene 30 (1984), 147. Methods commonly known in the art of recombinant DNA technology which can be used are described in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification, for a review, see Bebbington and Hentschel, The use of vectors based on gene amplification for the expression of cloned genes in mammalian cells in DNA cloning, Academic Press, New York, Vol. 3. (1987). When a marker in the vector system expressing antibody is amplifiable, increase in the level of inhibitor present in culture of host cell will increase the number of copies of the marker gene. Since the amplified region is associated with the antibody gene, production of the antibody will also increase; see Crouse et al., Mol. Cell. Biol. 3 (1983), 257.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding antibodies, or antigen-binding fragments, variants, or derivatives thereof of the invention can also be expressed in non-mammalian cells such as bacteria or insect or yeast or plant cells. Bacteria which readily take up nucleic acids include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies; see, e.g., international application WO02/096948.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2 (1983), 1791), in which the antibody coding sequence may be ligated individually into the vector in frame with the lacZ coding region so that a fusion protein is produced; pIN vectors (Inouye & Inouye, Nucleic Acids Res. 13 (1985), 3101-3109; Van Heeke & Schuster, J. Biol. Chem. 24 (1989), 5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix of glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*. For expression in *Saccharomyces*, the plasmid YRp7, for example, (Stinchcomb et al., Nature 282 (1979), 39; Kingsman et al., Gene 7 (1979), 141; Tschemper et al., Gene 10 (1980), 157) is commonly used. This plasmid already contains the TRP1 gene which provides a selection marker for a mutant strain of yeast lacking the ability to grow in tryptophan, for example ATCC No. 44076 or PEP4-1 (Jones, Genetics 85 (1977), 12). The presence of the trpl lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, the whole antibodies, their dimers, individual light and heavy chains, or other immunoglobulin forms of the present invention, can be purified according to standard procedures of the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Alternatively, another method for increasing the affinity of antibodies of the invention is disclosed in US patent publication 2002-0123057 A1.

V. Fusion Proteins and Conjugates

In certain embodiments, the antibody polypeptide comprises an amino acid sequence or one or more moieties not normally associated with an antibody. Exemplary modifications are described in more detail below. For example, a single-chain fv antibody fragment of the invention may comprise a flexible linker sequence, or may be modified to add a functional moiety (e.g., PEG, a drug, a toxin, or a label such as a fluorescent, radioactive, enzyme, nuclear magnetic, heavy metal and the like)

An antibody polypeptide of the invention may comprise, consist essentially of, or consist of a fusion protein. Fusion proteins are chimeric molecules which comprise, for example, an immunoglobulin tau-binding domain with at least one target binding site, and at least one heterologous portion, i.e., a portion with which it is not naturally linked in nature. The amino acid sequences may normally exist in separate proteins that are brought together in the fusion polypeptide or they may normally exist in the same protein but are placed in a new arrangement in the fusion polypeptide. Fusion proteins may be created, for example, by chemical synthesis, or by creating and translating a polynucleotide in which the peptide regions are encoded in the desired relationship.

The term "heterologous" as applied to a polynucleotide or a polypeptide, means that the polynucleotide or polypeptide is derived from a distinct entity from that of the rest of the entity to which it is being compared. For instance, as used herein, a "heterologous polypeptide" to be fused to an antibody, or an antigen-binding fragment, variant, or analog thereof is derived from a non-immunoglobulin polypeptide of the same species, or an immunoglobulin or non-immunoglobulin polypeptide of a different species.

As discussed in more detail elsewhere herein, antibodies, or antigen-binding fragments, variants, or derivatives thereof of the invention may further be recombinantly fused to a heterologous polypeptide at the N- or C-terminus or chemically conjugated (including covalent and non-covalent conjugations) to polypeptides or other compositions. For example, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

Antibodies, or antigen-binding fragments, variants, or derivatives thereof of the invention can be composed of amino acids joined to each other by peptide bonds or modified peptide bonds, i.e., peptide isosteres, and may contain amino acids other than the 20 gene-encoded amino acids. Antibodies may be modified by natural processes, such as posttranslational processing, or by chemical modification techniques which are well known in the art. Such modifications are well described in basic texts and in more detailed monographs, as well as in a voluminous research literature. Modifications can occur anywhere in the antibody, including the peptide backbone, the amino acid side-chains and the amino or carboxyl termini, or on moieties such as carbohydrates. It will be appreciated that the same type of modification may be present in the same or varying degrees at several sites in a given antibody. Also, a given antibody may contain many types of modifications. Antibodies may be branched, for example, as a result of ubiquitination, and they may be cyclic, with or without branching. Cyclic, branched, and branched cyclic antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, e.g., Proteins—Structure And Molecular Properties, T. E. Creighton, W. H. Freeman and Company, New York 2nd Ed., (1993); Posttranslational Covalent Modification Of Proteins, B. C. Johnson, Ed., Academic Press, New York, pgs. 1-12 (1983); Seifter et al., Meth. Enzymol. 182 (1990), 626-646; Rattan et al., Ann NY Acad. Sci. 663 (1992), 48-62).

The present invention also provides for fusion proteins comprising an antibody, or antigen-binding fragment, variant, or derivative thereof, and a heterologous polypeptide. In one embodiment, a fusion protein of the invention comprises, consists essentially of, or consists of, a polypeptide having the amino acid sequence of any one or more of the VH regions of an antibody of the invention or the amino acid sequence of any one or more of the VL regions of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the VH-CDRs of an antibody, or fragments, variants, or derivatives thereof, or the amino acid sequence of any one, two, three of the VL-CDRs of an antibody, or fragments, variants, or derivatives thereof, and a heterologous polypeptide sequence. In one embodiment, the fusion protein comprises a polypeptide having the amino acid sequence of a VH-CDR3 of an antibody of the present invention, or fragment, derivative, or variant thereof, and a heterologous polypeptide sequence, which fusion protein specifically binds to tau. In another embodiment, a fusion protein comprises a polypeptide having the amino acid sequence of at least one VH region of an antibody of the invention and the amino acid sequence of at least one VL region of an antibody of the invention or fragments, derivatives or variants thereof, and a heterologous polypeptide sequence. In one embodiment, the VH and VL regions of the fusion protein correspond to a single source antibody (or scFv or Fab fragment) which specifically binds tau. In yet another embodiment, a fusion protein for use in the diagnostic and treatment methods disclosed herein comprises a polypeptide having the amino acid sequence of any one, two, three or more of the VH CDRs of an antibody and the amino acid sequence of any one, two, three or more of the VL CDRs of an antibody, or fragments or variants thereof, and a heterologous polypeptide sequence. In one embodiment, two, three, four, five, six, or more of the VH-CDR(s) or VL-CDR(s) correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., Proc. Natl. Acad. Sci. USA 84 (1987), 2936-2940; CD4 (Capon et al., Nature 337 (1989), 525-531; Traunecker et al., Nature 339 (1989), 68-70; Zettmeissl et al., DNA Cell Biol. USA 9 (1990), 347-353; and Byrn et al., Nature 344 (1990), 667-670); L-selectin (homing receptor) (Watson et al., J. Cell. Biol. 110 (1990), 2221-2229; and Watson et al., Nature 349 (1991), 164-167); CD44 (Aruffo et al., Cell 61 (1990), 1303-1313); CD28 and B7 (Linsley et al., J. Exp. Med. 173 (1991), 721-730); CTLA-4 (Lisley et al., J. Exp. Med. 174 (1991), 561-569); CD22 (Stamenkovic et al., Cell 66 (1991), 1133-1144); TNF receptor (Ashkenazi et al., Proc. Natl. Acad. Sci. USA 88 (1991), 10535-10539; Lesslauer et al., Eur. J. Immunol. 27 (1991), 2883-2886; and Peppel et al., J. Exp. Med. 174 (1991), 1483-1489 (1991); and IgE receptor a (Ridgway and Gorman, J. Cell. Biol. 115 (1991), Abstract No. 1448).

As discussed elsewhere herein, antibodies, or antigen-binding fragments, variants, or derivatives thereof of the invention may be fused to heterologous polypeptides to increase the in vivo half life of the polypeptides or for use in immunoassays using methods known in the art. For example, in one embodiment, PEG can be conjugated to the antibodies of the invention to increase their half-life in vivo; see, e.g., Leong et al., Cytokine 16 (2001), 106-119; Adv. in Drug Deliv. Rev. 54 (2002), 531; or Weir et al., Biochem. Soc. Transactions 30 (2002), 512.

Moreover, antibodies, or antigen-binding fragments, variants, or derivatives thereof of the invention can be fused to marker sequences, such as a peptide to facilitate their purification or detection. In particular embodiments, the marker amino acid sequence is a hexa-histidine peptide (HIS), such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86 (1989), 821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37 (1984), 767) and the "flag" tag.

Fusion proteins can be prepared using methods that are well known in the art; see for example U.S. Pat. Nos. 5,116,964 and 5,225,538. The precise site at which the fusion is made may be selected empirically to optimize the secretion or binding characteristics of the fusion protein. DNA encoding the fusion protein is then transfected into a host cell for expression.

Antibodies of the present invention may be used in non-conjugated form or may be conjugated to at least one of a variety of molecules, e.g., to improve the therapeutic properties of the molecule, to facilitate target detection, or for imaging or therapy of the patient. Antibodies, or antigen-binding fragments, variants, or derivatives thereof of the invention can be labeled or conjugated either before or after purification, when purification is performed. In particular, antibodies, or antigen-binding fragments, variants, or derivatives thereof of the invention may be conjugated to therapeutic agents, prodrugs, peptides, proteins, enzymes, viruses, lipids, biological response modifiers, pharmaceutical agents, or PEG.

Conjugates that are immunotoxins including conventional antibodies have been widely described in the art. The toxins may be coupled to the antibodies by conventional coupling techniques or immunotoxins containing protein toxin portions can be produced as fusion proteins. The antibodies of the present invention can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

Those skilled in the art will appreciate that conjugates may also be assembled using a variety of techniques depending on the selected agent to be conjugated. For example, conjugates with biotin are prepared e.g. by reacting a tau binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, or fluorescein-isothiocyanate. Conjugates of the antibodies, or antigen-binding fragments, variants or derivatives thereof of the invention are prepared in an analogous manner.

The present invention further encompasses antibodies, or antigen-binding fragments, variants, or derivatives thereof of the invention conjugated to a diagnostic or therapeutic agent. The antibodies can be used diagnostically to, for example, demonstrate presence of a neurological disease, to indicate the risk of getting a neurological disease, to monitor the development or progression of a neurological disease, i.e. tauopathic disease as part of a clinical testing procedure to, e.g., determine the efficacy of a given treatment and/or prevention regimen. Detection can be facilitated by coupling the antibody, or antigen-binding fragment, variant, or derivative thereof to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions; see, e.g., U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

An antibody, or antigen-binding fragment, variant, or derivative thereof also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an antibody, or antigen-binding fragment, variant, or derivative thereof can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., Diagnostic Horizons 2 (1978), 1-7); Voller et al., J. Clin. Pathol. 31 (1978), 507-520; Butler, Meth. Enzymol. 73 (1981), 482-523; Maggio, E. (ed.), Enzyme Immunoassay, CRC Press, Boca Raton, Fla., (1980); Ishikawa, E. et al., (eds.), Enzyme Immunoassay, Kgaku Shoin, Tokyo (1981). The enzyme, which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibody, or antigen-binding fragment, variant, or derivative thereof, it is possible to detect the antibody through the use of a radioimmunoassay (RIA) (see, for example, Weintraub, B., Principles of Radioimmunoassays, Seventh Training Course on Radioligand Assay Techniques, The Endocrine Society, (March, 1986)), which is incorporated by reference herein). The radioactive isotope can be detected by means including, but not limited to, a gamma counter, a scintillation counter, or autoradiography.

An antibody, or antigen-binding fragment, variant, or derivative thereof can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an antibody, or antigen-binding fragment, variant, or derivative thereof are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al. (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", Immunol. Rev. 62 (1982), 119-158.

As mentioned, in certain embodiments, a moiety that enhances the stability or efficacy of a binding molecule, e.g., a binding polypeptide, e.g., an antibody or immunospecific fragment thereof can be conjugated. For example, in one embodiment, PEG can be conjugated to the binding molecules of the invention to increase their half-life in vivo. Leong et al., Cytokine 16 (2001), 106; Adv. in Drug Deliv. Rev. 54 (2002), 531; or Weir et al., Biochem. Soc. Transactions 30 (2002), 512.

VI. Compositions and Methods of Use

The present invention relates to compositions comprising the aforementioned tau binding molecule, e.g., antibody or antigen-binding fragment thereof of the present invention or derivative or variant thereof, or the polynucleotide, vector or cell of the invention. The composition of the present invention may further comprise a pharmaceutically acceptable carrier. Furthermore, the pharmaceutical composition of the present invention may comprise further agents such as interleukins or interferons depending on the intended use of the pharmaceutical composition. For use in the treatment of a tauopathic disease, e.g., of the Alzheimer's disease the additional agent may be selected from the group consisting of small organic molecules, anti-tau antibodies, and combinations thereof. Hence, in a particular embodiment the present invention relates to the use of the tau binding molecule, e.g., antibody or antigen-binding fragment thereof of the present invention or of a binding molecule having substantially the same binding specificities of any one thereof, the polynucleotide, the vector or the cell of the present invention for the preparation of a pharmaceutical or diagnostic composition for prophylactic and therapeutic treatment of a tauopathic disease, monitoring the progression of a tauopathic disease or a response to a tauopathic disease treatment in a subject or for determining a subject's risk for developing a tauopathic disease.

Hence, in one embodiment the present invention relates to a method of treating a neurological disorder characterized by abnormal accumulation and/or deposition of tau in the brain and the central nervous system, respectively, which method comprises administering to a subject in need thereof a therapeutically effective amount of any one of the aforedescribed tau binding molecules, antibodies, polynucleotides, vectors or cells of the instant invention. The term "neurological disorder" includes but is not limited to tauopathic diseases such as Alzheimer's disease, amyotrophic lateral sclerosis/parkinsonism-dementia complex, argyrophilic grain dementia, British type amyloid angiopathy, cerebral amyloid angiopathy, corticobasal degeneration, Creutzfeldt-Jakob disease, dementia pugilistica, diffuse neurofibrillary tangles with calcification, Down's syndrome, frontotemporal dementia, frontotemporal dementia with parkinsonism linked to chromosome 17, frontotemporal lobar degeneration, Gerstmann-Sträussler-Scheinker disease, Hallervorden-Spatz disease, inclusion body myositis, multiple system atrophy, myotonic dystrophy, Niemann-Pick disease type C, non-Guamanian motor neuron disease with neurofibrillary tangles, Pick's disease, postencephalitic parkinsonism, prion protein cerebral amyloid angiopathy, progressive subcortical gliosis, progressive supranuclear palsy, subacute sclerosing panencephalitis, tangle only dementia, multi-infarct dementia and ischemic stroke. Unless stated otherwise, the terms neurodegenerative, neurological or neuropsychiatric are used interchangeably herein.

A particular advantage of the therapeutic approach of the present invention lies in the fact that the antibodies of the present invention are derived from B cells or B memory cells from healthy human subjects with no signs of a tauopathic disease and thus are, with a certain probability, capable of preventing a clinically manifest tauopathic disease, or of diminishing the risk of the occurrence of the clinically manifest disease, or of delaying the onset or progression of the clinically manifest disease. Typically, the antibodies of the present invention also have already successfully gone through somatic maturation, i.e. the optimization with respect to selectivity and effectiveness in the high affinity binding to the target tau molecule by means of somatic variation of the variable regions of the antibody.

The knowledge that such cells in vivo, e.g. in a human, have not been activated by means of related or other physiological proteins or cell structures in the sense of an autoimmunological or allergic reaction is also of great medical importance since this signifies a considerably increased chance of successfully living through the clinical test phases. So to speak, efficiency, acceptability and tolerability have already been demonstrated before the preclinical and clinical development of the prophylactic or therapeutic antibody in at least one human subject. It can thus be expected that the human anti-tau antibodies of the present invention, both its target structure-specific efficiency as therapeutic agent and its decreased probability of side effects significantly increase its clinical probability of success.

The present invention also provides a pharmaceutical and diagnostic, respectively, pack or kit comprising one or more containers filled with one or more of the above described ingredients, e.g. anti-tau antibody, binding fragment, derivative or variant thereof, polynucleotide, vector or cell of the present invention. Associated with such container(s) can be a notice in the form prescribed by a governmental agency regulating the manufacture, use or sale of pharmaceuticals or biological products, which notice reflects approval by the agency of manufacture, use or sale for human administration. In addition or alternatively the kit comprises reagents and/or instructions for use in appropriate diagnostic assays. The composition, e.g. kit of the present invention is of course particularly suitable for the risk assessment, diagnosis, prevention and treatment of a disorder which is accompanied with the presence of tau, and in particular applicable for the treatment of Alzheimer's disease (AD), amyotrophic lateral sclerosis/parkinsonism-dementia complex (ALS-PDC), argyrophilic grain dementia (AGD), British type amyloid angiopathy, cerebral amyloid angiopathy, corticobasal degeneration (CBD), Creutzfeldt-Jakob disease (CJD), dementia pugilistica, diffuse neurofibrillary tangles with calcification, Down's syndrome, frontotemporal dementia, frontotemporal dementia with parkinsonism linked to chromosome 17 (FTDP-17), frontotemporal lobar degeneration, Gerstmann-Sträussler-Scheinker disease, Hallervorden-Spatz disease, inclusion body myositis, multiple system atrophy, myotonic dystrophy, Niemann-Pick disease type C (NP-C), non-Guamanian motor neuron disease with neurofibrillary tangles, Pick's disease (PiD), postencephalitic parkinsonism, prion protein cerebral amyloid angiopathy, progressive subcortical gliosis, progressive supranuclear palsy (PSP), subacute sclerosing panencephalitis, tangle only dementia, multi-infarct dementia and ischemic stroke.

The pharmaceutical compositions of the present invention can be formulated according to methods well known in the art; see for example Remington: The Science and Practice of Pharmacy (2000) by the University of Sciences in Philadelphia, ISBN 0-683-306472. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, intranasal, topical or intradermal administration or spinal or brain delivery. Aerosol formulations such as nasal spray formulations include purified aqueous or other solutions of the active agent with preservative agents and isotonic agents. Such formulations are adjusted to a pH and isotonic state compatible with the nasal mucous membranes. Formulations for rectal or vaginal ad-ministration may be presented as a suppository with a suitable carrier.

Furthermore, whereas the present invention includes the now standard (though fortunately infrequent) procedure of drilling a small hole in the skull to administer a drug of the present invention, in one aspect, the binding molecule, especially antibody or antibody based drug of the present invention can cross the blood-brain bather, which allows for intravenous or oral administration.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 μg (or of nucleic acid for expression or for inhibition of expression in this range); however, doses below or above this exemplary range are envisioned, especially considering the aforementioned factors. Generally, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, or at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated. Progress can be monitored by periodic assessment. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as dopamine or psychopharmacologic drugs, depending on the intended use of the pharmaceutical composition.

Furthermore, in a particular embodiment of the present invention the pharmaceutical composition may be formulated as a vaccine, for example, if the pharmaceutical composition of the invention comprises an anti-tau antibody or binding fragment, derivative or variant thereof for passive immunization. As mentioned in the background section, phosphor-tau species have been reported extracellularly in plasma and CSF (Aluise et al., Biochim Biophys. Acta. 1782 (2008), 549-558) and studies in transgenic mouse lines using active vaccination with phosphorylated tau peptides revealed reduced brain levels of tau aggregates in the brain and slowed progression of behavior impairments (Sigurdsson, J. Alzheimers Dis. 15 (2008), 157-168; Boimel et al., Exp Neurol. 224 (2010), 472-485). Accordingly, it is prudent to expect that passive immunization with human anti-tau antibodies and equivalent tau binding molecules of the present invention would help to circumvent several adverse effects of active immunization therapy concepts as already discussed in the background section. Therefore, the present anti-tau antibodies and their equivalents of the present invention will be particularly useful as a vaccine for the prevention or amelioration of tauopathic diseases such as AD, ALS-PDC, AGD, CBD, CJD, FTD, FTDP-17, NP-C, PiD, PSP or other tauopathies as mentioned before.

In one embodiment, it may be beneficial to use recombinant bispecific or multispecific constructs of the antibody of the present invention. For a reference see Fischer and Léger, Pathobiology 74 (2007), 3-14. Such bispecific molecule might be designed to target tau with one binding arm and another pathologic entity such as Aβ or alpha-synuclein or a different pathological conformation of tau with a second binding arm. Alternatively the second binding arm may be designed to target a protein present at the blood-brain-barrier to facilitate antibody penetration into the brain.

In one embodiment, it may be beneficial to use recombinant Fab (rFab) and single chain fragments (scFvs) of the antibody of the present invention, which might more readily penetrate a cell membrane. For example, Robert et al., Protein Eng. Des. Sel. (2008) October 16; S1741-0134, published online ahead, describe the use of chimeric recombinant Fab (rFab) and single chain fragments (scFvs) of monoclonal antibody WO-2 which recognizes an epitope in the N-terminal region of Aβ. The engineered fragments were able to (i) prevent amyloid fibrillization, (ii) disaggregate preformed Aβ1-42 fibrils and (iii) inhibit Aβ1-42 oligomer-mediated neurotoxicity in vitro as efficiently as the whole IgG molecule. The perceived advantages of using small Fab and scFv engineered antibody formats which lack the effector function include more efficient passage across the blood-brain bather and minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401.

In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies.

In a further embodiment, co-administration or sequential administration of other antibodies useful for treating a tauopathic disease may be desirable. In one embodiment, the additional antibody is comprised in the pharmaceutical composition of the present invention. Examples of antibodies which can be used to treat a subject include, but are not limited to, antibodies targeting beta-amyloid, alpha-synuclein, TDP-43 and SOD-1.

In a further embodiment, co-administration or sequential administration of other neuroprotective agents useful for treating a tauopathic disease may be desirable. In one embodiment, the additional agent is comprised in the pharmaceutical composition of the present invention. Examples of neuroprotective agents which can be used to treat a subject include, but are not limited to, an acetylcholinesterase inhibitor, a glutamatergic receptor antagonist, kinase inhibitors, HDAC inhibitors, anti-inflammatory agents, divalproex sodium, or any combination thereof. Examples of other neuroprotective agents that may be used concomitant with pharmaceutical composition of the present invention are described in the art; see, e.g. international application WO2007/011907. In one embodiment, the additional agent is dopamine or a dopamine receptor agonist.

A therapeutically effective dose or amount refers to that amount of the active ingredient sufficient to ameliorate the symptoms or condition. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. In one embodiment, the therapeutic agent in the composition is present in an amount sufficient to restore or preserve normal behavior and/or cognitive properties in case of AD, ALS-PDC, AGD, CBD, CJD, FTD, FTDP-17, NP-C, PiD, PSP or other tauopathic diseases as mentioned before.

From the foregoing, it is evident that the present invention encompasses any use of a tau binding molecule comprising at least one CDR of the above described antibody, in particular for diagnosing and/or treatment of a tauopathic disease as mentioned above, particularly Alzheimer's disease. In one embodiment, said binding molecule is an antibody of the present invention or an immunoglobulin chain thereof. In addition, the present invention relates to anti-idiotypic antibodies of any one of the mentioned antibodies described hereinbefore. These are antibodies or other binding molecules which bind to the unique antigenic peptide sequence located on an antibody's variable region near the antigen-binding site and are useful, e.g., for the detection of anti-tau antibodies in sample of a subject.

In another embodiment the present invention relates to a diagnostic composition comprising any one of the above described tau binding molecules, antibodies, antigen-binding fragments, polynucleotides, vectors or cells of the invention and optionally suitable means for detection such as reagents conventionally used in immuno or nucleic acid based diagnostic methods. The antibodies of the invention are, for example, suited for use in immunoassays in which they can be utilized in liquid phase or bound to a solid phase carrier. Examples of immunoassays which can utilize the antibody of the invention are competitive and non-competitive immunoassays in either a direct or indirect format. Examples of such immunoassays are the radioimmunoassay (RIA), the sandwich (immunometric assay), flow cytometry and the Western blot assay. The antigens and antibodies of the invention can be bound to many different carriers and used to isolate cells specifically bound thereto. Examples of well known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds; see also the embodiments discussed hereinabove.

By a further embodiment, the tau binding molecules, in particular antibodies of the present invention may also be used in a method for the diagnosis of a disorder in an individual by obtaining a body fluid sample from the tested individual which may be a blood sample, a lymph sample or any other body fluid sample and contacting the body fluid sample with an antibody of the instant invention under conditions enabling the formation of antibody-antigen complexes. The level of such complexes is then determined by methods known in the art, a level significantly higher than that formed in a control sample indicating the disease in the tested individual. In the same manner, the specific antigen bound by the antibodies of the invention may also be used. Thus, the present invention relates to an in vitro immunoassay comprising the binding molecule, e.g., antibody or antigen-binding fragment thereof of the invention.

In this context, the present invention also relates to means specifically designed for this purpose. For example, an antibody-based array may be used, which is for example loaded with antibodies or equivalent antigen-binding molecules of the present invention which specifically recognize tau. Design of microarray immunoassays is summarized in Kusnezow et al., Mol. Cell Proteomics 5 (2006), 1681-1696. Accordingly, the present invention also relates to microarrays loaded with tau binding molecules identified in accordance with the present invention.

In one embodiment, the present invention relates to a method of diagnosing a tauopathic disease in a subject, the method comprising determining the presence of tau and/or pathologically modified and/or aggregated tau in a sample from the subject to be diagnosed with at least one antibody of the present invention, an tau binding fragment thereof or an tau-binding molecule having substantially the same binding specificities of any one thereof, wherein the presence of pathologically modified and/or aggregated tau is indicative of a neurodegenerative tauopathy and an increase of the level of the pathologically modified and/or aggregated tau in comparison to the level of the physiological tau forms is indicative for progression of a neurodegenerative tauopathy in said subject.

The subject to be diagnosed may be asymptomatic or preclinical for the disease. In one embodiment, the control subject has a tauopathic disease, for example, AD, ALS-PDC, AGD, CBD, CJD, FTD, FTDP-17, NP-C, PiD, PSP or other tauopathies as mentioned before, wherein a similarity between the level of pathologically modified and/or aggregated tau and the reference standard indicates that the subject to be diagnosed has a tauopathic disease. Alternatively, or in addition as a second control the control subject does not have a tauopathic disease, wherein a difference between the level tau and/or of pathologically modified and/or aggregated tau and the reference standard indicates that the subject to be diagnosed has a tauopathic disease. In one embodiment, the subject to be diagnosed and the control subject(s) are age-matched. The sample to be analyzed may be any body fluid suspected to contain pathologically modified and/or aggregated tau, for example a blood, CSF, or urine sample.

The level tau and/or of pathologically modified and/or aggregated tau may be assessed by any suitable method known in the art comprising, e.g., analyzing tau by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), and laser densitometry. In one embodiment, said in vivo imaging of tau comprises positron emission tomography (PET), single photon emission tomography (SPECT), near infrared (NIR) optical imaging or magnetic resonance imaging (MRI).

Methods of diagnosing a tauopathic disease such as Alzheimer's disease, monitoring a tauopathic disease progression, and monitoring a tauopathic disease treatment using antibodies and related means which may be adapted in accordance with the present invention are also described in international applications WO93/08302, WO94/13795, WO95/17429, WO96/04309, WO2002/062851 and WO2004/016655. Similarly, antibody based detection methods for tau are described in international application WO2005/080986, the disclosure content of all being incorporated herein by reference. Those methods may be applied as described but with a tau specific antibody, binding fragment, derivative or variant of the present invention.

In a further aspect the present invention also relates to peptides having an epitope of tau specifically recognized by any antibody of the present invention. In one embodiment, such peptide comprises an amino acid sequence as indicated in SEQ ID NO: 7, SEQ ID NO: 41, SEQ ID NO:42 or a modified sequence thereof in which one, two, three, four, five, six, seven or more amino acids are substituted, deleted and/or added, wherein the peptide is recognized by any antibody of the present invention, for example, by antibody NI-105.4E4 or NI-105.4E3.

In one embodiment of this invention such a peptide may be used for diagnosing a neurodegenerative tauopathy in a subject, comprising a step of determining the presence of an antibody that binds to a peptide in a biological sample of said subject, and being used for diagnosis of a tauopathy in said subject by measuring the levels of antibodies which recognize the above described peptide of the present invention and comparing the measurements to the levels which are found in healthy subjects of comparable age and gender. An elevated level of measured antibodies specific for said peptide of the present invention would be indicative for diagnosing a tauopathy in said subject. The peptide of the present invention may be formulated in an array, a kit and composition, respectively, as described hereinbefore.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

The above disclosure generally describes the present invention. Unless otherwise stated, a term as used herein is given the definition as provided in the Oxford Dictionary of Biochemistry and Molecular Biology, Oxford University Press, 1997, revised 2000 and reprinted 2003, ISBN 0 19 850673 2. Several documents are cited throughout the text of this specification. Full bibliographic citations may be found at the end of the specification immediately preceding the claims. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

A more complete understanding can be obtained by reference to the following specific examples which are provided herein for purposes of illustration only and are not intended to limit the scope of the invention.

EXAMPLES

The examples which follow further illustrate the invention, but should not be construed to limit the scope of the invention in any way. The following experiments in Examples 1 to 4 are illustrated and described with respect to antibodies NI-105.4E4, NI-105.24.B2 and 105.4A3 as cloned, i.e. the framework 1 (FR1) Ig-variable regions without being adjusted to the germ line (GL) sequences of human variable heavy and light chains; see FIG. 1.

Material and Methods

Detailed descriptions of conventional methods, such as those employed herein can be found in the cited literature; see also "The Merck Manual of Diagnosis and Therapy" Seventeenth Ed. edited by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art. For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., NY); Immunochemical Methods In Cell And Molecular Biology (Mayer and Walker, eds., Academic Press, London, 1987); Handbook Of Experimental Immunology, Volumes I-IV (Weir and Blackwell, eds., 1986). Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11 (2001), 98-107.

Figure 8:
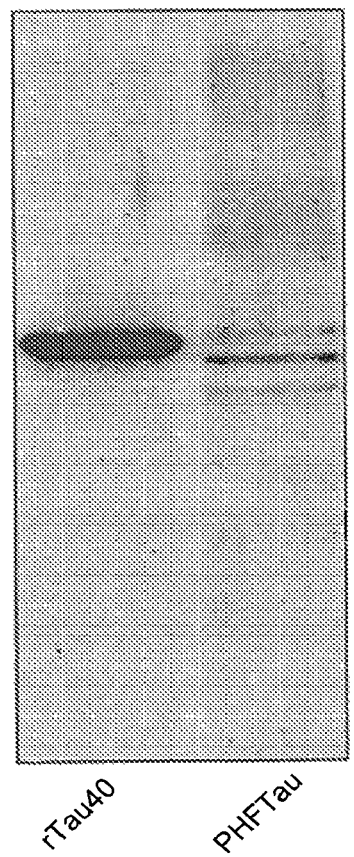
FIG. 8: PHFTau and recombinant hTau40 were resolved by gradient SDS-PAGE followed by Western Blot analysis. Blots were incubated overnight with primary antibodies NI-105.24B2 (human), followed by HRP-conjugated anti-human IgG. Recombinant human tau antibody NI-105.24B2 binds to recombinant hTau40 as well as to pathologically modified tau isoforms (PHFTau) extracted from AD brain on Western Blot analysis.
Figure 9:
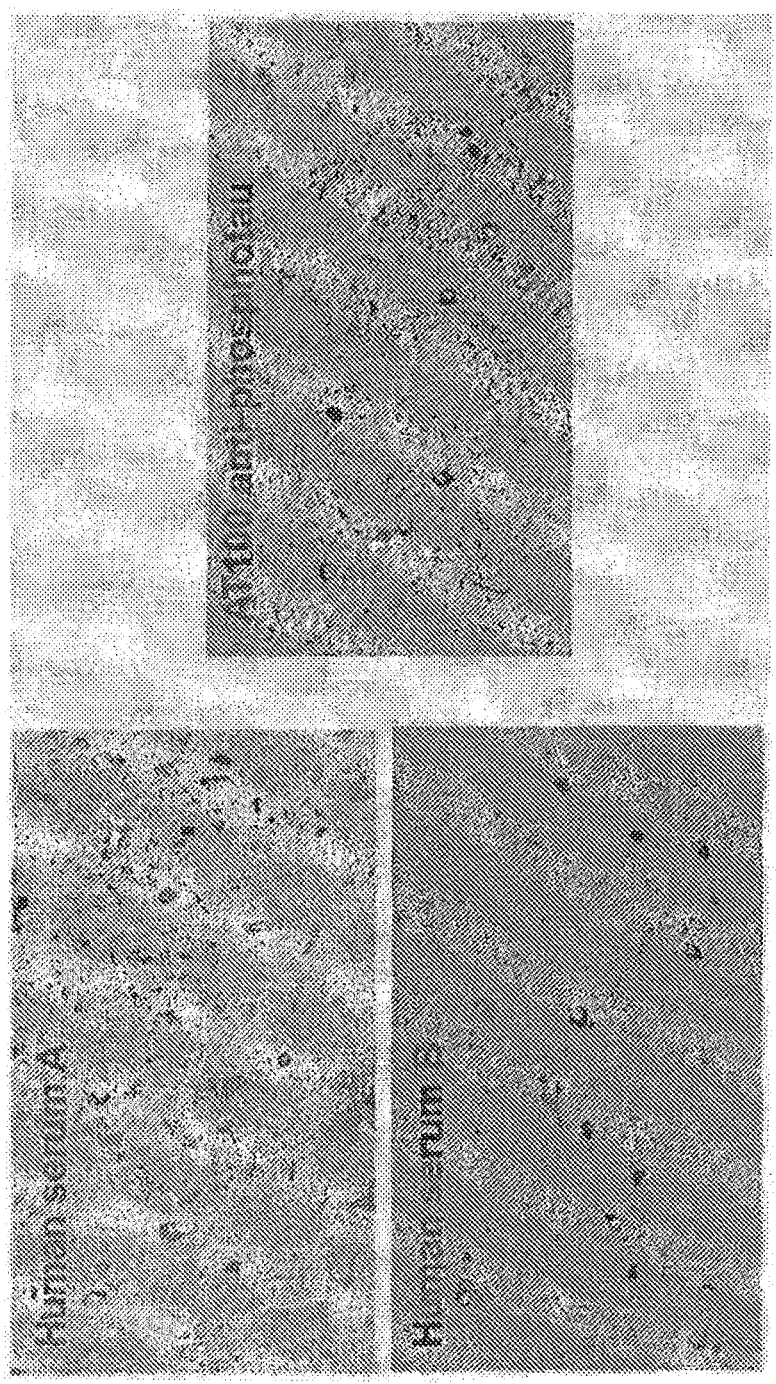
FIG. 9: Tissue amyloid plaque immunoreactivity (TAPIR) assay—Serum isolated from elderly subjects was added to histological AD brain sections. As a comparison an immunohistological staining with the commercially available AT100 anti-phospho-tau antibody was performed. Neurofibrillary tangles are stained in the control staining with AT100 anti-phospho-tau antibody when subjected to isolated sera, showing the presence of neurofibrillary tangles-reactive antibody species in the tested sera.

Methods of Identification of Tau-Specific B-Cells and Cloning of the Respective Antibodies Unless indicated otherwise below, identification of tau-specific B cells and molecular cloning of anti-tau antibodies displaying specificity of interest as well as their recombinant expression and functional characterization has been or can be generally performed as described in the Examples and Supplementary Methods section of international application PCT/EP2008/000053 published as WO2008/081008, the disclosure content of which is incorporated herein by reference in its entirety. A new method for identification of tau-specific B cells and molecular cloning of tau antibodies displaying specificity of interest as well as their recombinant expression and functional characterization is provided within this application. As described above in one embodiment of the present invention cultures of single or oligoclonal B-cells are cultured and the supernatant of the culture, which contains antibodies produced by said B-cells is screened for presence and affinity of new anti-tau antibodies therein. The screening process comprises the steps of a sensitive tissue amyloid plaque immunoreactivity (TAPIR) assay as described in Example 1 and shown in FIG. 9; screen on brain extracts for binding to PHFTau as described in Example 2 and shown in FIGS. 3 and 8; screening for binding of a peptide derived from tau of the amino acid sequence represented by SEQ ID NO:6 with phosphate groups on amino acids Ser-202 and Ser-205; on amino acid Thr-231; and/or on amino acids Ser-396 and Ser-404 of said sequence as analogously described in Example 3 and shown in FIG. 5 with non-phosphorylated peptides due to the epitope confirmation experiments for antibody NI-105.4E4; a screen for binding of full-length tau of the amino acid sequence represented by SEQ ID NO:6 and isolating the antibody for which binding is detected or the cell producing said antibody as described in international patent WO2008/081008 and as described in Example 1 and shown in FIGS. 2, 5 and 7.

Purification of Antigen

Recombinant human Tau40 was purchased from rPeptide (Bogart, Ga., USA). PHFTau was extracted from AD brain.

Isolation of paired helical filaments containing pathologically phosphorylated tau filaments (PHFTau) was performed following the method by Goedert et al. (Goedert et al., Neuron 8 (1992), 159-168) with modifications. One gram of AD brain tissue was cut into 5 mm pieces with all visible blood vessels removed. The tissue was washed with 40 ml ice cold washing solution (100 mM Tris pH 7.4, 6 mM EGTA, 1 mM Na3VO4 and 1 mM NaF) for three times followed by homogenization with 20 ml lysis buffer (10 mM Tris pH 7.4, 0.8M NaCl, 1 mM EGTA, 1× protease inhibitor cocktail, 1 mM Na3VO4, 1 mM NaF, 1 mM AEBSF, 10% sucrose). The homogenate was centrifuged at 4° C. at 20,000×g for 20 min. Supernatant was collected with addition of N-lauroyl sarcosinate (Sigma, Switzerland) to 1% (w/v). After two hours incubation at 37° C. with shaking, the supernatant was then centrifuged at 4° C. at 100,000×g for one hour. The pellet was collected and re-suspended in PBS. After clearing out possible contaminating immunoglobulins with protein A magnetic beads, the PHFTau suspension was stored at −80° C. before use. A control extract from healthy control human brain tissue was prepared accordingly.

Human Tau Antibody Screening

ELISA:

96 well half area microplates (Corning) were coated with recombinant Tau protein (rPeptide, Bogart, USA) at a standard concentration of 1 µg/ml in carbonate ELISA coating buffer (pH 9.6) overnight at 4° C. For PHFTau screening, 96 well Immobilizer Microplates (Nunc, Denmark) were coated with PHFTau extracted from human AD brain at 1:100 dilutions in carbonate ELISA coating buffer (pH9.6) overnight at 4° C. Plates were washed in PBS-T pH 7.6 and non-specific binding sites were blocked for 2 hrs at RT with PBS-T containing 2% BSA (Sigma, Buchs, Switzerland). B cell conditioned medium was transferred from memory B cell culture plates to ELISA plates and incubated for one hour at RT. ELISA plates were washed in PBS-T and then incubated with horse radish peroxidase (HRP)-conjugated donkey anti-human IgG (Fcγ fragment specific) polyclonal antibodies (Jackson immunoResearch, Newmarket, UK). After washing with PBS-T, binding of human antibodies was determined by measurement of HRP activity in a standard colorimetric assay.

MULTI-ARRAY® Microplate Screening

Standard 96 well 10-Spot MULTI-SPOT plates (Meso Scale Discovery, USA) were coated with 30 ug/ml rTau (rPeptide), PHFTau brain extract and healthy control brain extract in PBS. Non-specific binding sites were blocked for 1 hr at RT with PBS-T containing 3% BSA followed by incubation with B cell conditioned medium for 1 hr at RT. Plates were washed in PBS-T and then incubated with SULFO-Tag conjugated anti-human polyclonal antibody (Meso Scale Discovery, USA). After washing with PBS-T, bound of antibody was detected by electrochemiluminescence measurement using a SECTOR Imager 6000 (Meso Scale Discovery, USA).

Molecular Cloning of Tau Antibodies

Samples containing memory B cells were obtained from healthy human subjects. Living B cells of selected memory B cell cultures are harvested and mRNA is prepared. Immunoglobulin heavy and light chain sequences are then obtained using a nested PCR approach.

A combination of primers representing all sequence families of the human immunoglobulin germline repertoire are used for the amplifications of leader peptides, V-segments and J-segments. The first round amplification is performed using leader peptide-specific primers in 5'-end and constant region-specific primers in 3'-end (Smith et al., Nat Protoc. 4 (2009), 372-384). For heavy chains and kappa light chains, the second round amplification is performed using V-segment-specific primers at the 5'-end and J-segment-specific primers at the 3' end. For lambda light chains, the second round amplification is performed using V-segment-specific primers at the 5'-end and a C-region-specific primer at the 3' end (Marks et al., Mol. Biol. 222 (1991), 581-597; de Haard et al., J. Biol. Chem. 26 (1999), 18218-18230).

Identification of the antibody clone with the desired specificity is performed by re-screening on ELISA upon recombinant expression of complete antibodies. Recombinant expression of complete human IgG1 antibodies or chimeric IgG2a antibodies is achieved upon insertion of the variable heavy and light chain sequences "in the correct reading frame" into expression vectors that complement the variable region sequence with a sequence encoding a leader peptide at the 5'-end and at the 3'-end with a sequence encoding the appropriate constant domain(s). To that end the primers contained restriction sites designed to facilitate cloning of the variable heavy and light chain sequences into antibody expression vectors. Heavy chain immunoglobulins are expressed by inserting the immunoglobulin heavy chain RT-PCR product in frame into a heavy chain expression vector bearing a signal peptide and the constant domains of human immunoglobulin gamma 1 or mouse immunoglobulin gamma 2a. Kappa light chain immunoglobulins are expressed by inserting the kappa light chain RT-PCR-product in frame into a light chain expression vector providing a signal peptide and the constant domain of human kappa light chain immunoglobulin Lambda light chain immunoglobulins are expressed by inserting the lambda light chain RT-PCR-product in frame into a lambda light chain expression vector providing a signal peptide and the constant domain of human or mouse lambda light chain immunoglobulin.

Functional recombinant monoclonal antibodies are obtained upon co-transfection into HEK293 or CHO cells (or any other appropriate recipient cell line of human or mouse origin) of an Ig-heavy-chain expression vector and a kappa or lambda Ig-light-chain expression vector. Recombinant human monoclonal antibody is subsequently purified from the conditioned medium using a standard Protein A column purification. Recombinant human monoclonal antibody can produced in unlimited quantities using either transiently or stably transfected cells. Cell lined producing recombinant human monoclonal antibody can be established either by using the Ig-expression vectors directly or by re-cloning of Ig-variable regions into different expression vectors. Derivatives such as F(ab), F(ab)2 and scFv can also be generated from these Ig-variable regions.

Antibodies

Mouse monoclonal anti-human tau antibody Tau12 (Covance, California, U.S.A.) and mouse monoclonal tau antibody AT180 (Thermo Scientific, U.S.A.) were used according to manufacturer's protocol. Recombinant human tau antibodies NI-105.4E4, NI105.24B2 and NI-105.4A3 are antibodies of this invention. They were expressed in HEK293 or CHO cells, purified from conditioned media and were directly used in subsequent applications unless otherwise stated. In Examples 1 to 4 purified recombinant antibodies of the present invention were used.

Direct ELISA 96 well microplates (Costar, Corning, USA) were coated with recombinant Tau protein (hTau40, rPeptide, Bogart, USA) diluted to a concentration of 1 µg/ml in carbonate ELISA coating buffer (50 mM, pH9.6) at 4° C. over night. Non-specific binding sites were blocked for 2 hr at RT with PBS containing 2% BSA (Sigma, Buchs, Switzerland) and 0.5% Tween20. Binding of human antibodies of the present invention (NI-105.4E4, NI-105.24B2 and NI-105.4A3) was determined using HRP conjugated goat anti-human IgG Fcγ (Jackson immunoResearch, Newmarket, UK), followed by measurement of HRP activity in a standard colorimetric assay. EC50 values were estimated by a non-linear regression using GraphPad Prism software (San Diego, USA).

Western Blotting Protein Staining

PHFTau and recombinant hTau40 were resolved by gradient SDS-PAGE (NuPAGE 4-12%; Invitrogen, Basel, Switzerland) followed by electroblotting on nitrocellulose membranes. After blocking the non-specific binding with 2% BSA at room temperature for one hour, blots were incubated overnight with primary antibodies NI-105.4E4, NI-105.24B2 (human) or Tau12 (mouse monoclonal antibody, Covance, California, U.S.A.), followed by a HRP-conjugated goat anti-human IgGFcγ (for human primary antibodies) or a HRP-conjugated goat anti-mouse IgG secondary antibody.

Blots were developed using ECL and ImageQuant 350 detection (GE Healthcare, Otelfingen, Switzerland).

PHFTau Extraction from AD Brain

Isolation of paired helical filaments containing pathologically phosphorylated tau filaments (PHFTau) was performed following the method by Goedert et al. (Goedert et al., Neuron 8 (1992), 159-168) with modifications. One gram of AD brain tissue was cut into 5 mm pieces with all visible blood vessels removed. The tissue was washed with 40 ml ice cold washing solution (100 mM Tris pH 7.4, 6 mM EGTA, 1 mM Na3VO4 and 1 mM NaF) for three times followed by homogenization with 20 ml lysis buffer (10 mM Tris pH 7.4, 0.8M NaCl, 1 mM EGTA, 1× protease inhibitor cocktail, 1 mM Na3VO4, 1 mM NaF, 1 mM AEBSF, 10% sucrose). The homogenate was centrifuged at 4° C. at 20,000×g for 20 min. Supernatant was collected with addition of N-lauroyl sarcosinate (Sigma, Switzerland) to 1% (w/v). After two hours incubation at 37° C. with shaking, the supernatant was then centrifuged at 4° C. at 100,000×g for one hour. The pellet was collected and resuspended in PBS. After clearing out possible contaminating immunoglobulins with protein A magnetic beads, the PHFTau suspension was stored at −80° C. before use. A control extract from healthy control human brain tissue was prepared accordingly.

Tau Peptides Synthesis

A peptide corresponding to amino acids 333-346 of hTau40 (333GGGQVEVKSEKLDF346) which includes the epitope of NI-105.4E4 identified by Pepspot mapping (amino acids 337-343) was synthesized by Schafer-N(Copenhagen, Denmark). An additional cysteine was added to the C-terminus to allow for covalent binding to Immobilizer Microplates (Nunc, Denmark). A second peptide corresponding to amino acids 226-239 of human tau (226 VAV-VRpTPPKSPSSA239), the cognate epitope of the commercially available mouse monoclonal tau antibody AT180 (Thermo Scientific, USA) was synthesized accordingly and used as control.

Transgenic Mice

Three different animal models for tauopathies are used to validate the tau antibodies (and molecules with the binding specificities thereof) of the present invention.

1. Transgenic TauP301L mice (line 183): expressing human Tau40 with P301L mutation under the murine Thy1.2 promoter (Generation of these transgenic animals is described in Götz et al., J. Biol. Chem. 276 (2001), 529-534 and in international application WO 2003/017918, the disclosure content of which is incorporated herein by reference)

2. JNPL3 mice expressing the shortest human tau isoform with P301L mutation under the murine PrP promoter (available from Taconic, Hudson, N.Y., U.S.A).

3. P301STau (line PS19) mice expressing human tau with P301S mutation under the murine PrP promoter (available from the Jackson Laboratory, Bar Harbor, Me., U.S.A).

Tauopathies mouse models and corresponding wild type mice are kept under standard housing conditions on a reversed 12 h:12 h light/dark cycle with free access to food and water. The treatment groups are balanced for age and gender.

Example 1

Validation of Target and Binding Specificity of Human Tau-Antibodies

Figure 10:
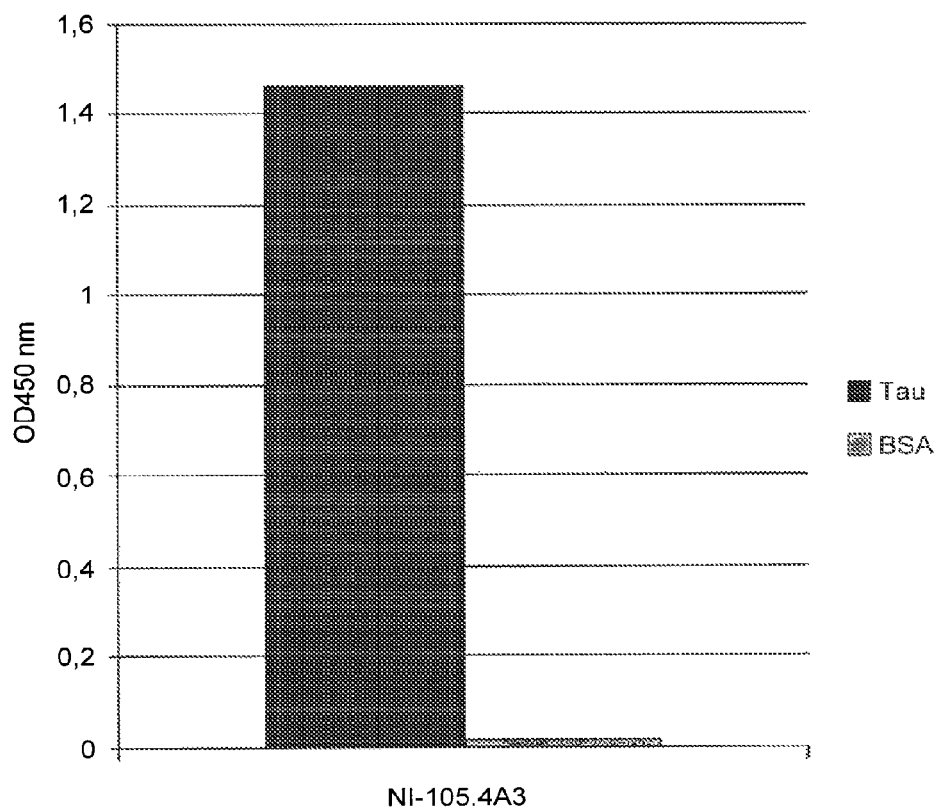
FIG. 10: Recombinant human antibody NI-105.4A3 specifically binds to human tau by ELISA. No binding is observed to BSA.

To validate tau as a recognized target of isolated antibodies direct ELISA assays were performed as described above. For the exemplary recombinant human NI-105.4A3 antibody 96 well microplates (Costar, Corning, USA) were coated with recombinant human tau (hTau40, rPeptide, Bogart, USA) diluted to a concentration of 3 μg/ml or with BSA in carbonate ELISA coating buffer (pH 9.6) and binding efficiency of the antibody was tested. The exemplary NI-105.4A3 antibody specifically binds to human tau by ELISA. No binding is observed to BSA (FIG. 10).

Figure 7:
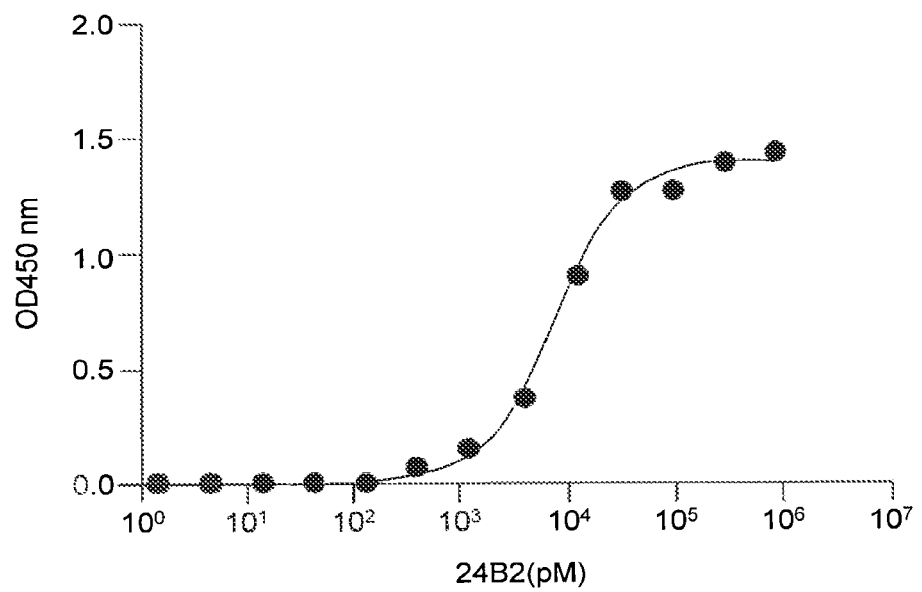
FIG. 7: ELISA plates were coated with recombinant human tau (hTau40) at 3 µg/ml and incubated with the indicated concentrations of NI-105.24B2 antibody. Recombinant human derived antibody NI-105.24B2 binds to hTau40 with high affinity at 6 nM $EC_{50}$.

For a determination of the half maximal effective concentration (EC50) of the exemplary antibodies NI-105.4E4 and NI-105.24B2 additional direct ELISA experiments with varying antibody concentrations were performed. 96 well microplates (Costar, Corning, USA) were coated with recombinant human tau (hTau40, rPeptide, Bogart, USA) diluted to a concentration of 1 μg/ml (for the assay with NI-105.4E4 Antibody), or of 3 μg/ml (for the assay with NI-105.24B2 Antibody) in carbonate ELISA coating buffer and binding efficiency of the antibody was tested. The EC50 values were estimated by a non-linear regression using GraphPad Prism software. Recombinant human-derived antibody NI-105.4E4 binds to hTau40 with high affinity in the low nanomolar range at 2.4 nM EC50 (FIG. 2). NI-105.24B2 binds to hTau40 with high affinity in the low nanomolar range at 6.6 nM EC50 (FIG. 7).

Figure 12:
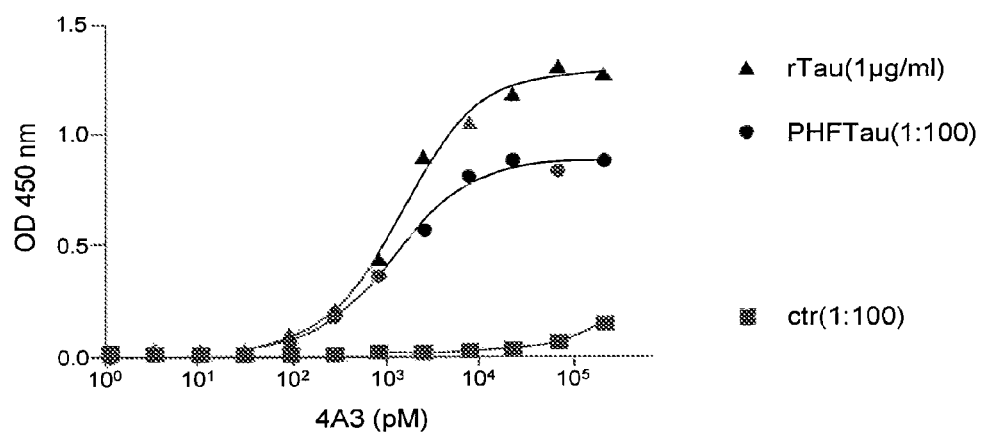
FIG. 12: ELISA plates were coated with recombinant human tau (hTau40, 1 ug/ml), PHFTau (1:100) and control preparation (1:100), and incubated with indicated concentration of NI-105.4A3. 4A3 binds to rTau with 1.4 nM EC50, to PHFTau with 1.2 nM EC50.

The half maximal effective concentration (EC50) of the exemplary antibody NI-105.4A3 was also determined using direct ELISA experiments. ELISA plates were coated with recombinant human tau (hTau40, 1 ug/ml), PHFTau (1:100) and control preparation (1:100), and incubated with varying antibody concentrations. NI-105.4A3 binds to rTau with high affinity in the low nanomolar range at 1.4 nM EC50. NI-105.4A3 binds to PHFTau with high affinity in the low nanomolar range at 1.2 nM EC50 (FIG. 12).

Example 2

Figure 3:
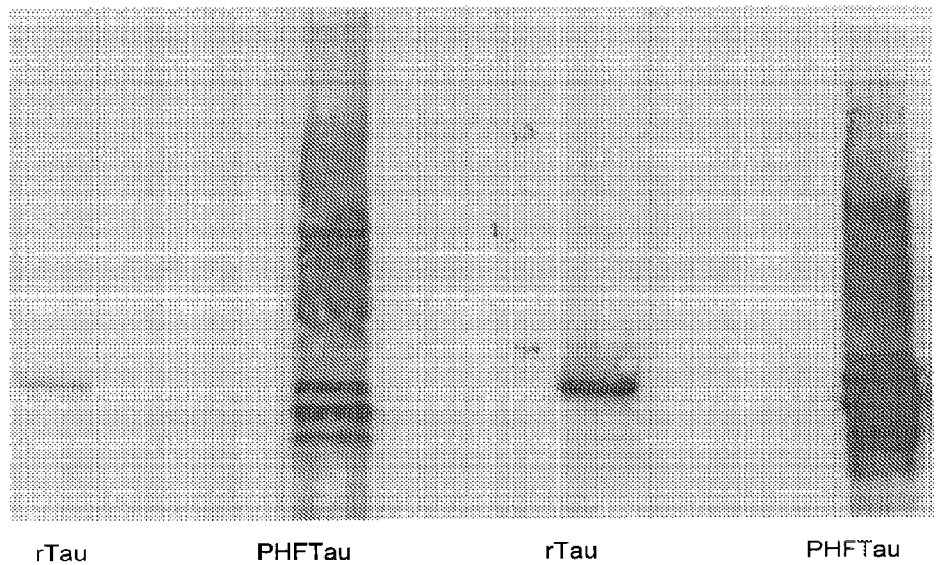
FIG. 3: PHFTau and recombinant hTau40 were resolved by gradient SDS-PAGE followed by Western Blot analysis. Blots were incubated with primary antibodies NI-105.4E4 (human) or mouse monoclonal Tau12 antibody, followed by HRP-conjugated secondary antibodies. Recombinant human tau antibody NI-105.4E4 binds to recombinant hTau40 as well as to pathologically modified tau isoforms (PHFTau) extracted from AD brain on Western blot analysis.

Recombinant Human Antibodies Binding Analysis to Recombinant Tau and Pathological Tau Extracted from AD Brain To determine the binding capacity of NI-105.4E4 and NI-105.24B2 to pathological tau species extracted from AD brain. SDS-PAGE and Western Blot analysis was performed as described in detail above. Blots were incubated overnight with primary antibodies NI-105.4E4 (human), NI-105.24B2 (human) or Tau12 (mouse monoclonal antibody, Covance, California, U.S.A.), followed by a HRP-conjugated goat anti-human IgGFcγ (for human antibodies) or a HRP-conjugated goat anti-mouse IgG secondary antibody. Recombinant antibodies NI-105.4E4 (FIG. 3) and NI-105.24B2 (FIG. 8) recognize recombinant hTau40 as well as pathologically modified PHFTau extracted from AD brain on Western blot. As expected, control antibody Tau12 recognizes both tau species as well (FIG. 3).

Additionally, as discussed in Example 1 above, the half maximal effective concentration (EC50) of the exemplary antibody NI-105.4A3 was determined in direct ELISA experiments using PHFTau. NI-105.4A3 binds to PHFTau with high affinity in the low nanomolar range at 1.2 nM EC50 (FIG. 12).

Example 3

Mapping of the NI-105.4E4 and NI-105.4A3 Binding Epitope on hTau40

Figure 4A:
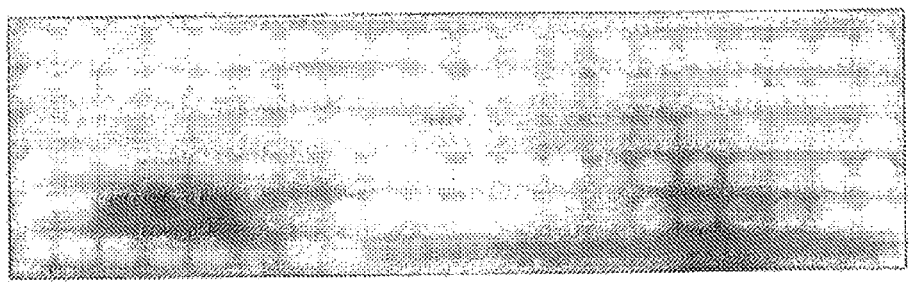
Figure 4A:
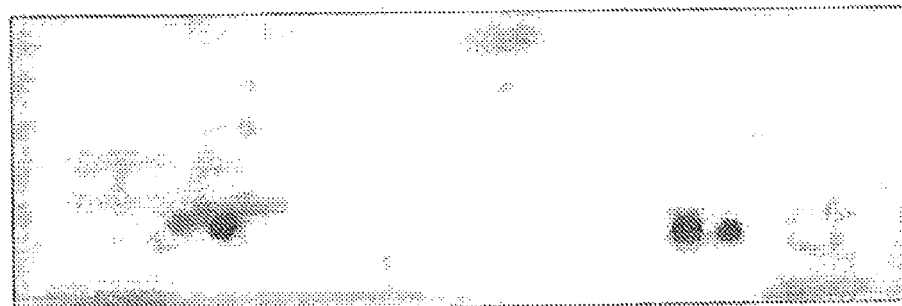
Figure 4B:
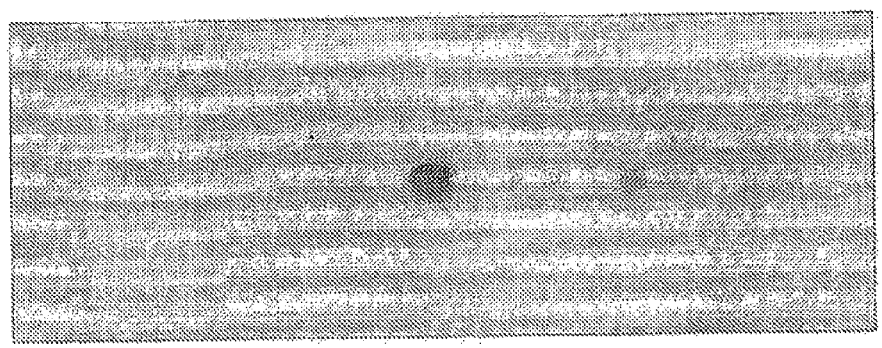

A peptide array of 118 peptide sequences covering the full-length hTau40 (amino acids 1-441) with an overlap of 11 amino acids between two adjacent peptides was spotted on a nitrocellulose membrane (JPT Peptide Technologies GmbH, Berlin, Germany) Immunolabeling of antibodies as well as membrane regeneration were carried out according to manufacturer's instructions. To rule out non-specific binding of the detection antibody, the membrane was first probed by HRP-conjugated goat anti-human IgG omitting the primary antibody (FIG. 4B). After regeneration the membrane was probed with 100 nM recombinant NI-105.4E4 antibody. Bound antibody was detected using ECL and ImageQuant 350 detection (GE Healthcare, Otelfingen, Switzerland).

Two groups of adjacent peptide spots (peptide 83, 84 and 85; peptide 96 and 97) were specifically identified by NI105.4E4 (FIG. 4A), when compared to the detection antibody only (FIG. 4B). The sequences covered by these two groups of peptides correspond to amino acids 329-351 and 387-397 of hTau40. These data suggest that NI-105.4E4 recognizes a discontinuous epitope comprising two linear sequences: one within the R4 microtubule binding domain and another in the C-terminal domain.

The sequence shared by peptides 83-85 comprises amino acid residues 337-343 of hTau40. The Pepspot (JPT) data suggest that NI-105.4E4 recognizes an epitope in hTau that comprises amino acids 337-343 of human tau. This region is located within the microtubule binding domain of tau and is conserved among all neuronal human tau isoforms as well as across other species including mouse and rat.

As this domain is bound to microtubules in physiological microtubule-associated tau, NI-105.4E4 is expected to preferentially target the pathologically relevant pool of tau that is detached from the microtubules.

Figures 4C, 4D:
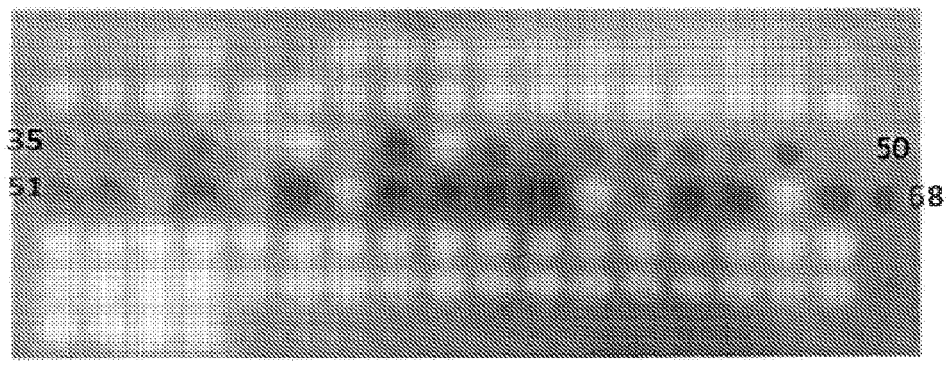

To determine key residues within the NI-105.4E4 binding peptides, alanin scanning was performed to substitute each residue with alanine one at a time. The alanine residues in the original sequence (A384 and A390) were substituted to proline and glycine (FIG. 4E). Spots 35-50 and 51-68 (FIG. 4C) are the original peptides (spot 35 and spot 51) and their alanine substituted variants, whose amino acid sequences are shown in FIGS. 4D and E. Alanine scan suggests V339, E342, D387, E391 and K395 are necessary for NI-105.4E4 binding.

Figure 5:
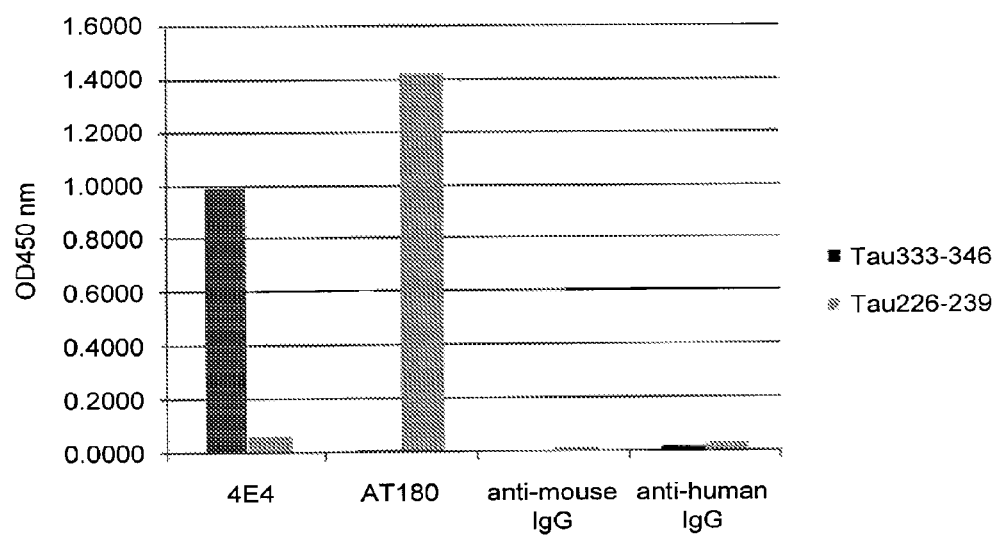
FIG. 5: Confirmation that the human recombinant NI-105.4E4 antibody binds specifically to a tau peptide corresponding to amino acids 333-346 of hTau40.

An additional experiment has been performed by testing the binding of NI-105.4E4 to tau peptides. Direct ELISA shows that NI-105.4E4 specifically recognizes a peptide corresponding to amino acid 333-346 of hTau40, which contains the amino acid residues 337-343 identified by Pepspot mapping (FIG. 5). No cross-reactivity of NI-105.4E4 is observed to the control peptide covering the AT180 epitope. Vice versa, AT180 recognizes its cognate epitope containing peptide but fails to bind to the NI-105.4E4 specific peptide. Species-specific secondary antibodies do not bind to any of the peptides. Together, direct ELISA with coated peptides confirms that NI-105.4E4 specifically recognizes a peptide containing the amino acid residues 337-343 of human tau identified by Pepspot mapping.

Figure 13:
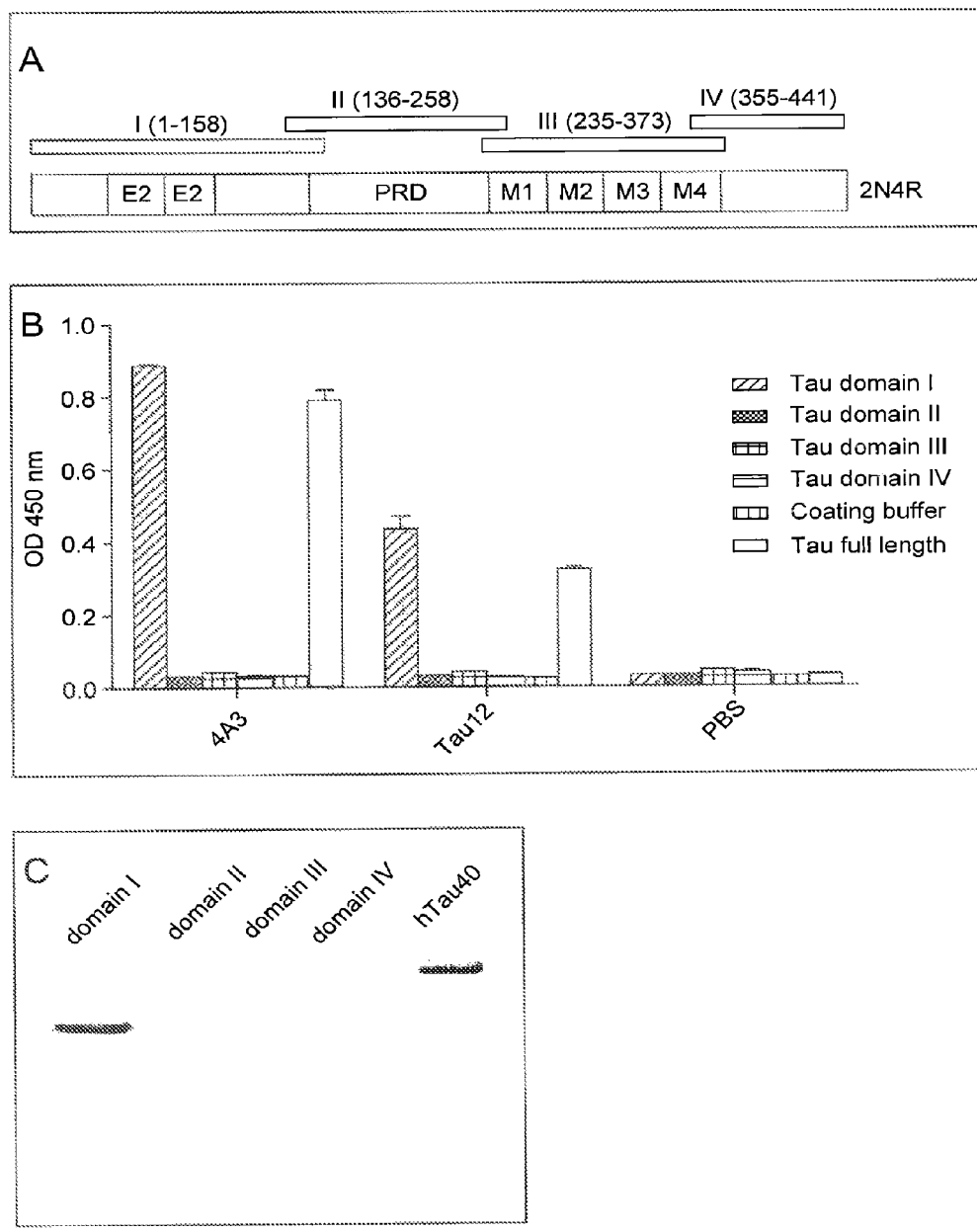
FIG. 13: Mapping of the NI-105.4A3 binding epitope on hTau40. (A) Schematic representation of the four overlapping hTau40 domains (domain I (AA 1-158), domain II (AA 136-258), domain III (AA 235-373), and domain IV (AA 355-441)) used. (B) NI-105.4A3 binds only tau domain I and the full length hTau40 polypeptide. (C) Western blot confirms the specific bonding of NI-105.4A3 to tau domain I.

To grossly map the NI-105.4A3 binding epitope on hTau40, four tau domain polypeptides (Tau domain I, domain II, domain III and domain IV) were produced. DNA fragments, synthesized using GeneArt® (Invitrogen), which encode each Tau domain with 6× His tagged at the N-terminus were cloned into the pRSET-A expression vector (Invitrogen), were transfected into E. Coli BL21 (DE3) (New England Biolabs). The expressions of the His-tagged Tau domains were induced by 0.5 mM IPTG for six hours before bacteria were lysed with lysozyme with sonication. The lysate was boiled for five minutes before being further purified with Ni-NTA Superflow Columns (Qiagen). The eluted His-tagged Tau domains were coated on ELISA plates or loaded on polyacrylamide gel for Western Blot. These sequentially overlapping tau domain polypeptides cover the full length of hTau40 (FIG. 13A). Purified tau domains were coated on ELISA plate and the binding of NI-105.4A3 was tested. NI-105.4A3 binds only to tau domain I and the full length hTau40, indicating the epitope is within the N-terminal part of the hTau40 (aa1-136) (FIG. 13B). Western blot confirms the specific binding of NI-105.4A3 to tau domain I (FIG. 13C).

NI-105.4A3 epitope mapping with PepSpot (JPT) technology identified amino acids Q35-Q49 of the human Tau40 (FIGS. 14A and C). To determine key residues within the epitope for NI-105.4A3 binding, alanine scanning was performed to substitute each residue with alanine one at a time. The alanine residue in the original sequence (A41) was substituted with glycine and proline (FIG. 14B). Spots numbered from left to right with 1 and 17 are the original epitope (spot 1) and its alanine substitutions, whose amino acid sequences are shown in FIG. 14C. Alanine scan showed that D40, A41 and K44 are key residues for NI-105.4A3 binding.

Example 4

Assessment of the Binding of NI-105.4E4 to Physiological Forms as Well as Pathological Aggregates of Tau AD Brain Tissues and in Human Tau Transgenic Mice Neurofibrillary tangles (NFT) composed of hyperphosphorylated tau filaments are a neuropathological hallmarks of AD. Hyperphosphorylated tau filaments are also the major components of dystrophic neurites and neuropil threads, both of which are common neuropathological features in AD. Overexpression of human tau containing the familial P301L tau mutation in mice induces NFT formation at six months of age (Gotz et al., 2001a).

To assess the binding of recombinant human tau antibody to physiological forms as well as pathological aggregates of tau, immunohistological stainings were performed in AD brain tissues and in TauP301L transgenic mice with the exemplary NI-105.4E4 antibody of this invention.

Mice were perfused with 20 ml 100 mM TrisCl/6 mM EGTA (pH7.4) at room temperature under deep anesthesia. Brains were taken out and immersed in 4% PFA in PBS (pH 7.4) at 4° C. over night for fixation followed by embedding in paraffin. For human tissue, paraffin blocks of brain tissues from AD and healthy control subjects were used. DAB staining was carried out following standard protocols. As positive control, mouse monoclonal antibody Tau-12 (Covance, California, U.S.A.) was used. HRP-conjugated detection antibodies without primary antibodies were also included.

Recombinant human antibody NI-105.4E4 identifies numerous NFTs and neuropil threads in AD brain (FIG. 6A), which are absent in healthy control brain (FIG. 6B). Secondary antibody alone does not give signals in both AD (FIG. 6C) and control brain (FIG. 6D). In P301L tau transgenic mouse brain, NI-105.4E4 binds strongly to the pathological tau resembling NFT (FIGS. 6 E, F and H), neuropil threads (FIGS. 6 E and G) and dystrophic neurites (FIGS. 6 E and H). In addition, NI-105.4E4 also identifies tau aggregates at pre-tangle stage (FIG. 6 I). In the brain of transgenic mice overexpressing both human P301L tau and human APP with Swedish and Arctic mutations, NI-105.4E4 binds specifically to dystrophic neurites surrounding beta-amyloid plaques (FIG. 6 J).

Example 5

In Vivo Tests of the Antibodies of the Present Invention

As already described above studies in transgenic mouse lines using active vaccination with phosphorylated tau peptides revealed reduced brain levels of tau aggregates in the brain and slowed progression of behavior impairments (Sigurdsson, J. Alzheimers Dis. 15 (2008), 157-168; Boimel et al., Exp. Neurol. 224 (2010), 472-485). However, active vaccination may not be particularly useable in humans because a significant fraction of the elderly population is expected to be non-responders to vaccination. Furthermore, the potential side effects associated with a tau-directed immune response can be difficult to control. Tau binding molecules of the present invention may be reasonably expected to achieve similar reductions in brain levels of tau aggregates as described above for the mouse antibodies, because of their similar binding specificities against pathologically tau species. However, because of the evolutionarily optimization and affinity maturation within the human immune system antibodies of the present invention provide a valuable therapeutic tool due to being isolated from healthy human subjects with high probability for excellent safety profile and lack of immunogenicity. Confirmation of these expected therapeutic effects may be provided by test methods as described in the above mentioned experiments with mouse antibodies. In particular, the antibodies to be screened may be applied on diverse possible routes to the animals such as intraperitoneal antibody injection, intracranial injection, intraventricular brain infusion and tested for treatment effects. Either of the above mentioned application possibilities may be also used after prior brain injection of beta-amyloid preparations into the brain of tau transgenic mice to evaluate treatment effects on beta amyloid-induced tau pathology.

Evaluation of the treatment effects may be performed by histochemical methods comprising quantification of Gallyas positive cells counts, total human tau staining, brain burden of phosphorylated tau and/or a biochemical determination of brain soluble and insoluble tau and phosphor-tau levels upon sequential brain extraction. Further on, behavior testing of the treated mice may be performed, e.g., conditioned taste aversion or contextual fear conditioning for a confirmation of the therapeutic effects of the antibodies of the present invention (Pennanen, Genes Brain Behav. 5 (2006), 369-79, Pennanen Neurobiol Dis. 15 (2004), 500-9.)

Example 6

Chimerization of Antibodies 4E4 and 4A3 with Mouse IgG2a Constant Domains

In order to generate antibodies with reduced immunogenicity for use in chronic treatment studies, mouse chimeric versions of antibodies 4E4 and 4A3 were generated using recombinant DNA technology. A mouse IgG2a/lambda isotype was selected for these chimeric antibodies, in order to generate a molecule which bound with high affinity to mouse Fc-gamma receptors, and was therefore capable of inducing an immune effector response. The amino acid sequences of the chimeric 4E4 (ch4E4) and chimeric 4A3 (ch4A3) heavy and light chain constructs are shown below.

TABLE 3

Amino acid sequences of chimeric 4E4 (ch4E4 and chimeric 4A3 (ch4A3).

| | |
|---|---|
| mature ch4E4 heavy chain (mouse IgG2a) SEQ ID NO: 20 | EVQLVESGGGLVQPGGSLKLSCAASGFNFNISAIHWVRQASGKGLEWVGR IRSKSHNYATLYAASLKGRFTLSRDDSRNTAYLQMSSLQTEDMAVYYCTV LSANYDTFDYWGQGTLVTVSSAKTTAPSVYPLAPVCGDTTGSSVTLGCLV KGYFPEPVTLIWNSGSLSSGVHTFPAVLQSDLYTLSSSVIVISSTWPSQS ITCNVAHPASSTKVDKKIEPRGPTIKPCPPCKCPAPNLLGGPSVFIFPPK IKDVLMISLSPIVICVVVDVSEDDPDVQISWFVNNVEVHTAQTQTHREDY NSTLRVVSALPIQHQDWMSGKEFKCKVNNKDLPAPIERTISKPKGSVRAP QVYVLPPPEEEMTKKQVILTCMVIDFMPEDIYVEWTNNGKTELNYKNTEP VLDSDGSYFMYSKLRVEKKNWVERNSYSCSVVHEGLHNHHTTKSFSRTPG K |
| mature ch4E4 light chain (mouse lambda) SEQ ID NO: 21 | SYELTQPPSVSVSPGQTARISCFGDTLPKQYTYWYQQKPGQAPVLVIYKD TERPSGIPERFSGSSSGTTVTLTISGVQAEDEADYYCLSADNSATWVFGG GTKVTVLGQPKSSPSVTLFPPSSEELETNKATLVCTITDFYPGVVTVDWK VDGTPVTQGMETTQPSKQSNNKYMASSYLTLTARAWERHSSYSCQVTHEG HTVEKSLSRADCS |

Example 7

Chimerization of Antibodies 4E4 and 4A3 with Mouse IgG2a Constant Domains

Figure 15:
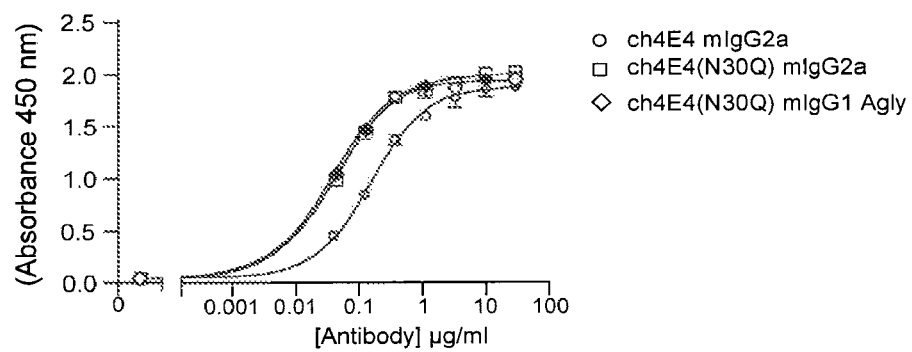
FIG. 15: Binding of ch4E4 and variants to recombinant tau (ELISA).

A consensus N-linked glycosylation site was identified in the CDR1 region of the 4E4 heavy chain. Upon mammalian (CHO) cell expression, the predicted N-glycosylation site (Asn-30) was fully occupied by glycan, as demonstrated by mass spectrometry. In order to eliminate N-glycosylation in this region and reduce product heterogeneity, Asn-30 of the heavy chain of ch4E4 was changed to Gln (Table 4). When produced and purified from CHO cells, the modified antibody bound to recombinant tau with ~4-fold higher apparent binding affinity relative to the original, glycosylated antibody (see FIG. 15).

TABLE 4

Amino acid sequences of mature ch4E4(N30Q) heavy chain (mouse IgG2a). Substituted Gln residue is in bold, underlined.

| | |
|---|---|
| mature ch4E4 (N30Q) heavy chain (mouse IgG2a) SEQ ID NO: 22 | EVQLVESGGGLVQPGGSLKLSCAASGFNFQISAIHWVRQASGKGLEWVGR IRSKSHNYATLYAASLKGRFTLSRDDSRNTAYLQMSSLQTEDMAVYYCTV LSANYDTFDYWGQGTLVTVSSAKTTAPSVYPLAPVCGDTTGSSVTLGCLV KGYFPEPVTLIWNSGSLSSGVHTFPAVLQSDLYTLSSSVIVISSTWPSQS ITCNVAHPASSTKVDKKIEPRGPTIKPCPPCKCPAPNLLGGPSVFIFPPK IKDVLMISLSPIVICVVVDVSEDDPDVQISWFVNNVEVHTAQTQTHREDY NSTLRVVSALPIQHQDWMSGKEFKCKVNNKDLPAPIERTISKPKGSVRAP QVYVLPPPEEEMTKKQVILTCMVIDFMPEDIYVEWTNNGKTELNYKNTEP VLDSDGSYFMYSKLRVEKKNWVERNSYSCSVVHEGLHNHHTTKSFSRTPG K |

Example 8

Production of Aglycosylated Chimeric 4E4 (ch4E4(N30Q) mIgG1 Agly)

A mouse chimeric aglycosylated variant of 4E4 was produced (ch4E4(N30Q) IgG1-Agly) in order to evaluate the relationship between antibody effector function and activity. For the heavy chain, the variable domain of 4E4 were fused to a mouse IgG1 heavy chain containing an Asn to Gln mutation to eliminate the consensus Fc glycosylation site. The heavy chain variable region also contained the N30Q change in order to eliminate the consensus N-glycosylation site in CDR1 (Example 7). The light chain was the ch4E4 lambda light chain described above.

Example 9

Acute Brain Penetration Study of Human 4E4 and 4A3

Human 4E4 and 4A3 were produced by transient transfection of CHO cells and purified by affinity purification. The endotoxin levels were controlled and were all bellow 1 EU/mg. TauP301L mice were intraperitoneally injected with 30 mg/kg 4E4 (n=7), 4A3 (n=7) antibody or equal volume of PBS (n=7) at day 1 and day 4. At day 5, mice were perfused under anesthesia with PBS containing 1 Unit/ml heparin. Blood, brain and spinal cord were collected for analyses. Right hemisphere of the brain was frozen at −80° C., left hemisphere of the brain and the spinal cord were post fixed in 10% neutralized formalin at 4° C. for two days before being embedded in paraffin block and sectioned. Plasma was stored at −80° C. in aliquots.

Brain protein extraction: frozen right hemisphere was weighed and homogenized in 5 volumes (5 mL/g of wet tissue) of a solution containing 50 mM NaCl, 0.2% diethylamine, protease inhibitors (Roche Diagnostics GmbH) and phosphatase inhibitor (Roche Diagnostics GmbH). Samples were then transferred to polycarbonate tubes and added another 5 volume of homogenization solution, and kept on ice for 30 min. Soluble fraction was then collected after centrifugation at 100,000 g, 4° C. for 30 min. This soluble fraction was used in human IgG assay. The pellet was re-suspended in 3 volumes of PBS with protease and phosphatase inhibitor. After centrifugation at 16,000 g, 4° C. for 30 min, supernatants and pellets were stored separately at −80° C. for further insoluble tau extraction. Pellets further extracted with modified sarcosyl extraction (Goedert M, Spillantini M G, Cairns N J, Crowther R A. Neuron 8, 159 (1992)).

Figure 17:
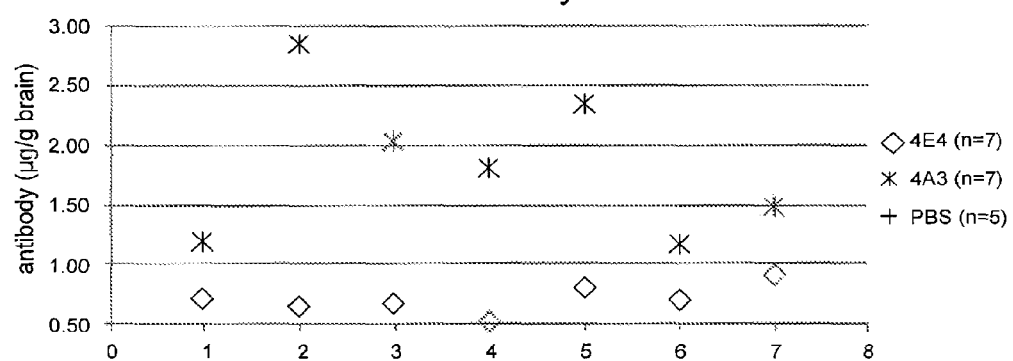
FIG. 17: Human IgG levels in brain homogenate of mice following intraperitoneal administration of 30 mg/kg 4E4 or 4A3 human anti-tau antibody.

Human IgG-specific sandwich ELISA: 2 μg/ml of goat anti-human IgG Fab (Jackson) in 50 mM carbonate ELISA coating buffer (pH9.6) was used as capture antibody. Half-area 96-well microtitre plates was coated with 30 μl/well with capture antibody at 4° C. over night. The plate was then washed 4 times with PBS containing 0.1% Tween 20 before incubating with 50 μl/well PBS containing 2% BSA at room temperature for one hour. Soluble fractions of brain extracts, plasma samples and antibody standard (4A3) were diluted in PBS containing 2% BSA and 0.1% Tween 20. 30 μl of the diluted samples were added into each well and incubated at room temperature for one hour. The plate was then washed with 200 μl/well PBS containing 0.1% Tween 20 for four times before incubated with HRP-conjugated donkey anti-human Fcγ (Jackson, diluted at 1:10,000 in PBS containing 2% BSA and 0.1% Tween 20) at room temperature for one hour. The plate was then washed with 200 μl/well PBS containing 0.1% Tween 20 for four times before adding 20 μl/well TMB (1:20 in 10 mM citrate solution pH=4.1). The reaction was then stopped by adding 10 μl 1M H2SO4 to each well. Antibody standard curve was obtained from serial dilutions of 4A3. Antibody concentrations in plasma and brain samples were calculated according to the standards. Brain human IgG level was then converted to μg antibody/gram fresh brain tissue (assuming 1 g/10 ml) as indicated in FIG. 17.

Figure 16:
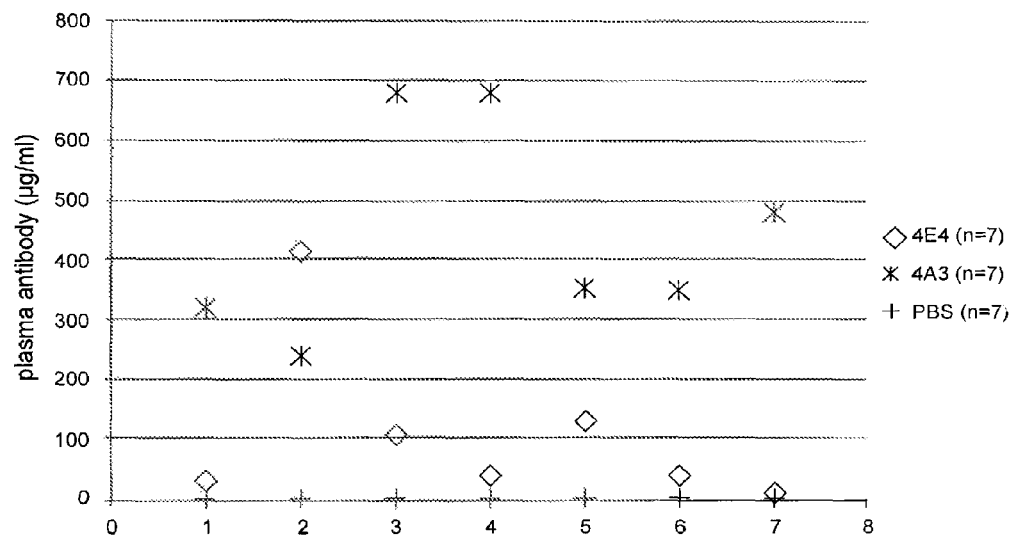
FIG. 16: Human IgG levels in the plasma of mice following intraperitoneal administration of 30 mg/kg 4E4 or 4A3 human anti-tau antibody.

High levels of human IgG were detected in the plasma of all 4E4 and 4A3 treated mice. In contrast, no human IgG was detected in the plasma of PBS treated mice (FIG. 16). Significant amount of human IgG was detected in brain homogenates of 4E4 and 4A3 treated mice (FIG. 17).

Example 10

Chronic Study with Chimeric 4E4 and 4A3

Chimeric 4E4 and 4A3 containing the variable domains of the original human antibody and the constant regions of mouse IgG2a may be produced by transient transfection of CHO cells and purified by affinity purification. The endotoxin levels in each batch of the antibodies will be controlled and kept below 1 Eu/mg. Gender balanced TauP301L mice at age of 7.5-8 months will be intraperitoneally injected with 10 mg/kg, 3 mg/kg of antibody solution, or equal volume of PBS control. Each treatment group will have 20-25 mice. The treatment will be carried out once a week for 26 weeks. Alternatively, the treatment will be carried out twice a week for 13 weeks. Body weight will be monitored every two weeks. Mice will be perfused under anesthesia at the end of the treatment period. Brain, spinal cord and blood will be collected. Half brain and spinal cord may be post-fixed in 10% formalin for three days before being embedded in paraffin block. 4-6 nm thick sections cut from these tissue blocks may be used for immunohistochemistry studies. The other half brain will be weighted and deep frozen at −80° C. for biochemical analyses.

Drug effects will be evaluated by comparing the level of neurofibrillary tangles (NFT) and the level of tau with different solubility characteristics in treated and control samples. NFT may be visualized by Gallyas silver impregnation (F Gallyas Acta Morphol. Acad. Sci. Hung 19.1 (1971)), or by immunostaining with monoclonal mouse antibody AT100 and AT180, which recognize pathologically phosphorylated tau in NFT. The number or frequency of Gallyas-positive neurons and/or AT100, AT180 labeled neurons in the brain and spinal cord in antibody treated mice and control animals may be determined to evaluate the effect of antibody treatment.

Soluble and insoluble tau may be extracted following the brain protein extraction protocol described herein. Alternatively, soluble and insoluble tau may be extracted with modified sarcosyl extraction (Goedert M, Spillantini M G, Cairns N J, Crowther R A. Neuron 8, 159 (1992)). Briefly, frozen brain is homogenized in 10 volumes (wt/vol) of 10% sucrose homogenate buffer consisting of 10 mM Tris.HCl (pH 7.4), 0.8 M NaCl, 1 mM EGTA, 1 mM Na3VO4, 1 mM NaF, 1 mM AEBSF, protease inhibitors (Roche Diagnostics GmbH) and phosphatase inhibitor (Roche Diagnostics GmbH). The homogenate is spun for 20 min at 20,000 g, and the supernatant retained. The pellet is homogenized in 10 volumes of homogenization buffer and centrifuged for a second time. The supernatants may be pooled together, and N-lauryl-sarkosinate (Sigma) is added to 1% (wt/vol) final concentration, and incubated at 37° C. with 300 rpm rotation for 1.5 hour, followed by centrifugation at 100,000 g for 1 h. The supernatant is collected as sarcosyl soluble fraction and the pellet of 1 g brain tissue is re-suspended in 0.2 ml 50 mM Tris.HCl (pH 7.4) as PHF fraction.

The levels of soluble and insoluble tau will be measured with commercially available Tau ELISA kits (Invitrogen). In addition, brain protein extracts will be separated with 4-12% Bis-Tris SDS-PAGE followed immunoblotting with Tau12 (human tau), AT8 (pS202/pT205), AT100 (pT212/pS214), AT180 (pT231) and E178 (pS396) antibodies. Semi-quantitative analysis will be performed with measuring the integrated density of each samples against standards of known quantities of tau.

Additionally, improvement of working memory in antibody treated mice can be tested using a two-trial Y-maze task. The three arms of the maze are 22 cm long, 5 cm wide and 15 cm deep. Black and white abstractive clues are placed on a black curtain surrounding the maze. Experiments are conducted with an ambient light level of 6 lux during the dark phase. Each experiment comprises a training session and an observation session. During the training session, a mouse is assigned to two of the three arms (the start arm and the second arm), which can be freely explored during 4 min, with no access to the third arm (the novel arm). The mouse is then removed from the maze and kept in a holding cage for 1.5-5 min, while the maze is thoroughly cleaned with 70% ethanol to remove any olfactory clues. The mouse is then put back again in the maze for observation with all three arms accessible for 4 min. The number of entry to each arm, the time spent in each arm, and the ratio of time spent in the novel third arm over the average of time spent in the other two arms (start arm and second arm) is calculated and compared among different treatment groups.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A polynucleotide or polynucleotides encoding an anti-tau antibody or a tau-binding fragment thereof, wherein the anti-tau antibody or tau-binding fragment comprises a heavy chain variable region (VH) and a light chain variable region (VL), wherein:
   (a) the VH comprises a heavy chain CDR1, CDR2, and CDR3 with the amino acid sequences set forth in SEQ ID NO:23, 24, and 25, respectively;
   (b) the VL comprises a light chain CDR1, CDR2, and CDR3 with the amino acid sequences set forth in SEQ ID NO:26, 27, and 28, respectively; and
   wherein the VH does not comprise an asparagine at Kabat numbering position 30.

2. The polynucleotide or polynucleotides of claim 1, wherein the antibody or tau-binding fragment thereof is selected from the group consisting of a single chain Fv fragment (scFv), an F(ab') fragment, an F(ab) fragment, and an F(ab')2 fragment.

3. The polynucleotide or polynucleotides of claim 1, wherein the VH comprises a glutamine at Kabat numbering position 30.

4. The polynucleotide or polynucleotides of claim 1, wherein the antibody or tau-binding fragment thereof is a human or a chimeric human-murine antibody.

5. The polynucleotide or polynucleotides of claim 1, wherein the antibody or tau-binding fragment thereof is a human monoclonal antibody.

6. A vector or vectors comprising the polynucleotide or polynucleotides of claim 1.

7. A host cell comprising the polynucleotide or polynucleotides of claim 1.

8. A method for preparing an anti-tau antibody or tau-binding fragment thereof, the method comprising:
   (a) culturing the host cell of claim 7; and
   (b) isolating the anti-tau antibody or tau-binding fragment thereof from the culture.

9. A polynucleotide or polynucleotides encoding an anti-tau antibody or a tau-binding fragment thereof, wherein the anti-tau antibody or tau-binding fragment comprises a heavy chain variable region (VH) and a light chain variable region (VL), and wherein:
   (a) the VH comprises a heavy chain CDR1, CDR2, and CDR3 with the amino acid sequences set forth in SEQ ID NO:23, 24, and 25, respectively;

(b) the VL comprises a light chain CDR1, CDR2, and CDR3 with the amino acid sequences set forth in SEQ ID NO:26, 27, and 28, respectively; and
(c) the antibody does not comprise the amino acid sequence of SEQ ID NO:9 and/or SEQ ID NO:11.

10. The polynucleotide or polynucleotides of claim 9, wherein the antibody or tau-binding fragment thereof is a human or a chimeric human-murine antibody.

11. The polynucleotide or polynucleotides of claim 9, wherein the antibody or tau-binding fragment thereof is a human monoclonal antibody.

12. A vector comprising the polynucleotide or polynucleotides of claim 11.

13. A host cell comprising the polynucleotide or polynucleotides of claim 11.

14. A method for preparing an anti-tau antibody or tau-binding fragment thereof, the method comprising:
(a) culturing the host cell of claim 13; and
(b) isolating the anti-tau antibody or tau-binding fragment thereof from the culture.

15. A polynucleotide or polynucleotides linked to a heterologous nucleic acid, wherein the polynucleotide or polynucleotides are selected from the group consisting of:
(a) a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively, wherein the VH when paired with a light chain variable region (VL) comprising the amino acid sequence set forth in SEQ ID NO:11 binds to tau (SEQ ID NO:6);
(b) a polynucleotide encoding an immunoglobulin light chain or a fragment thereof comprising a VL comprising CDRs 1, 2, and 3 with the amino acid sequences set forth in SEQ ID NOs:26, 27, and 28, respectively, wherein the VL when paired with a VH comprising the amino acid sequence set forth in SEQ ID NO:9 binds to tau (SEQ ID NO:6);
(c) a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively; and (ii) an immunoglobulin light chain or a fragment thereof comprising a light chain variable region (VL) comprising CDRs 1, 2, and 3 with the amino acid sequences set forth in SEQ ID NOs:26, 27, and 28, respectively;
(d) a polynucleotide encoding an immunoglobulin heavy chain or a fragment thereof comprising a VH comprising the amino acid sequence set forth in SEQ ID NO:9, wherein the VH when paired with a VL comprising the amino acid sequence set forth in SEQ ID NO:11 binds to tau (SEQ ID NO:6);
(e) a polynucleotide encoding an immunoglobulin light chain or a fragment thereof comprising a VL comprising the amino acid sequence set forth in SEQ ID NO:11, wherein the VL when paired with a VH comprising the amino acid sequence set forth in SEQ ID NO:9 binds to tau (SEQ ID NO:6);
(f) a polynucleotide or polynucleotides encoding an immunoglobulin heavy chain or a fragment thereof comprising a VH comprising the amino acid sequence set forth in SEQ ID NO:9 and an immunoglobulin light chain or a fragment thereof comprising a VL comprising the amino acid sequence set forth in SEQ ID NO:11;
(g) a polynucleotide encoding an immunoglobulin heavy chain or a fragment thereof, comprising the nucleic acid sequence set forth in SEQ ID NO:8;
(h) a polynucleotide encoding an immunoglobulin light chain or a fragment thereof, comprising the nucleic acid sequence set forth in SEQ ID NO:10;
(a') a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:29, 30, and 31, respectively, wherein the VH when paired with a light chain variable region (VL) comprising the amino acid sequence set forth in SEQ ID NO:15 binds to tau (SEQ ID NO:6);
(b') a polynucleotide encoding an immunoglobulin light chain or a fragment thereof comprising a VL comprising CDRs 1, 2, and 3 with the amino acid sequences set forth in SEQ ID NOs:32, 33, and 34, respectively, wherein the VL when paired with a VH comprising the amino acid sequence set forth in SEQ ID NO:13 binds to tau (SEQ ID NO:6);
(c') a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:29, 30, and 31, respectively; and (ii) an immunoglobulin light chain or a fragment thereof comprising a light chain variable region (VL) comprising CDRs 1, 2, and 3 with the amino acid sequences set forth in SEQ ID NOs:32, 33, and 34, respectively;
(d') a polynucleotide encoding an immunoglobulin heavy chain or a fragment thereof comprising a VH comprising the amino acid sequence set forth in SEQ ID NO:13, wherein the VH when paired with a VL comprising the amino acid sequence set forth in SEQ ID NO:15 binds to tau (SEQ ID NO:6);
(e') a polynucleotide encoding an immunoglobulin light chain or a fragment thereof comprising a VL comprising the amino acid sequence set forth in SEQ ID NO:15, wherein the VL when paired with a VH comprising the amino acid sequence set forth in SEQ ID NO:13 binds to tau (SEQ ID NO:6);
(f') a polynucleotide or polynucleotides encoding an immunoglobulin heavy chain or a fragment thereof comprising a VH comprising the amino acid sequence set forth in SEQ ID NO:13 and an immunoglobulin light chain or a fragment thereof comprising a VL comprising the amino acid sequence set forth in SEQ ID NO:15;
(g') a polynucleotide encoding an immunoglobulin heavy chain or a fragment thereof, comprising the nucleic acid sequence set forth in SEQ ID NO:12;
(h') a polynucleotide encoding an immunoglobulin light chain or a fragment thereof, comprising the nucleic acid sequence set forth in SEQ ID NO:14;
(a") a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:35, 36, and 37, respectively, wherein the VH when paired with a light chain variable region (VL) comprising the amino acid sequence set forth in SEQ ID NO:19 binds to tau (SEQ ID NO:6);

(b") a polynucleotide encoding an immunoglobulin light chain or a fragment thereof comprising a VL comprising CDRs 1, 2, and 3 with the amino acid sequences set forth in SEQ ID NOs:38, 39, and 40, respectively, wherein the VL when paired with a VH comprising the amino acid sequence set forth in SEQ ID NO:17 binds to tau (SEQ ID NO:6);

(c") a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:35, 36, and 37, respectively; and (ii) an immunoglobulin light chain or a fragment thereof comprising a light chain variable region (VL) comprising CDRs 1, 2, and 3 with the amino acid sequences set forth in SEQ ID NOs:38, 39, and 40, respectively;

(d") a polynucleotide encoding an immunoglobulin heavy chain or a fragment thereof comprising a VH comprising the amino acid sequence set forth in SEQ ID NO:17, wherein the VH when paired with a VL comprising the amino acid sequence set forth in SEQ ID NO:19 binds to tau (SEQ ID NO:6);

(e") a polynucleotide encoding an immunoglobulin light chain or a fragment thereof comprising a VL comprising the amino acid sequence set forth in SEQ ID NO:19, wherein the VL when paired with a VH comprising the amino acid sequence set forth in SEQ ID NO:17 binds to tau (SEQ ID NO:6);

(f") a polynucleotide or polynucleotides encoding an immunoglobulin heavy chain or a fragment thereof comprising a VH comprising the amino acid sequence set forth in SEQ ID NO:17 and an immunoglobulin light chain or a fragment thereof comprising a VL comprising the amino acid sequence set forth in SEQ ID NO:19;

(g") a polynucleotide encoding an immunoglobulin heavy chain or a fragment thereof, comprising the nucleic acid sequence set forth in SEQ ID NO:16; and (h") a polynucleotide encoding an immunoglobulin light chain or a fragment thereof, comprising the nucleic acid sequence set forth in SEQ ID NO:18.

16. The polynucleotide or polynucleotides of claim 15, wherein the heterologous nucleic acid is a regulatory element.

17. The polynucleotide or polynucleotides of claim 16, wherein the regulatory element is a promoter, an enhancer, a ribosome binding site, or a transcription terminator.

18. The polynucleotide or polynucleotides of claim 15, wherein the heterologous nucleic acid is a secretory signal peptide.

19. The polynucleotide or polynucleotides of claim 18, wherein the secretory signal peptide is a mammalian signal peptide.

20. The polynucleotide or polynucleotides of claim 19, wherein the mammalian signal peptide is from tissue plasminogen activator.

21. A vector or vectors comprising a polynucleotide or polynucleotides selected from the group consisting of:

(a) a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively, wherein the VH when paired with a light chain variable region (VL) comprising the amino acid sequence set forth in SEQ ID NO:11 binds to tau (SEQ ID NO:6);

(b) a polynucleotide encoding an immunoglobulin light chain or a fragment thereof comprising a VL comprising CDRs 1, 2, and 3 with the amino acid sequences set forth in SEQ ID NOs:26, 27, and 28, respectively, wherein the VL when paired with a VH comprising the amino acid sequence set forth in SEQ ID NO:9 binds to tau (SEQ ID NO:6);

(c) a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively; and (ii) an immunoglobulin light chain or a fragment thereof comprising a light chain variable region (VL) comprising CDRs 1, 2, and 3 with the amino acid sequences set forth in SEQ ID NOs:26, 27, and 28, respectively;

(d) a polynucleotide encoding an immunoglobulin heavy chain or a fragment thereof comprising a VH comprising the amino acid sequence set forth in SEQ ID NO:9, wherein the VH when paired with a VL comprising the amino acid sequence set forth in SEQ ID NO:11 binds to tau (SEQ ID NO:6);

(e) a polynucleotide encoding an immunoglobulin light chain or a fragment thereof comprising a VL comprising the amino acid sequence set forth in SEQ ID NO:11, wherein the VL when paired with a VH comprising the amino acid sequence set forth in SEQ ID NO:9 binds to tau (SEQ ID NO:6);

(f) a polynucleotide or polynucleotides encoding an immunoglobulin heavy chain or a fragment thereof comprising a VH comprising the amino acid sequence set forth in SEQ ID NO:9 and an immunoglobulin light chain or a fragment thereof comprising a VL comprising the amino acid sequence set forth in SEQ ID NO:11;

(g) a polynucleotide encoding an immunoglobulin heavy chain or a fragment thereof, comprising the nucleic acid sequence set forth in SEQ ID NO:8;

(h) a polynucleotide encoding an immunoglobulin light chain or a fragment thereof, comprising the nucleic acid sequence set forth in SEQ ID NO: 10;

(a') a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:29, 30, and 31, respectively, wherein the VH when paired with a light chain variable region (VL) comprising the amino acid sequence set forth in SEQ ID NO:15 binds to tau (SEQ ID NO:6);

(b') a polynucleotide encoding an immunoglobulin light chain or a fragment thereof comprising a VL comprising CDRs 1, 2, and 3 with the amino acid sequences set forth in SEQ ID NOs:32, 33, and 34, respectively, wherein the VL when paired with a VH comprising the amino acid sequence set forth in SEQ ID NO:13 binds to tau (SEQ ID NO:6);

(c') a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:29, 30, and 31, respectively; and (ii) an immunoglobulin light chain or a fragment thereof comprising a light chain variable region (VL) comprising CDRs 1, 2, and 3 with the amino acid sequences set forth in SEQ ID NOs:32, 33, and 34, respectively;

(d') a polynucleotide encoding an immunoglobulin heavy chain or a fragment thereof comprising a VH comprising the amino acid sequence set forth in SEQ ID NO:13, wherein the VH when paired with a VL comprising the amino acid sequence set forth in SEQ ID NO:15 binds to tau (SEQ ID NO:6);

(e') a polynucleotide encoding an immunoglobulin light chain or a fragment thereof comprising a VL comprising the amino acid sequence set forth in SEQ ID NO:15, wherein the VL when paired with a VH comprising the amino acid sequence set forth in SEQ ID NO:13 binds to tau (SEQ ID NO:6);

(f') a polynucleotide or polynucleotides encoding an immunoglobulin heavy chain or a fragment thereof comprising a VH comprising the amino acid sequence set forth in SEQ ID NO:13 and an immunoglobulin light chain or a fragment thereof comprising a VL comprising the amino acid sequence set forth in SEQ ID NO:15;

(g') a polynucleotide encoding an immunoglobulin heavy chain or a fragment thereof, comprising the nucleic acid sequence set forth in SEQ ID NO:12;

(h') a polynucleotide encoding an immunoglobulin light chain or a fragment thereof, comprising the nucleic acid sequence set forth in SEQ ID NO:14;

(a") a polynucleotide encoding an immunoglobulin heavy chain or a fragment thereof comprising a heavy chain variable region (VH) comprising complementarity determining regions (CDRs) 1, 2, and 3 with the amino acid sequences set forth in SEQ ID NOs:35, 36, and 37, respectively, wherein the VH when paired with a light chain variable region (VL) comprising the amino acid sequence set forth in SEQ ID NO:19 binds to tau (SEQ ID NO:6);

(b") a polynucleotide encoding an immunoglobulin light chain or a fragment thereof comprising a VL comprising CDRs 1, 2, and 3 with the amino acid sequences set forth in SEQ ID NOs:38, 39, and 40, respectively, wherein the VL when paired with a VH comprising the amino acid sequence set forth in SEQ ID NO:17 binds to tau (SEQ ID NO:6);

(c") a polynucleotide or polynucleotides encoding (i) an immunoglobulin heavy chain or a fragment thereof comprising a heavy chain variable region (VH) comprising complementarity determining regions (CDRs) 1, 2, and 3 with the amino acid sequences set forth in SEQ ID NOs:35, 36, and 37, respectively; and (ii) an immunoglobulin light chain or a fragment thereof comprising a light chain variable region (VL) comprising CDRs 1, 2, and 3 with the amino acid sequences set forth in SEQ ID NOs:38, 39, and 40, respectively;

(d") a polynucleotide encoding an immunoglobulin heavy chain or a fragment thereof comprising a VH comprising the amino acid sequence set forth in SEQ ID NO:17, wherein the VH when paired with a VL comprising the amino acid sequence set forth in SEQ ID NO:19 binds to tau (SEQ ID NO:6);

(e") a polynucleotide encoding an immunoglobulin light chain or a fragment thereof comprising a VL comprising the amino acid sequence set forth in SEQ ID NO:19, wherein the VL when paired with a VH comprising the amino acid sequence set forth in SEQ ID NO:17 binds to tau (SEQ ID NO:6);

(f") a polynucleotide or polynucleotides encoding an immunoglobulin heavy chain or a fragment thereof comprising a VH comprising the amino acid sequence set forth in SEQ ID NO:17 and an immunoglobulin light chain or a fragment thereof comprising a VL comprising the amino acid sequence set forth in SEQ ID NO:19;

(g") a polynucleotide encoding an immunoglobulin heavy chain or a fragment thereof, comprising the nucleic acid sequence set forth in SEQ ID NO:16; and (h") a polynucleotide encoding an immunoglobulin light chain or a fragment thereof, comprising the nucleic acid sequence set forth in SEQ ID NO:18.

22. A host cell comprising the vector or vectors of claim 21.

23. A polynucleotide encoding an immunoglobulin heavy chain or a fragment thereof comprising a VH comprising CDRs 1, 2, and 3 with the amino acid sequences set forth in SEQ ID NOs:23, 24, and 25, respectively, wherein the VH does not comprise an asparagine at Kabat numbering position 30, and wherein the VH when paired with a VL comprising the amino acid sequence set forth in SEQ ID NO:11 binds to tau (SEQ ID NO:6).

24. A vector comprising the polynucleotide of claim 23.

25. A host cell comprising the polynucleotide of claim 23.

26. A polynucleotide encoding an immunoglobulin heavy chain or a fragment thereof comprising a VH comprising the amino acid sequence set forth in SEQ ID NO:9, with the exception that the VH does not comprise an asparagine at Kabat numbering position 30, and wherein the VH when paired with a VL comprising the amino acid sequence set forth in SEQ ID NO:11 binds to tau (SEQ ID NO:6).

27. A vector comprising the polynucleotide of claim 26.

28. A host cell comprising the polynucleotide of claim 26.

29. A polynucleotide that encodes encoding an immunoglobulin heavy chain or a fragment thereof comprising a VH comprising the amino acid sequence set forth in SEQ ID NO:93, wherein the VH when paired with a VL comprising the amino acid sequence set forth in SEQ ID NO:11 binds to tau (SEQ ID NO:6).

30. A polynucleotide or polynucleotides encoding an anti-tau antibody or a tau-binding fragment thereof, wherein the anti-tau antibody or tau-binding fragment comprises a heavy chain variable region (VH) and a light chain variable region (VL), wherein:
(a) the VH comprises a heavy chain CDR1, CDR2, and CDR3 with the amino acid sequences set forth in SEQ ID NO:29, 30, and 31, respectively;
(b) the VL comprises a light chain CDR1, CDR2, and CDR3 with the amino acid sequences set forth in SEQ ID NO:32, 33, and 34, respectively; and
(c) the antibody does not comprise the amino acid sequence of SEQ ID NO:13 and/or SEQ ID NO:15.

31. A vector comprising the polynucleotide or polynucleotides of claim 30.

32. A host cell comprising the polynucleotide or polynucleotides of claim 30.

33. A method for preparing an anti-tau antibody or tau-binding fragment thereof, the method comprising:
(a) culturing the host cell of claim 32; and
(b) isolating the anti-tau antibody or tau-binding fragment thereof from the culture.

34. A polynucleotide or polynucleotides encoding an anti-tau antibody or a tau-binding fragment thereof, wherein the anti-tau antibody or tau-binding fragment comprises a heavy chain variable region (VH) and a light chain variable region (VL), wherein
  (a) the VH comprises a heavy chain CDR1, CDR2, and CDR3 with the amino acid sequences set forth in SEQ ID NO:35, 36, and 37, respectively;
  (b) the VL comprises a light chain CDR1, CDR2, and CDR3 with the amino acid sequences set forth in SEQ ID NO:38, 39, and 40, respectively; and
  (c) the antibody does not comprise the amino acid sequence of SEQ ID NO:17 and/or SEQ ID NO:19.

35. A vector comprising the polynucleotide or polynucleotides of claim 34.

36. A host cell comprising the polynucleotide or polynucleotides of claim 34.

37. A method for preparing an anti-tau antibody or tau-binding fragment thereof, the method comprising:
  (a) culturing the host cell of claim 36; and
  (b) isolating the anti-tau antibody or tau-binding fragment thereof from the culture.

38. A cDNA comprising a polynucleotide encoding a polypeptide comprising:
  an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively, and wherein the VH when paired with a light chain variable region (VL) comprising the amino acid sequence set forth in SEQ ID NO:11 binds to tau; or
  an immunoglobulin light chain or a fragment thereof comprising a VL comprising CDRs 1, 2, and 3 with the amino acid sequences set forth in SEQ ID NOs:26, 27, and 28, respectively, and wherein the VL when paired with a VH comprising the amino acid sequence set forth in SEQ ID NO:9 binds to tau.

39. The cDNA of claim 38, wherein the polypeptide comprises:
  an immunoglobulin heavy chain or fragment thereof comprising a VH with the amino acid sequence set forth in SEQ ID NO:9;
  an immunoglobulin heavy chain or fragment thereof comprising a VH with the amino acid sequence set forth in SEQ ID NO:93; or
  an immunoglobulin light chain or fragment thereof comprising a VL with the amino acid sequence set forth in SEQ ID NO:11.

40. An expression vector comprising a heterologous promoter operably linked to a polynucleotide encoding a polypeptide comprising:
  an immunoglobulin heavy chain or a fragment thereof comprising a heavy chain variable region (VH) comprising complementarity determining regions (CDRs) 1, 2, and 3 with the amino acid sequences set forth in SEQ ID NOs:23, 24, and 25, respectively, and wherein the VH when paired with a light chain variable region (VL) comprising the amino acid sequence set forth in SEQ ID NO:11 binds to tau; or
  an immunoglobulin light chain or a fragment thereof comprising a VL comprising CDRs 1, 2, and 3 with the amino acid sequences set forth in SEQ ID NOs:26, 27, and 28, respectively, and wherein the VL when paired with a VH comprising the amino acid sequence set forth in SEQ ID NO:9 binds to tau.

41. The expression vector of claim 40, wherein the polypeptide comprises:
  an immunoglobulin heavy chain or fragment thereof comprising a VH with the amino acid sequence set forth in SEQ ID NO:9;
  an immunoglobulin heavy chain or fragment thereof comprising a VH with the amino acid sequence set forth in SEQ ID NO:93; or
  an immunoglobulin light chain or fragment thereof comprising a VL with the amino acid sequence set forth in SEQ ID NO:11.

42. An expression vector comprising:
  a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:23, 24, and 25, respectively; and
  a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:26, 27, and 28, respectively,
  wherein the immunoglobulin heavy chain or fragment thereof when paired with the immunoglobulin light chain or fragment thereof forms an anti-human tau antibody or human tau-binding fragment thereof, and
  wherein the expression vector is a plasmid, phage, or virus.

43. The expression vector of claim 42, wherein:
  the VH consists of the amino acid sequence set forth in SEQ ID NO:9; and
  the VL consists of the amino acid sequence set forth in SEQ ID NO:11.

44. The expression vector of claim 42, wherein:
  the VH consists of the amino acid sequence set forth in SEQ ID NO:93; and
  the VL consists of the amino acid sequence set forth in SEQ ID NO:11.

45. A host cell comprising:
  a first expression vector comprising a first heterologous promoter operably linked to a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:23, 24, and 25, respectively; and
  a second expression vector comprising a second heterologous promoter operably linked to a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:26, 27, and 28, respectively,
  wherein the immunoglobulin heavy chain or fragment thereof when paired with the immunoglobulin light chain or fragment thereof forms an anti-human tau antibody or human tau-binding fragment thereof.

46. The host cell of claim 45, wherein the first heterologous promoter is a cytomegalovirus, simian virus 40, or retroviral promoter and the second heterologous promoter is a cytomegalovirus, simian virus 40, or retroviral promoter.

47. The host cell of claim 45, wherein the first expression vector is a plasmid, phage, or virus and the second expression vector is a plasmid, phage, or virus.

48. The host cell of claim 45, wherein:
the VH consists of the amino acid sequence set forth in SEQ ID NO:9; and
the VL consists of the amino acid sequence set forth in SEQ ID NO:11.

49. The host cell of claim 45, wherein:
the VH consists of the amino acid sequence set forth in SEQ ID NO:93; and
the VL consists of the amino acid sequence set forth in SEQ ID NO:11.

50. The host cell of claim 49, wherein the first polypeptide comprises a human IgG1 heavy chain constant region and the second polypeptide comprises a human lambda light chain constant region.

51. The host cell of claim 45, wherein the host cell is a mammalian host cell.

52. The host cell of claim 45, wherein the host cell is a Chinese Hamster Ovary (CHO) cell, a HEK 293 cell, or a NSO cell.

53. A host cell comprising an expression vector comprising:
a first polynucleotide encoding a first polypeptide comprising an immunoglobulin heavy chain or a fragment thereof comprising a heavy chain variable region (VH) comprising VH complementarity determining regions (CDRs) 1, 2, and 3 with the amino acid sequences set forth in SEQ ID NOs:23, 24, and 25, respectively; and
a second polynucleotide encoding a second polypeptide comprising an immunoglobulin light chain or a fragment thereof comprising a light chain variable region (VL) comprising VL CDRs 1, 2, and 3 with the amino acid sequences set forth in SEQ ID NOs:26, 27, and 28, respectively,
wherein the immunoglobulin heavy chain or fragment thereof when paired with the immunoglobulin light chain or fragment thereof forms an anti-human tau antibody or human tau-binding fragment thereof, and
wherein the expression vector is a plasmid, phage, or virus.

54. The host cell of claim 53, wherein:
the VH consists of the amino acid sequence set forth in SEQ ID NO:9; and
the VL consists of the amino acid sequence set forth in SEQ ID NO:11.

55. The host cell of claim 53, wherein:
the VH consists of the amino acid sequence set forth in SEQ ID NO:93; and
the VL consists of the amino acid sequence set forth in SEQ ID NO:11.

56. The host cell of claim 55, wherein the first polypeptide comprises a human IgG1 heavy chain constant region and the second polypeptide comprises a human lambda light chain constant region.

57. The host cell of claim 53, wherein the host cell is a mammalian host cell.

58. The host cell of claim 53, wherein the host cell is a Chinese Hamster Ovary (CHO) cell, a HEK 293 cell, or a NSO cell.

59. A method for preparing an anti-human tau antibody or human tau-binding fragment thereof, the method comprising:
culturing the host cell of claim 45 in a cell culture; and
isolating the anti-human tau antibody or human tau-binding fragment thereof from the cell culture.

60. The method of claim 59, further comprising formulating the anti-human tau antibody or human tau-binding fragment thereof into a sterile pharmaceutical composition suitable for administration to a human subject.

61. The method of claim 60, wherein the pharmaceutical composition is suitable for intravenous or subcutaneous administration.

62. The method of claim 59, wherein:
the VH consists of the amino acid sequence set forth in SEQ ID NO:9; and
the VL consists of the amino acid sequence set forth in SEQ ID NO:11.

63. The method of claim 59, wherein:
the VH consists of the amino acid sequence set forth in SEQ ID NO:93; and
the VL consists of the amino acid sequence set forth in SEQ ID NO:11.

64. The method of claim 63, wherein the first polypeptide comprises a human IgG1 heavy chain constant region and the second polypeptide comprises a human lambda light chain constant region.

65. A method for preparing an anti-human tau antibody or human tau-binding fragment thereof, the method comprising:
culturing the host cell of claim 53 in a cell culture; and
isolating the anti-human tau antibody or human tau-binding fragment thereof from the cell culture.

66. The method of claim 65, further comprising formulating the anti-human tau antibody or human tau-binding fragment thereof into a sterile pharmaceutical composition suitable for administration to a human subject.

67. The method of claim 66, wherein the pharmaceutical composition is suitable for intravenous or subcutaneous administration.

68. The method of claim 65, wherein:
the VH consists of the amino acid sequence set forth in SEQ ID NO:9; and
the VL consists of the amino acid sequence set forth in SEQ ID NO:11.

69. The method of claim 65, wherein:
the VH consists of the amino acid sequence set forth in SEQ ID NO:93; and
the VL consists of the amino acid sequence set forth in SEQ ID NO:11.

70. The method of claim 69, wherein the first polypeptide comprises a human IgG1 heavy chain constant region and the second polypeptide comprises a human lambda light chain constant region.

* * * * *